(12) United States Patent
Prakash et al.

(10) Patent No.: US 12,247,238 B2
(45) Date of Patent: Mar. 11, 2025

(54) MOGROSIDE BIOCATALYSIS METHODS AND PRODUCTS

(71) Applicant: The Coca-Cola Company, Atlanta, GA (US)

(72) Inventors: Indra Prakash, Alpharetta, GA (US); Gil Ma, Atlanta, GA (US); Christopher Mercogliano, Atlanta, GA (US); Carol Hartley, Acton (AU); Matthew Alexander Wilding, Acton (AU); Colin Scott, Acton (AU)

(73) Assignee: The Coca-Cola Company, Atlanta, GA (US)

( * ) Notice: Subject to any disclaimer, the term of this patent is extended or adjusted under 35 U.S.C. 154(b) by 751 days.

(21) Appl. No.: 17/434,234

(22) PCT Filed: Feb. 26, 2020

(86) PCT No.: PCT/US2020/019972
§ 371 (c)(1),
(2) Date: Aug. 26, 2021

(87) PCT Pub. No.: WO2020/176668
PCT Pub. Date: Sep. 3, 2020

(65) Prior Publication Data
US 2022/0205010 A1 Jun. 30, 2022

Related U.S. Application Data

(60) Provisional application No. 62/810,553, filed on Feb. 26, 2019.

(51) Int. Cl.
*C12P 33/00* (2006.01)
*C07J 17/00* (2006.01)

(52) U.S. Cl.
CPC ............. *C12P 33/00* (2013.01); *C07J 17/005* (2013.01); *C12Y 302/01023* (2013.01)

(58) Field of Classification Search
CPC .. C12P 33/00; C12Y 302/01023; C07J 17/005
See application file for complete search history.

(56) References Cited

U.S. PATENT DOCUMENTS 11,060,124 B2 * 7/2021 Patron ................. C12N 9/0042
2012/0059071 A1   3/2012 Markosyan et al.
(Continued)

FOREIGN PATENT DOCUMENTS

WO   WO 2014-150127    9/2014
WO   WO 2017/202997    11/2017

OTHER PUBLICATIONS

International Search Report for PCT/US2020/019972, issued Jun. 25, 2020.
(Continued)

*Primary Examiner* — Anthony J Weier
(74) *Attorney, Agent, or Firm* — King & Spalding LLP

(57) ABSTRACT

Monk fruit extracts containing mogrol glycosides such as mogroside V may be treated with enzymes under specific reaction conditions to shift distribution of the Siamenoside I reaction product. Modified enzymes are also employed to shift Siamenoside I distribution to increase yield of Siamenoside I and reduce reaction contaminants. Methods of purifying bioconversion reaction product are also described. Siamenoside I obtained using these methods is a useful sweetener and flavor enhancer for food and beverage compositions and the like.

7 Claims, 18 Drawing Sheets
Specification includes a Sequence Listing.

(56) References Cited

U.S. PATENT DOCUMENTS

| | | | |
|---|---|---|---|
| 2014/0343262 A1 | 11/2014 | Prakash et al. | |
| 2017/0119032 A1* | 5/2017 | Patron | A23L 27/204 |
| 2018/0155699 A1* | 6/2018 | Kim | C12N 15/75 |
| 2019/0071705 A1* | 3/2019 | Patron | C12Y 302/01006 |
| 2021/0227863 A1* | 7/2021 | Patron | A23L 27/00 |
| 2021/0324439 A1* | 10/2021 | Patron | C12N 9/0042 |
| 2024/0108040 A1* | 4/2024 | Patron | A23L 2/52 |

OTHER PUBLICATIONS

Chiu, C. H. et al., "Biotransformation of Mogrosides from Siraitia grosvenorii Swingle by Saccharo-myces cerevisiae", Journal of agricultural and food chemistry, 2013, vol. 61, pp. 7127-7134.

NCBI, GenBank accession No. XP_001727461.1, "unnamed protein product [Aspergillus oryzae RIB40]" Apr. 4, 2018.

Wang Reuben et al: "Dekkera bruxellensis, a beer yeast that specifically bioconverts mogroside extracts into the intense natural sweetener siamenoside I", Food Chemistry, Elsevier LTD, NL, vol. 276, Sep. 29, 2018 (Sep. 29, 2018), pp. 43-49.

"beta-galactosidase E [Aspergillus bombycis] GenBank: OGM48583.1", NCBI, NCBI database, pp. 1-2.

"beta-galactosidase E, partial [Aspergillus nomiae NRRL 13137] GenBank: KNG88284.1", NCBI, NCBI database, pp. 1-2.

"putative beta-galactosidase A [Aspergillus steynii IBT 23096] GenBank: PLB48376.1", NCBI, NCBI database, pp. 1-2.

"putative beta-galactosidase A [Aspergillus cristatus] GenBank: ODM18685.1", NCBI, NCBI database, pp. 1-2.

\* cited by examiner

FIG. 4

| gBlock ID numbers | gBlock Gene Fragment | Length (bp) | Restriction Enzyme Sites For Cloning | Amino acid variants encoded by this fragment | | | | |
|---|---|---|---|---|---|---|---|---|
| | | | | E142 | E200 | D258 | E298 | E804 |
| 100480359 | AoBG Eco-Kpn front | 1101 | Eco R1, Kpn I | E | E | D | E | |
| 100480360 | AoBG Kpn-SacII back | 2015 | Kpn I, Sac II | | | | | E |
| 100481315 | Eco-Pst E142Q | 579 | Eco R1, Pst I | Q | | | | |
| 100481320 | Eco-Pst E142A | 579 | Eco R1, Pst I | A | | | | |
| 100481316 | Pst-Kpn D258Q | 530 | Pst I, Kpn I | | E | Q | E | E |
| 100481317 | Pst-Kpn D258A | 530 | Pst I, Kpn I | | E | A | E | E |
| 100481318 | Pst-Kpn E200A | 530 | Pst I, Kpn I | | A | D | E | E |
| 100481321 | Pst-Kpn E200Q | 530 | Pst I, Kpn I | | Q | D | A | E |
| 100481319 | Pst-Kpn E200298A | 530 | Pst I, Kpn I | | A | D | A | E |
| 100481322 | Pst-Kpn E200298Q | 530 | Pst I, Kpn I | | Q | D | Q | E |
| 100481396 | Kpn-SacII E804Q | 2015 | Kpn I, Sac II | | | | | Q |
| 100481397 | Kpn-SacII E804A | 2015 | Kpn I, Sac II | | | | | A |
| 100681258 | Pst-Kpn E298Q | 530 | Pst I, Kpn I | | E | D | Q | |
| 100681260 | Pst-Kpn E298A | 530 | Pst I, Kpn I | | E | D | A | |
| 100681259 | Pst-Kpn D258AE298A | 530 | Pst I, Kpn I | | E | A | A | |

SEQUENCE LISTING

<160> NUMBER OF SEQ ID NOS: 9

<210> SEQ ID NO 1
<211> LENGTH: 1005
<212> TYPE: PRT
<213> ORGANISM: Aspergillus oryzae

<400> SEQUENCE: 1

Met Lys Leu Leu Ser Val Ala Ala Val Ala Leu Leu Ala Ala Gln Ala
1               5                   10                  15

Ala Gly Ala Ser Ile Lys His Arg Leu Asn Gly Phe Thr Ile Leu Glu
            20                  25                  30

His Pro Asp Pro Ala Lys Arg Asp Leu Leu Gln Asp Ile Val Thr Trp
        35                  40                  45

```
Asp Asp Lys Ser Leu Phe Ile Asn Gly Glu Arg Ile Met Leu Phe Ser
 50                  55                  60

Gly Glu Val His Pro Phe Arg Leu Pro Val Pro Ser Leu Trp Leu Asp
 65                  70                  75                  80

Ile Phe His Lys Ile Arg Ala Leu Gly Phe Asn Cys Val Ser Phe Tyr
                 85                  90                  95

Ile Asp Trp Ala Leu Leu Glu Gly Lys Pro Gly Asp Tyr Arg Ala Glu
                100                 105                 110

Gly Ile Phe Ala Leu Glu Pro Phe Phe Asp Ala Ala Lys Glu Ala Gly
            115                 120                 125

Ile Tyr Leu Ile Ala Arg Pro Gly Ser Tyr Ile Asn Ala Glu Val Ser
    130                 135                 140

Gly Gly Gly Phe Pro Gly Trp Leu Gln Arg Val Asn Gly Thr Leu Arg
145                 150                 155                 160

Ser Ser Asp Glu Pro Phe Leu Lys Ala Thr Asp Asn Tyr Ile Ala Asn
                165                 170                 175

Ala Ala Ala Ala Val Ala Lys Ala Gln Ile Thr Asn Gly Gly Pro Val
                180                 185                 190

Ile Leu Tyr Gln Pro Glu Asn Glu Tyr Ser Gly Gly Cys Cys Gly Val
            195                 200                 205

Lys Tyr Pro Asp Ala Asp Tyr Met Gln Tyr Val Met Asp Gln Ala Arg
    210                 215                 220

Lys Ala Asp Ile Val Val Pro Phe Ile Ser Asn Asp Ala Ser Pro Ser
225                 230                 235                 240

Gly His Asn Ala Pro Gly Ser Gly Thr Gly Ala Val Asp Ile Tyr Gly
                245                 250                 255

His Asp Ser Tyr Pro Leu Gly Phe Asp Cys Ala Asn Pro Ser Val Trp
                260                 265                 270

Pro Glu Gly Lys Leu Pro Asp Asn Phe Arg Thr Leu His Leu Glu Gln
            275                 280                 285

Ser Pro Ser Thr Pro Tyr Ser Leu Leu Glu Phe Gln Ala Gly Ala Phe
    290                 295                 300

Asp Pro Trp Gly Gly Pro Gly Phe Glu Lys Cys Tyr Ala Leu Val Asn
305                 310                 315                 320

His Glu Phe Ser Arg Val Phe Tyr Arg Asn Asp Leu Ser Phe Gly Val
                325                 330                 335

Ser Thr Phe Asn Leu Tyr Met Thr Phe Gly Gly Thr Asn Trp Gly Asn
                340                 345                 350

Leu Gly His Pro Gly Gly Tyr Thr Ser Tyr Asp Tyr Gly Ser Pro Ile
            355                 360                 365

Thr Glu Thr Arg Asn Val Thr Arg Glu Lys Tyr Ser Asp Ile Lys Leu
    370                 375                 380

Leu Ala Asn Phe Val Lys Ala Ser Pro Ser Tyr Leu Thr Ala Thr Pro
385                 390                 395                 400

Arg Asn Leu Thr Thr Gly Val Tyr Thr Asp Thr Ser Asp Leu Ala Val
                405                 410                 415

Thr Pro Leu Ile Gly Asp Ser Pro Gly Ser Phe Phe Val Val Arg His
                420                 425                 430

Thr Asp Tyr Ser Ser Gln Glu Ser Thr Ser Tyr Lys Leu Lys Leu Pro
            435                 440                 445

Thr Ser Ala Gly Asn Leu Thr Ile Pro Gln Leu Glu Gly Thr Leu Ser
    450                 455                 460
```

-continued

```
Leu Asn Gly Arg Asp Ser Lys Ile His Val Asp Tyr Asn Val Ser
465                 470                 475                 480

Gly Thr Asn Ile Ile Tyr Ser Thr Ala Glu Val Phe Thr Trp Lys Lys
                485                 490                 495

Phe Asp Gly Asn Lys Val Leu Val Leu Tyr Gly Gly Pro Lys Glu His
                500                 505                 510

His Glu Leu Ala Ile Ala Ser Lys Ser Asn Val Thr Ile Ile Glu Gly
                515                 520                 525

Ser Asp Ser Gly Ile Val Ser Thr Arg Lys Gly Ser Ser Val Ile Ile
530                 535                 540

Gly Trp Asp Val Ser Ser Thr Arg Arg Ile Val Gln Val Gly Asp Leu
545                 550                 555                 560

Arg Val Phe Leu Leu Asp Arg Asn Ser Ala Tyr Asn Tyr Trp Val Pro
                565                 570                 575

Glu Leu Pro Thr Glu Gly Thr Ser Pro Gly Phe Ser Thr Ser Lys Thr
                580                 585                 590

Thr Ala Ser Ser Ile Ile Val Lys Ala Gly Tyr Leu Leu Arg Gly Ala
                595                 600                 605

His Leu Asp Gly Ala Asp Leu His Leu Thr Ala Asp Phe Asn Ala Thr
                610                 615                 620

Thr Pro Ile Glu Val Ile Gly Ala Pro Thr Gly Ala Lys Asn Leu Phe
625                 630                 635                 640

Val Asn Gly Glu Lys Ala Ser His Thr Val Asp Lys Asn Gly Ile Trp
                645                 650                 655

Ser Ser Glu Val Lys Tyr Ala Ala Pro Glu Ile Lys Leu Pro Gly Leu
                660                 665                 670

Lys Asp Leu Asp Trp Lys Tyr Leu Asp Thr Leu Pro Glu Ile Lys Ser
                675                 680                 685

Ser Tyr Asp Asp Ser Ala Trp Val Ser Ala Asp Leu Pro Lys Thr Lys
                690                 695                 700

Asn Thr His Arg Pro Leu Asp Thr Pro Thr Ser Leu Tyr Ser Ser Asp
705                 710                 715                 720

Tyr Gly Phe His Thr Gly Tyr Leu Ile Tyr Arg Gly His Phe Val Ala
                725                 730                 735

Asn Gly Lys Glu Ser Glu Phe Phe Ile Arg Thr Gln Gly Gly Ser Ala
                740                 745                 750

Phe Gly Ser Ser Val Trp Leu Asn Glu Thr Tyr Leu Gly Ser Trp Thr
                755                 760                 765

Gly Ala Asp Tyr Ala Met Asp Gly Asn Ser Thr Tyr Lys Leu Ser Gln
770                 775                 780

Leu Glu Ser Gly Lys Asn Tyr Val Ile Thr Val Ile Asp Asn Leu
785                 790                 795                 800

Gly Leu Asp Glu Asn Trp Thr Val Gly Glu Glu Thr Met Lys Asn Pro
                805                 810                 815

Arg Gly Ile Leu Ser Tyr Lys Leu Ser Gly Gln Asp Ala Ser Ala Ile
                820                 825                 830

Thr Trp Lys Leu Thr Gly Asn Leu Gly Gly Glu Asp Tyr Gln Asp Lys
                835                 840                 845

Val Arg Gly Pro Leu Asn Glu Gly Gly Leu Tyr Ala Glu Arg Gln Gly
                850                 855                 860

Phe His Gln Pro Gln Pro Ser Glu Ser Trp Glu Ser Gly Ser Pro
865                 870                 875                 880

Leu Glu Gly Leu Ser Lys Pro Gly Ile Gly Phe Tyr Thr Ala Gln Phe
```

```
                    885                 890                 895
Asp Leu Asp Leu Pro Lys Gly Trp Asp Val Pro Leu Tyr Phe Asn Phe
            900                 905                 910

Gly Asn Asn Thr Gln Ala Ala Arg Ala Gln Leu Tyr Val Asn Gly Tyr
            915                 920                 925

Gln Tyr Gly Lys Phe Thr Gly Asn Val Gly Pro Gln Thr Ser Phe Pro
            930                 935                 940

Val Pro Glu Gly Ile Leu Asn Tyr Arg Gly Thr Asn Tyr Val Ala Leu
945                 950                 955                 960

Ser Leu Trp Ala Leu Glu Ser Asp Gly Ala Lys Leu Gly Ser Phe Glu
            965                 970                 975

Leu Ser Tyr Thr Thr Pro Val Leu Thr Gly Tyr Gly Asn Val Glu Ser
            980                 985                 990

Pro Glu Gln Pro Lys Tyr Glu Gln Arg Lys Gly Ala Tyr
            995                1000                1005

<210> SEQ ID NO 2
<211> LENGTH: 1036
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Lys Leu Leu Ser Val Ala Val Ala Leu Leu Ala Ala Gln Ala
1               5                  10                  15

Ala Gly Ala Ser Ile Lys His Arg Leu Asn Gly Phe Thr Ile Leu Glu
            20                  25                  30

His Pro Asp Pro Ala Lys Arg Asp Leu Leu Gln Asp Ile Val Thr Trp
        35                  40                  45

Asp Asp Lys Ser Leu Phe Ile Asn Gly Glu Arg Ile Met Leu Phe Ser
    50                  55                  60

Gly Glu Val His Pro Phe Arg Leu Pro Val Pro Ser Leu Trp Leu Asp
65                  70                  75                  80

Ile Phe His Lys Ile Arg Ala Leu Gly Phe Asn Cys Val Ser Phe Tyr
                85                  90                  95

Ile Asp Trp Ala Leu Leu Glu Gly Lys Pro Gly Asp Tyr Arg Ala Glu
            100                 105                 110

Gly Ile Phe Ala Leu Glu Pro Phe Phe Asp Ala Ala Lys Glu Ala Gly
        115                 120                 125

Ile Tyr Leu Ile Ala Arg Pro Gly Ser Tyr Ile Asn Ala Glu Val Ser
    130                 135                 140

Gly Gly Gly Phe Pro Gly Trp Leu Gln Arg Val Asn Gly Thr Leu Arg
145                 150                 155                 160

Ser Ser Asp Glu Pro Phe Leu Lys Ala Thr Asp Asn Tyr Ile Ala Asn
                165                 170                 175

Ala Ala Ala Ala Val Ala Lys Ala Gln Ile Thr Asn Gly Gly Pro Val
            180                 185                 190

Ile Leu Tyr Gln Pro Glu Asn Glu Tyr Ser Gly Gly Cys Cys Gly Val
        195                 200                 205

Lys Tyr Pro Asp Ala Asp Tyr Met Gln Tyr Val Met Asp Gln Ala Arg
    210                 215                 220

Lys Ala Asp Ile Val Val Pro Phe Ile Ser Asn Asp Ala Ser Pro Ser
225                 230                 235                 240
```

```
Gly His Asn Ala Pro Gly Ser Gly Thr Gly Ala Val Asp Ile Tyr Gly
                245                 250                 255

His Asp Ser Tyr Pro Leu Gly Phe Asp Cys Ala Asn Pro Ser Val Trp
            260                 265                 270

Pro Glu Gly Lys Leu Pro Asp Asn Phe Arg Thr Leu His Leu Glu Gln
            275                 280                 285

Ser Pro Ser Thr Pro Tyr Ser Leu Leu Glu Phe Gln Ala Gly Ala Phe
        290                 295                 300

Asp Pro Trp Gly Gly Pro Gly Phe Glu Lys Cys Tyr Ala Leu Val Asn
305                 310                 315                 320

His Glu Phe Ser Arg Val Phe Tyr Arg Asn Asp Leu Ser Phe Gly Val
                325                 330                 335

Ser Thr Phe Asn Leu Tyr Met Thr Phe Gly Gly Thr Asn Trp Gly Asn
            340                 345                 350

Leu Gly His Pro Gly Gly Tyr Thr Ser Tyr Asp Tyr Gly Ser Pro Ile
        355                 360                 365

Thr Glu Thr Arg Asn Val Thr Arg Glu Lys Tyr Ser Asp Ile Lys Leu
    370                 375                 380

Leu Ala Asn Phe Val Lys Ala Ser Pro Ser Tyr Leu Thr Ala Thr Pro
385                 390                 395                 400

Arg Asn Leu Thr Thr Gly Val Tyr Thr Asp Thr Ser Asp Leu Ala Val
                405                 410                 415

Thr Pro Leu Ile Gly Asp Ser Pro Gly Ser Phe Val Val Arg His
            420                 425                 430

Thr Asp Tyr Ser Ser Gln Glu Ser Thr Ser Tyr Lys Leu Lys Leu Pro
        435                 440                 445

Thr Ser Ala Gly Asn Leu Thr Ile Pro Gln Leu Glu Gly Thr Leu Ser
    450                 455                 460

Leu Asn Gly Arg Asp Ser Lys Ile His Val Val Asp Tyr Asn Val Ser
465                 470                 475                 480

Gly Thr Asn Ile Ile Tyr Ser Thr Ala Glu Val Phe Thr Trp Lys Lys
                485                 490                 495

Phe Asp Gly Asn Lys Val Leu Val Leu Tyr Gly Gly Pro Lys Glu His
            500                 505                 510

His Glu Leu Ala Ile Ala Ser Lys Ser Asn Val Thr Ile Ile Glu Gly
            515                 520                 525

Ser Asp Ser Gly Ile Val Ser Thr Arg Lys Gly Ser Ser Val Ile Ile
        530                 535                 540

Gly Trp Asp Val Ser Ser Thr Arg Arg Ile Val Gln Val Gly Asp Leu
545                 550                 555                 560

Arg Val Phe Leu Leu Asp Arg Asn Ser Ala Tyr Asn Tyr Trp Val Pro
                565                 570                 575

Glu Leu Pro Thr Glu Gly Thr Ser Pro Gly Phe Ser Thr Ser Lys Thr
            580                 585                 590

Thr Ala Ser Ser Ile Ile Val Lys Ala Gly Tyr Leu Leu Arg Gly Ala
        595                 600                 605

His Leu Asp Gly Ala Asp Leu His Leu Thr Ala Asp Phe Asn Ala Thr
    610                 615                 620

Thr Pro Ile Glu Val Ile Gly Ala Pro Thr Gly Ala Lys Asn Leu Phe
625                 630                 635                 640

Val Asn Gly Glu Lys Ala Ser His Thr Val Asp Lys Asn Gly Ile Trp
                645                 650                 655

Ser Ser Glu Val Lys Tyr Ala Ala Pro Glu Ile Lys Leu Pro Gly Leu
```

Lys Asp Leu Asp Trp Lys Tyr Leu Asp Thr Leu Pro Glu Ile Lys Ser
675                 680                 685

Ser Tyr Asp Asp Ser Ala Trp Val Ser Ala Asp Leu Pro Lys Thr Lys
        690                 695                 700

Asn Thr His Arg Pro Leu Asp Thr Pro Thr Ser Leu Tyr Ser Ser Asp
705                 710                 715                 720

Tyr Gly Phe His Thr Gly Tyr Leu Ile Tyr Arg Gly His Phe Val Ala
                725                 730                 735

Asn Gly Lys Glu Ser Glu Phe Phe Ile Arg Thr Gln Gly Gly Ser Ala
            740                 745                 750

Phe Gly Ser Ser Val Trp Leu Asn Glu Thr Tyr Leu Gly Ser Trp Thr
        755                 760                 765

Gly Ala Asp Tyr Ala Met Asp Gly Asn Ser Thr Tyr Lys Leu Ser Gln
770                 775                 780

Leu Glu Ser Gly Lys Asn Tyr Val Ile Thr Val Ile Asp Asn Leu
785                 790                 795                 800

Gly Leu Asp Glu Asn Trp Thr Val Gly Glu Thr Met Lys Asn Pro
                805                 810                 815

Arg Gly Ile Leu Ser Tyr Lys Leu Ser Gly Gln Asp Ala Ser Ala Ile
            820                 825                 830

Thr Trp Lys Leu Thr Gly Asn Leu Gly Gly Asp Tyr Gln Asp Lys
        835                 840                 845

Val Arg Gly Pro Leu Asn Glu Gly Gly Leu Tyr Ala Glu Arg Gln Gly
850                 855                 860

Phe His Gln Pro Gln Pro Pro Ser Glu Ser Trp Glu Ser Gly Ser Pro
865                 870                 875                 880

Leu Glu Gly Leu Ser Lys Pro Gly Ile Gly Phe Tyr Thr Ala Gln Phe
                885                 890                 895

Asp Leu Asp Leu Pro Lys Gly Trp Asp Val Pro Leu Tyr Phe Asn Phe
            900                 905                 910

Gly Asn Asn Thr Gln Ala Ala Arg Ala Gln Leu Tyr Val Asn Gly Tyr
        915                 920                 925

Gln Tyr Gly Lys Phe Thr Gly Asn Val Gly Pro Gln Thr Ser Phe Pro
930                 935                 940

Val Pro Glu Gly Ile Leu Asn Tyr Arg Gly Thr Asn Tyr Val Ala Leu
945                 950                 955                 960

Ser Leu Trp Ala Leu Glu Ser Asp Gly Ala Lys Leu Gly Ser Phe Glu
                965                 970                 975

Leu Ser Tyr Thr Thr Pro Val Leu Thr Gly Tyr Gly Asn Val Glu Ser
            980                 985                 990

Pro Glu Gln Pro Lys Tyr Glu Gln Arg Lys Gly Ala Tyr Leu Glu Ala
        995                 1000                1005

Ala Ala Ala Ala Ser Phe Leu Glu Gln Lys Leu Ile Ser Glu Glu
1010                1015                1020

Asp Leu Asn Ser Ala Val Asp His His His His His His
        1025                1030                1035

<210> SEQ ID NO 3
<211> LENGTH: 3111
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 3

```
atgaagttgt tgtctgttgc tgccgttgct ttgttggctg ctcaagctgc tggtgcttct      60
atcaaacata gattgaacgg tttcaccatc ttggaacatc cagatccagc taaaagagat     120
ttgttgcaag atatcgttac ctgggatgac aagtccttgt ttattaacgg tgaaaggatc     180
atgttgttct ccggtgaagt tcatcctttt agattgccag ttccatcttt gtggttggac     240
attttccaca aaattagagc cttgggtttc aactgcgttt ccttttacat tgattgggcc     300
ttgttggaag gtaaaccagg tgattataga gccgaaggta ttttgctttt ggaaccattt     360
ttcgatgctg ctaaagaagc tggtatctac ttgattgcta gaccaggttc ttacattaac     420
gctcaggttt ctggtggtgg ttttccaggt tggttgcaaa gagttaacgg tactttgaga     480
tcttccgatg aaccattctt gaaggctacc gataattaca ttgctaatgc tgctgctgca     540
gttgctaaag ctcaaattac taatggtggt ccagtcatct tgtaccaacc agaaaatcag     600
tactctggtg ttgttgtgg tgttaagtat ccagatgctg attacatgca atacgttatg     660
gatcaagcta gaaaggccga tatcgttgtt ccattcattt ctaatgatgc ctctccatct     720
ggtcataatg ctccaggttc tggtactggt gctgttgata tctatggtca tcagtcttac     780
ccattgggtt tcgattgtgc taatccatct gtttggccag aaggtaaatt gccagataat     840
ttcagaacct gcacttgga acaatctcca tctactccat actcgttgtt gcagtttcaa     900
gctggtgcat tgatccatg gggtggtcct ggttttgaaa atgttatgc cttggtcaac     960
cacgagttct ctagagtttt ttacagaaac gacttgtcct tcggtgtttc tactttcaac    1020
ttgtacatga ctttcggtgg taccaattgg ggtaatttgg gtcatccagg tggttacaca    1080
tcttatgatt atggttctcc aatcaccgaa accagaaatg ttactaggga aaagtactcc    1140
gacattaagt tgttggctaa cttcgttaag gcttccccat cttatttgac tgctactcca    1200
agaaatttga ccactggtgt ctatactgat acctctgatt tggctgttac tccattgata    1260
ggtgattcac caggttcatt cttcgttgtt agacataccg attactcctc tcaagaatct    1320
acctcctaca aattgaagtt gcctacttct gctggtaact tgactattcc acaactagaa    1380
ggtacgctgt ctttgaatgg tagagattcc aaaatccacg ttgtcgacta taacgttct     1440
ggcactaaca ttatctactc tactgccgaa gttttcacct ggaagaaatt cgatggtaac    1500
aaggttttgg tcttgtacgg tggtccaaaa gaacatcatg aattggctat tgcctccaag    1560
tctaacgtta ctattatcga aggttccgac tctggtatcg tttctactag aaaaggttcc    1620
tccgttatta tcggttggga tgtttcttct accagaagaa tcgttcaagt tggtgacttg    1680
agagtttttct tgttggatag aaactccgct tacaattact gggttccaga attgcctact    1740
gaaggtactt ctccaggttt ttctacttct aagactaccg cctcttccat tattgtcaaa    1800
gctggttatt tgttgagagg tgctcatttg gatggtgctg acttgcattt gacagctgat    1860
tttaatgcta ctaccccaat cgaagttatt ggtgctccaa ctggtgctaa gaatttgttc    1920
gttaatggtg aaaaggcctc tcacactgtt gataagaatg gtatttggtc tccgaagtt    1980
aagtatgctg ctccagaaat caaattgcct ggtttgaaag atttggactg gaagtacttg    2040
gataccctgc ctgaaatcaa aagctcttat gatgattctg catgggtttc tgctgatttg    2100
ccaaagacta gaataccca tagacctttg gatactccaa cctccttgta ttcttctgat    2160
tacggttttc ataccggcta cttgatctac agaggtcatt ttgttgctaa cggtaaagag    2220
tccgagttct tcattagaac tcaaggtggt tctgctttcg gttcttctgt tggttgaac     2280
```

-continued

```
gaaacttact taggttcttg dacaggtgct gattatgcta tggatggtaa ttctacctac    2340
aagttgtccc aattggaatc cggtaagaac tacgttatta ccgttgtcat cgacaacttg    2400
ggtttagacg aaaattggac tgttggtgaa gaaaccatga agaacccaag aggtatcttg    2460
tcctataagt tgtctggtca agatgcttct gctattactt ggaagttgac aggtaactta    2520
ggtggtgaag attaccaaga taaggttaga ggtccattga atgaaggtgg tctatatgct    2580
gaaagacaag gtttccatca accacaacct ccatctgaat cttgggaatc tggttcacca    2640
ttggaaggtt tgtctaaacc tggtattggt ttctacactg cccaattcga tttggatttg    2700
cctaaaggtt gggacgttcc attatacttc aactttggta acaatacccca agctgctaga    2760 gcccaattat atgttaatgg ttatcagtac ggcaagttca ctggtaatgt tggtccacaa    2820
acatcttttc cagtacctga gggtattttg aattacagag gtacaaatta cgtcgccttg    2880
tcattgtggg ctttagaatc tgatggtgct aaattgggtt ccttcgaatt gtcttatacc    2940
actccagttt tgactggtta cggtaacgtt gaatctccag aacaacctaa atacgaacaa    3000
agaaagggtg cctacctcga ggccgcggcg gccgccagct ttctagaaca aaaactcatc    3060
tcagaagagg atctgaatag cgccgtcgac catcatcatc atcatcattg a            3111
```

```
<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gctcgaattc atgaagttgt tgtctgttgc tgccg                              35

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aagcttggat ccttaatagg cacctttacg                                    30

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tagattgaac ggtttcacca                                               20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcaatggagt aacagccaaa                                               20
```

```
<210> SEQ ID NO 8
<211> LENGTH: 1101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
gtgctcgaat tcatgaagtt gttgtctgtt gctgccgttg ctttgttggc tgctcaagct      60
gctggtgctt ctatcaaaca tagattgaac ggtttcacca tcttggaaca tccagatcca     120
gctaaaagag atttgttgca agatatcgtt acctgggatg acaagtcctt gtttattaac     180
ggtgaaagga tcatgttgtt ctccggtgaa gttcatcctt ttagattgcc agttccatct     240
ttgtggttgg acatttccaa caaaattaga gccttgggtt tcaactgcgt ttccttttac     300
attgattggg ccttgttgga aggtaaacca ggtgattata gagccgaagg tattttgct      360 ttggaaccat ttttcgatgc tgctaaagaa gctggtatct acttgattgc tagaccaggt     420
tcttacatta acgctgaagt ttctggtggt ggttttccag gttggttgca aagagttaac     480
ggtactttga gatcttccga tgaaccattc ttgaaggcta ccgataatta cattgctaat     540
gctgctgctg cagttgctaa agctcaaatt actaatggtg gtccagtcat cttgtaccaa     600
ccagaaaatg aatactctgg trrkrrktgt ggtrrkaagt atccagatgc tgattacatg     660
caatacgtta tggatcaagc tagaaaggcc gatatcgttg ttccattcat ttctaatgat     720
gcctctccat ctggtcataa tgctccaggt tctggtactg gtgctgttga tatctatggt     780
catgattctt acccattggg tttcgattgt gctaatccat ctgtttggcc agaaggtaaa     840
ttgccagata atttcagaac cttgcacttg gaacaatctc catctactcc atactcgttg     900
ttggaatttc aagctggtgc atttgatcca tggggtggtc ctggttttga aaaatgttat     960
gccttggtca accacgagtt ctctagagtt ttttacagaa acgacttgtc cttcggtgtt    1020
tctactttca acttgtacat gactttcggt ggtaccaatt ggggtaattt gggtcatcca    1080
ggtggttaca catcttatga t                                              1101

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 9

His His His His His His
1               5
```

MOGROSIDE BIOCATALYSIS METHODS AND PRODUCTS

CROSS REFERENCE TO RELATED APPLICATIONS

This application is a national phase application under 35 U.S.C. § 371 of International Application No. PCT/US2020/019972, filed Feb. 26, 2020, which claims priority to U.S. Provisional Application No. 62/810,553, filed Feb. 26, 2019. The contents of each of the above-identified applications is hereby fully incorporated herein by reference.

REFERENCE TO THE SEQUENCE LISTING

The instant application contains a Sequence Listing which has been submitted electronically in ASCII format and is hereby incorporated by reference in its entirety. Said ASCII copy, created on Mar. 8, 2022, is named 12600 105185 US SL.txt and is 24,855 bytes in size.

SEQ ID NO:1: amino acid sequence of wild-type *Aspergillus oryza* beta-galactosidase.

SEQ ID NO:2: amino acid sequence of wild-type *Aspergillus oryza* beta-glactosidase fusion protein sequence as secreted by *P. pastoris* cells with a myc and hexa-histidine tag sequence (SEQ ID NO: 9).

SEQ ID NO: 3: nucleic acid sequence of the amino acid sequence of SEQ ID NO: 2.

SEQ ID NO: 4: the nucleic acid sequence of the AoBG-F-Eco primer.

SEQ ID NO: 5: the nucleic acid sequence of the AoBG-R primer.

SEQ ID NO: 6: the nucleic acid sequence of the AoBG-inner-F primer.

SEQ ID NO: 7: the nucleic acid sequence of the AoBG-Kpn-R primer.

SEQ ID NO: 8: an amplified nucleic acid sequence.

FIELD

The disclosure relates to methods useful for producing Siamenoside I from a monk fruit extract. More specifically, the disclosure relates to methods useful for producing high purity Siamenoside I from Mogroside V by biotransformation and purification, as well as enzymes used therein. Also disclosed are sweetener compositions comprising high purity Siamenoside I, as well as food and beverage containing the same.

BACKGROUND

Extracts of monk fruit obtained from *Siraitia grosvenori* (a plant of the Cucurbitaceae family) are commercially used as natural sweeteners. Yet, monk fruit extract may have taste characteristics that discourage their use as a replacement for caloric sweeteners (e.g., sugar) in food and beverage compositions. For example, the extracts may have certain off-flavors or a lingering aftertaste or may take longer than desired to develop a sweet taste after being consumed (i.e., a delayed onset of sweetness).

There remains a need for sweeteners with reduced calorie content having low or no calories having improved taste characteristics, as well as food and beverages containing the same.

SUMMARY

In one aspect, a method is disclosed for producing Siamenoside I comprising:

a) combining a solution comprising mogroside V with an effective amount of a beta-galactosidase enzyme at a suitable pH and a suitable temperature to provide a beta-galactosidase/mogroside V solution;

b) incubating the beta-galactosidase/mogroside V solution for a suitable time to provide a solution comprising Siamenoside I; and c) purifying Siamenoside I from the solution comprising Siamenoside I, wherein the Siamenoside I has greater than about 90% purity.

In one embodiment, the Siamenoside I produced from step b) has a yield greater than 60%.

In one embodiment, the Siamenoside I purified from step c) is greater than 97% purity.

In one embodiment, the Siamenoside I purified from step c) is greater than 99% purity.

In one embodiment, the suitable temperature is between about 45 and about 60° C. and the suitable pH is between about 6.1 and about 7.0.

In one embodiment, the suitable temperature is between about 50 and about 60° C. and the suitable pH is between about 6.1 and about 7.0.

In one embodiment, the suitable temperature is between about 50 and about 55° C. and the suitable pH is between about 6.1 and about 7.0.

In one embodiment, the suitable temperature is between about 50 and about 55° C. and the suitable pH is between 6.3 and 7.0.

In one embodiment, the suitable temperature is between about 50 and about 55° C. and the suitable pH is between about 6.5 and about 7.0.

In one embodiment, the suitable temperature is between about 50 and about 55° C. and the suitable pH is between about 6.8 and about 7.0.

In one embodiment, the incubation step b) produces a Siamenoside I yield greater than 60%. In certain embodiments, the yield of Siamenoside I is greater than about 65%, greater than about 70%, greater than about 75%, greater than about 80%, greater than about 85%, greater than about 90%, or greater than about 95%.

In one embodiment, the purification step c) produces Siamenoside I with a purity greater than 90%. In certain embodiments, the purity of Siamenoside I is greater than about 90%, greater than about 95%, or greater than about 99%.

In one embodiment, compared to conventional methods, the method disclosed herein increases the purity of Siamenoside I produced. In certain embodiments, the purity is increased by about 10%, about 20%, about 30%, about 40% or about 50% or more compared to the purity of Siamenoside I produced by conventional methods.

In one embodiment, the method produces Siamenoside I with a purity between about 60% and about 90% purity.

In one embodiment, the method produces Siamenoside I with a purity between about 60% and about 95% purity.

In one embodiment, the method produces Siamenoside I with a purity between about 65% and about 90% purity.

In one embodiment, the method produces Siamenoside I with a purity between about 65% and about 95% purity.

In one embodiment, the method produces Siamenoside I with a purity between about 70% and about 90% purity.

In one embodiment, the method produces Siamenoside I with a purity between about 70% and about 95% purity.

In one embodiment, the method produces Siamenoside I with a purity between about 75% and about 90%.

In one embodiment, the method produces Siamenoside I with a purity between about 75% and about 95%.

In one embodiment, the beta-galactosidase enzyme is a wild-type *Aspergillus oryzae* beta-galactosidase (AoBG) or a variant thereof.

In a particular embodiment, the beta-galactosidase enzyme is a variant of a wild-type AoBG having at least 50% identity to the AoBG, e.g. at least 60% identity, at least 70% identity, at least 80% identity or at least 90% identity to the wild-type AoGB.

In a particular embodiment, the beta-galactosidase enzyme comprises the amino acid sequence of SEQ ID. NO:1 or a variant thereof. In one embodiment, the variant has at least 50% identity, at least 60% identity, at least 70% identity, at least 80% identity or at least 90% identity to SEQ ID NO: 1.

In another particular embodiment, the beta-galactosidase enzyme comprises the amino acid sequence of SEQ ID. NO:2 or a variant thereof. In one embodiment, the variant has at least 50% identity, at least 60% identity, at least 70% identity, at least 80% identity or at least 90% identity to SEQ ID NO: 2.

In one embodiment, the method increases the conversion rate for Siamenoside I from mogroside V compared to conventional methods. In certain embodiments, the conversion rate is increased by about 10%, about 20%, about 30%, about 40% or about 50% or more compared to the conversion rate of Siamenoside I produced by conventional methods.

In a second aspect, a modified beta-galactosidase enzyme is disclosed comprising one or more mutations in the catalytic site or loop region.

In one embodiment, the modified beta-galactosidase enzyme has at least 50% identity, at least 60% identity, at least 70% identity, at least 80% identity or at least 90% identity to SEQ ID NO: 1.

In another embodiment, the modified beta-galactosidase enzyme has at least 50% identity, at least 60% identity, at least 70% identity, at least 80% identity or at least 90% identity to SEQ ID NO: 2.

In one embodiment, the one or more mutations comprise at least one substitution of an amino acid residue corresponding to any of amino acids 142, 204, 205 or 208 of SEQ ID NO: 1.

In one embodiment, the one or more mutations in the catalytic site are selected from E142, D219, E200, D258, E298 or E804 and mutated to alanine (A) or glutamine (Q).

In one embodiment, the one or more mutations in the loop region are selected from N160, G165, C166, V169, S201, D219, E259, Y303, H316, Y323, A141, N199, G204, C205, V208, S240, D258, E298, Y342, H355, Y362, or E804 and mutated to alanine (A) or glutamine (Q).

In one embodiment, the one or more mutations are selected from D258E, E804A, E142Q, E142A, E200A, D258A, D258Q, E200A/E298A, E200Q/E298Q, E298A, E298Q, or D258A/E298A.

In one embodiment, the one or more mutations are selected from E803A, E142Q, E142A, E298A, W298Q, or D258A/E298A.

In one embodiment, the one or more mutations have the effect of increasing the conversion rate and/or specificity of conversion from mogroside V to Siamenoside I.

In certain embodiments, the one or more mutations have the effect of increasing the conversion rate by at least about 5%, at least about 10%, at least about 15%, at least about 20% or at least about 25% or more.

In certain embodiments, the one or more mutations have the effect of increasing the specificity of conversion (Siamenoside I yield) by at least about 5%, at least about 10%, at least about 15%, at least about 20% or at least about 25% or more.

In one embodiment, the mutations shift the distribution to increased Siamenoside I production.

In certain embodiments, the distribution is shifted to increased Siamenoside I by at least about 5%, at least about 10%, at least about 15%, at least about 20% or at least about 25% or more.

In a third aspect, the method is disclosed for purifying Siamenoside I from a reaction mixture comprising:
 a) providing a mixture of low purity mogrosides;
 b) dissolving the mixture of low purity mogrosides in water or an aqueous alcohol solution to form an initial solution of mogrosides;
 c) mixing the initial solution of mogrosides with an affinity sorbent to bind mogrosides in the mixture of low purity mogrosides;
 d) washing the affinity sorbent with water to remove enzymes and impurities;
 e) eluting the affinity sorbent with a minimal volume of organic solvent to obtain a mogroside/solvent solution;
 f) distilling the mogroside/solvent solution to obtain a concentrated aqueous mogroside solution;
 g) loading the concentrated aqueous mogroside solution onto a C18 resin;
 h) eluting the C18 resin using solvent/water mixtures of increasing solvent concentration to produce one or more fractions containing Siamenoside I;
 i) distilling the one or more fractions containing Siamenoside I to obtain a concentrated aqueous Siamenoside I solution,
 j) drying the concentrated aqueous Siamenoside I solution to obtain high purity Siamenoside I, wherein the Siamenoside I is more than about 60% pure.

In one embodiment, the mogroside mixture of step a) comprises at least 85% Mogroside V.

In one embodiment, the mixture of low purity mogrosides of step a) comprises at least 90% Mogroside V.

In one embodiment, the mixture of low purity mogrosides of step a) comprises at least 95% Mogroside V.

In one embodiment, the affinity sorbent is HP20 resin.

In one embodiment, the affinity sorbent is C18 resin.

In one embodiment, the affinity sorbent/solvent mixture is pooled and solvent is removed by distillation.

In one embodiment, the affinity sorbent is added at 25× to 30× (w:w) of the mogroside content of the mixture.

In one embodiment, the organic solvent is 100% organic solvent selected from acetone, acetonitrile, ethanol, or methanol.

In one embodiment, the organic solvent is 100% methanol.

In one embodiment, the organic solvent is 100% ethanol.

In one embodiment, another cycle of steps c)-e) is performed before step f).

In another embodiment, the organic solvent is an aqueous alcoholic solution comprising water and an alcohol selected from the group consisting of methanol, ethanol, n-propanol, 2-propanol, 1-butanol, and 2-butanol.

In one embodiment, the minimal volume of organic solvent is about 2 volumes:weight resin.

In one embodiment, the distillation occurs at temperature between about 45 and about 50° C. to provide an aqueous mogroside solution.

In one embodiment, the affinity resin column is a C18 resin (Chromatorex SMB 150, 20-45 μm) column.

In one embodiment, the organic solvent comprises between about 30-40% ethanol.

In one embodiment, the organic solvent comprises between about 30-40% methanol.

In one embodiment, the organic solvent comprises between about 30-40% methanol and yields a purity of >95% Siamenoside I.

In one embodiment, the organic solvent comprises between about 50-100% methanol.

In one embodiment, the organic solvent comprises between about 50-100% methanol and yields a purity of >95% mogroside IIIE.

In another embodiment of the process, the sorbent is a macroporous polymeric adsorption resin capable of adsorbing mogrosides.

In a fourth aspect, a method is disclosed for purifying Siamenoside I from a reaction mixture comprising:
  a) providing a mixture of low purity mogrosides and reaction mixture reagents;
  b) separating the mogrosides from the reaction mixture reagents by (i) adjusting the pH of the low purity mogrosides mixture to about 10 or higher, (ii) adding alcohol to provide an alcoholic solution and (iii) filtering the alcoholic solution through a first ultrafiltration membrane to provide a first filtered solution;
  c) adjusting the pH of the first filtered solution to between about 5 and about 7 and filtering through a second ultrafiltration membrane to provide a second filtered solution;
  d) performing diafiltration on the second filtered solution to concentrate the mogrosides to provide a mogroside mixture, then mixing the mogroside mixture with water/ammonia acetate to provide a mogroside/ammonium acetate solution;
  e) contacting the mogroside/ammonia acetate solution with a fractionation column;
  f) eluting and collecting fractions containing Siamenoside I; and
  g) drying the fractions containing Siamenoside I to obtain high purity Siamenoside I with a Siamenoside I content of more than about 60% (w/w).

In one embodiment, the reaction mixture reagents are enzymes and salts.

In one embodiment the ultrafiltration membrane is a 10 kDa nominal filtration membrane. In one embodiment the ultrafiltration membrane is a 10 kDa nominal filtration membrane.

In one embodiment the fractionation column is a C18 resin column.

In one embodiment, the mogroside mixture of step a) comprises at least 85% Mogroside V.

In one embodiment, the mogroside mixture of step a) comprises at least 90% Mogroside V.

In one embodiment, the mogroside mixture of step a) comprises at least 95% Mogroside V.

In a fifth aspect, a sweetener mixture is disclosed comprising high purity Siamenoside I; wherein the high purity Siamenoside I is blended with another sweetener.

BRIEF DESCRIPTION OF DRAWINGS

FIG. 4 provides a table showing gBlock gene fragments and restriction enzyme sites for cloning to target mutations in the beta-galactosidase sequence (UniProt B7VU80).

FIG. 9A. Overall view of HPLC trace showing over 98% purity by peak area. FIG. 9B. Close up view of the minor impurities.

DETAILED DESCRIPTION OF THE INVENTION

Methods and compositions are provided to increase the yield and mogroside distribution of Siamenoside I from Mogroside V catalysis. In certain embodiments, the methods are biocatalytic methods utilizing engineered enzymes. In certain embodiments, the methods involve process controls such as temperature and pH.

Certain methods exist to catalyze conversion of mogroside V to reaction products mogroside IV, Siamenoside I, and mogroside III, but conventional processes result in low production of Siamenoside I with increased contaminating mogroside reaction products. The present methods described herein provide improvements to increase the yield of production and/or decrease in contaminating mogrosides. Purification methods provide Siamenoside I useful for applications such as sweeteners in beverage and food stuffs.

Figure 1:
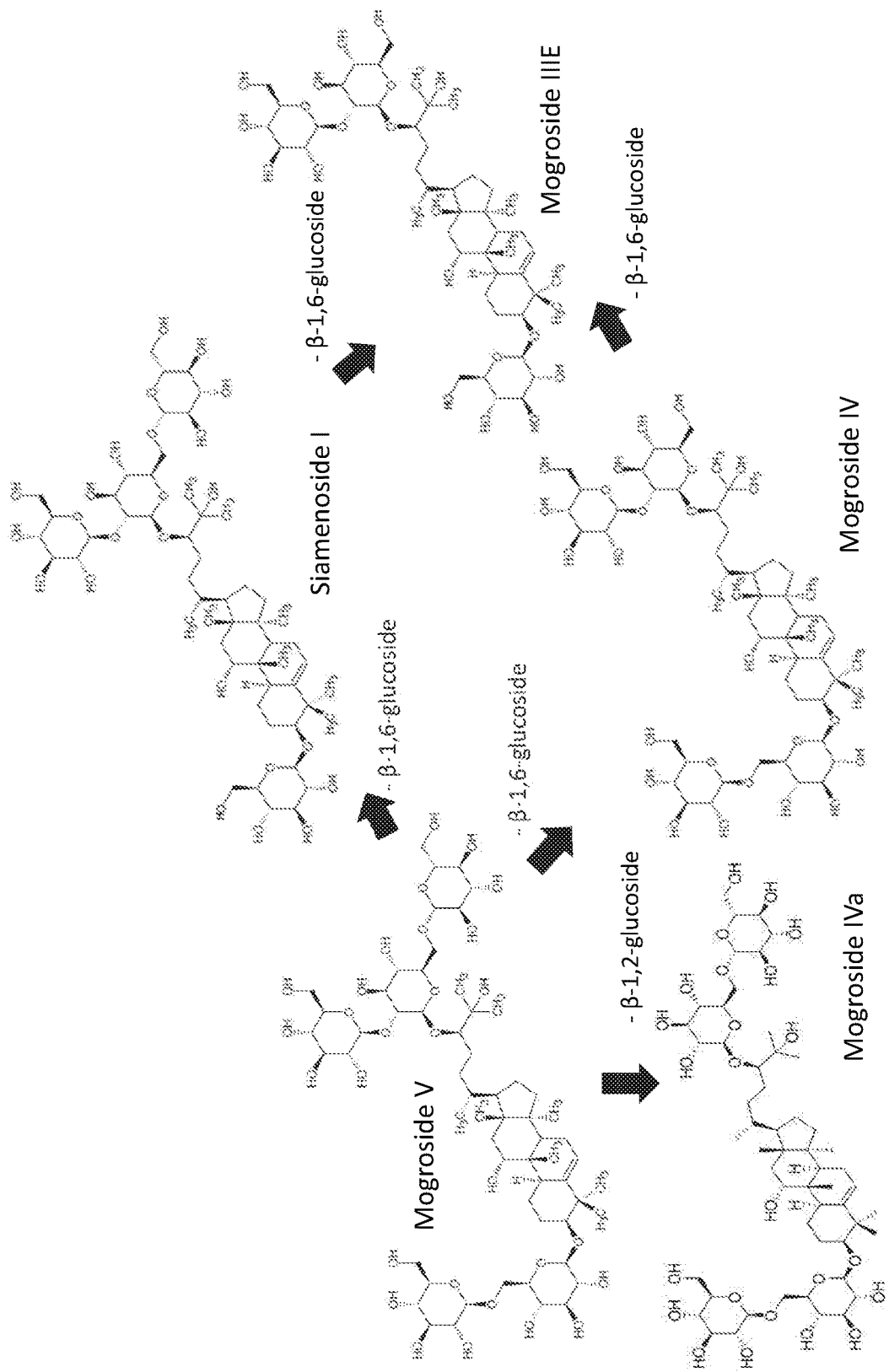
FIG. 1 provides a general schematic showing the pathways for converting Mogroside V to Mogroside IIIe via Mogroside IV or Siamenoside I.

Reaction of mogroside V to mogroside III can proceed via 2 pathway routes, each involving 2 sub-reactions in the pathway. As the chemistry/binding involved is different for each substrate or intermediate, process conditions are used to alter the rates and specificities for the enzyme to perform each of these sub-reactions. The general pathways for Mogroside III production from Mogroside V is shown in FIG. 1.

Definitions

As used herein, the term "amino acid" refers naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma.-carboxyglutamate, and O-phosphoserine.

As used herein, the term "amino acid analog" refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid.

As used herein, the term "amino acid difference" or "residue difference" refers to a difference in the amino acid residue at a position of a polypeptide sequence relative to the amino acid residue at a corresponding position in a reference sequence. The difference can be, for example, a conservative substitution, a non-conservative substitution, a deletion or an insertion.

As used herein, the term "amino acid mimetic" chemical compounds that have a structure that is different from the general chemical structure of an amino acid, but that functions in a manner similar to a naturally occurring amino acid.

As used herein, the term "β-galactosidase" or "beta-gal", refers to a glycoside hydrolase enzyme that catalyzes the hydrolysis of β-galactosides into monosaccharides through the breaking of a glycosidic bond.

As used herein, the term "β-galactosidase variant" comprises an amino acid sequence derived from the amino acid sequence of a "precursor β-galactosidase". Precursor β-galactosidases can include naturally occurring β-galactosidases and recombinant β-galactosidases. The amino acid sequence of the β-galactosidase variant can be derived from the amino acid sequence of the precursor β-galactosidase by substitution, deletion or insertion of one or more amino acids of the amino acid sequence of the precursor β-galactosidase.

As used herein, the term "biocatalysis" refers to the chemical process through which enzymes or other biological catalysts perform reactions between organic components.

As used herein, the term "biotransformation" refers to a process for the conversion of a substrate into a product within a living organism (e.g., bacteria, fungi), which includes any modifications of the chemical and/or biological nature and/or properties of the substrate occurring within the living organism and resulting in the production of the product. Single or multiple precursor molecules are provided to the living system, and after time is allowed for metabolism to occur, a product or products, consisting of a single or a small number of enzymatic modifications of the precursor molecule(s), are isolated from the medium. In alternative embodiments, biotransformation may refer to a process for the conversion of a substrate into a product by an isolated enzyme.

As used herein, the term "conservative amino acid substitution" means the substitution of an amino acid with another amino acid having a side chain with similar properties. Amino acid residues are classified into several families according to their side chains, such as basic side chains (for example, lysine, arginine, and histidine), acidic side chains (for example, aspartic acid and glutamic acid), uncharged polar side chains (for example, glycine, asparagine, glutamine, serine, threonine, tyrosine, and cysteine), nonpolar side chains (for example, alanine, valine, leucine, isoleucine, proline, phenylalanine, methionine, and tryptophan), B branched side chains (for example, threonine, valine, and isoleucin), and aromatic side chains (for example, tyrosine, phenylalanine, tryptophan, and histidine). Conservative amino acid substitution is preferably the substitution between amino acid residues in one family.

As used herein, the term "conventional methods" with respect to methods of purifying Siamenoside I include methods described in, for example, WO2014140634A1 and Chiu, Chun-Hui, et al. "Biotransformation of mogrosides from *Siraitia grosvenorii* Swingle by *Saccharomyces cerevisiae*." Journal of Agricultural and Food Chemistry 61.29 (2013): 7127-7134.

As used herein, the term "conversion" or "bioconversion" refers to enzymatic conversion (or biotransformation) of a substrate(s) to the corresponding product(s). "Percent conversion" refers to the percent of the substrate that is converted to the product within a period of time under specified conditions. Thus, the "enzymatic activity" or "activity" a given polypeptide can be expressed as "percent conversion" of the substrate to the product in a specific period of time.

As used herein, the term "engineered" with reference to the subject polypeptides/enzymes indicates that the subject has been modified from its native state. Engineered polypeptides/enzymes may differ from a native sequence by one or more amino acids and/or are fused with heterologous sequences. The term "engineered" can be used interchangeably as the term "recombinant" herein.

As used herein, the term "enzyme" refers to any substance that catalyzes or promotes one or more chemical or biochemical reactions, which usually includes enzymes totally or partially composed of a polypeptide but can include enzymes composed of a different molecule including polynucleotides.

As used herein, the term "fragment" with reference to a polypeptide refers to a shorter portion of a full-length polypeptide or protein ranging in size from two amino acid residues to the entire amino acid sequence minus one amino acid residue. In certain embodiments of the disclosure, a fragment refers to the entire amino acid sequence of a domain of a polypeptide or protein (e.g., a substrate binding domain or a catalytic domain).

As used herein, the term "fusion protein" refers to a protein created through genetic engineering from two or more proteins/peptides coding sequences joined together in a single polypeptide. Fusion proteins may include a linker (or "spacer") sequence which can promote appropriate folding and activity of each domain of the fusion protein. Fusion proteins may also include epitope tags for identification (e.g., in western blots, immunofluorescence, etc.) and/or purification. Non-limiting examples of epitope tags in current use include: HA, myc, FLAG, and 6-HIS (SEQ ID NO: 9).

As used herein, the term "identity" refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage.

As used herein, the terms "improved", "increased" or "enhanced" refer interchangeably to a detectable positive change in quantity of a parameter when compared to a standard. The parameter may vary and with reference to polypeptides includes, for example, improved production from or expression in a host cell, improved thermostability or altered temperature-dependent activity profile, improved activity or stability at a desired pH or pH range, improved substrate specificity, improved product specificity, and improved stability. The degree of improvement may vary. When expressed as a percentage, the improvement may be, for example, about 1%, about 5%, about 10%, about 15%, about 20%, about 25%, about 30%, about 40%, about 45%, about 50%, about 55%, about 60%, about 65%, about 70%, about 75%, about 80%, about 85%, about 90% or about 95% or more.

As used herein, the term "increased enzymatic activity" or "enhanced catalytic activity" refers to an improved property of the engineered enzyme disclosed herein, which can be represented by an increase in specific activity (e.g., product produced/time/weight protein) or an increase in percent conversion of the substrate to the product (e.g., percent conversion of starting amount of substrate to product in a specified time period using a specified amount of the engineered enzyme as compared to the reference enzyme).

As used herein, the term "mogroside" refers to glycosides wherein glucose is linked to the aglycone, mogrol. Mogrosides are classified into various types according to the position of linkage of glucose or the number of glucose units. Mogroside V, mogroside IV, Siamenoside I, mogroside IIIE, and 11-oxomogrosides such as, 11-oxomogroside V, 11-Siamenoside I are contained in fruits of *Siraitia grosvenorii*. Other mogrosides are also know. The novelty of the mogrosides among the cucurbitane triterpenoids are their four regio-specific oxygenations, at C3, C11, C24, and C25, forming the tetra-hydroxylated cucurbitane, mogrol.

As used herein, the term "monk fruit" or "Luo Han Guo" (luohanguo) refers to the fruit of *Siraitia grosvenori*, a member of the Curcubitaceae. The major bioactive constituents in the fruit extract are the cucurbitane-type triterpene saponins known as mogrosides. The mixed mogrosides have been estimated to be about 200-300 times as sweet as sucrose.

As used herein, the terms "mutant" or "variant" or "derivative" with respect to a protein refers to a protein with one or more residue differences in which activity is preferably increased compared to the wild type due to a mutation. Mutations include substitutions, additions, insertions, deletions, truncations, transversions and/or inversions, at one or more locations of the relative reference sequence. The sequence of the mutant protein may comprise the sequence of protein having a homology of at least 50%, 60%, 70%. 80%, 90%, 95%, 96%, 97%, 98%, or 99% to the sequence of wild-type.

The term "polypeptide", "protein" and "amino acid sequence" are used interchangeably herein and include a molecular chain of amino acids linked through peptide bonds. The terms do not refer to a specific length of the product. Thus, "peptides," "oligopeptides," and "proteins" are included within the definition of polypeptide.

As used herein, the term "profile" or "distribution" refers to the chemical composition of the reaction products produced by enzymatic hydrolysis.

As used herein, the term "purified" with reference to Siamenoside I means that the compound has been increased in purity, such that it exists in a form that is purer than it exists in its natural environment and/or in an extract. Purity is a relative term and does not necessarily mean absolute purity.

As used herein, the term "reaction conditions" refers to the environmental conditions, such as temperature, pressure, catalysts & solvent, under which a reaction progresses.

As used herein, the term "substrate" refers to a substance (e.g., a chemical compound) on which an enzyme performs its catalytic activity to generate a product.

As used herein, the term "substrate specificity" refers to the specificity that an enzyme manifests for one substrate over competing substrates. Substrate specificity can be measured as a ratio of specificity constants($k_{cat}/K_m$). Such ratios can be used to compare (i) specificities or two or more enzymes (e.g., a wild-type enzyme versus a mutant enzyme) for the same substrate or (ii) a given enzyme for two or more substrates.

The term "suitable" used herein with reference to reaction refers to those conditions under which the engineered enzyme disclosed herein is capable of converting a substrate to the desired product compound.

As used herein, the "temperature" refers to a physical quality expressing hot or cold, typically by means of a thermometer calibrated in one or more temperature scales. The most commonly used scales are the Celsius scale (formerly called centigrade) (denoted ° C.), Fahrenheit scale (denoted ° F.), and Kelvin scale (denoted K).

As used herein, the terms "wild-type" and "naturally-occurring" refer to the form found in nature. For example, a wild-type polypeptide or polynucleotide sequence is a sequence present in an organism that can be isolated from a source in nature and which has not been intentionally modified by human manipulation.

As used herein, the term "yield" refers to the amount of the final product or the desired final products obtained using the methods disclosed herein. In some embodiments, this yield is greater than that obtained using methods known in the art. In some embodiments, the term refers to the volume of the final product, and in other embodiments, the term refers to the concentration of the final product.

I. Improved Methods of Siamenoside I Production

Disclosed herein are improved methods (e.g., biocatalytic methods) for Siamenoside I production.

In certain embodiments, the disclosed methods involve modifying one or more reaction conditions over what is known in the art, including, for example, reaction temperature, reaction pH and/or reaction duration.

Siamenoside I is an intermediate in the mogroside V bioconversion pathway. The mogroside V bioconversion can occur via two pathways by this enzyme with the pathways being (Mog V to Sia I to MogIIIE) or (Mog V to Mog IVa to Mog IIIE). In certain embodiments, the methods disclosed herein change the distribution of Siamenoside I and the selectivity of the reaction to increase the yield of Siamenoside I.

Increasing Siamenoside I can be accomplished by 1) altering specificity of the enzyme to convert mogroside V to the pathway with the Siamenoside I intermediate preferentially over the pathway with the Mogroside IV intermediate and 2) by reducing the conversion rate of Siamenoside I to mogroside IIIE in the latter part of the total bioconversion pathway.

Most of the mutations identified in the G204, C205, V208 library showed less ability to convert Siamenoside I to Mogroside IIIE Conventionally, the reaction of enzyme with the fruit extract is carried out at a temperature of from about 20° C. to about 80° C., a pH from about 3 to about 10, and for a time of from about 1 hour to about 96 hours.

In one embodiment, the method of the present invention involves a bioconversion reaction comprising (i) a temperature between about 40 and 70° C. and a pH between about 6.0 and about 7.0. When the method is carried out under these reaction conditions, it shifts the conversion rate of Mogroside V to Siamenoside I to provide a Siamenoside I yield between about 50% and about 99%, thereby reducing additional contaminating mogroside products in the final reaction mixture.

As will be illustrated in more detail in the Examples, the Siamenoside I profile or distribution thereby obtained can be increased by selecting specific reaction conditions within the ranges described herein, contrary to previous teachings in the field.

In one aspect, the invention provides methods for increasing the rate of conversion and production distribution of Siamenoside I, comprising:
a) combining a solution of mogroside V with an effective amount of beta-galactosidase enzyme in a reaction mixture under suitable pH and temperature conditions to provide a beta-galactosidase/mogroside V solution,
b) incubating the beta-galactosidase/mogroside V solution for suitable time to provide a solution comprising Siamenoside I, and
c) purifying Siamenoside I from the solution comprising Siamenoside I,
wherein the Siamenoside I is greater than 90% pure.

In one embodiment, the Siamenoside I yield from step b) is greater than 60%.

In one embodiment, the Siamenoside I is greater than 95% pure.

The effective amount of the β-galactosidase enzyme may vary. Generally speaking, enzyme concentrations from about 1 to about 100 mg/mL will be suitable. In one embodiment, the enzyme concentration is from about 10 to about 90, about 20 to about 80, about 30 to about 70, about 40 to about 60, or about 50 mg/mL. In another embodiment, the enzyme concentration is about 10, about 15, about 20, about 25, about 30, about 35, about 40, about 45, about 50, about 55, about 60, about 65, about 70, about 75, about 80, about 85, about 90, about 95 or about 100 mg/mL or more.

The total concentration of solids (e.g., mogrol glycosides) in the liquid medium which is contacted with the enzyme(s) may be, for example, from about 10% by weight to about 50% by weight.

The duration of the reaction may vary. In one embodiment, the reaction runs for a duration of about 6 hr, about 12 hr, about 24 hr, about 36 hr, about 48 hr, about 60 hr, about 72 hr, about 8 4hr, about 96 hr, 12 days, 13 days, 14 days, 15 days, 20 days, 25 days, 30 days, or up to 60 days.

The suitable temperature may vary. In one embodiment, the suitable temperature is about 50° C., about 51° C., about 52° C., about 53° C., about 54° C., about 55° C., about 56° C., about 57° C., about 58° C., about 59° C., or about 60° C.

In another embodiment, the suitable temperature is between about 45° C. and about 65° C., between about 50° C. and about 60° C., between about 51° C. and about 59° C., between about 52° C. and about 58° C., between about 53° C. and about 57° C., or between about 54° C. and about 56° C.

The suitable pH may vary. In one embodiment, the suitable pH is about 6.0, about 6.1, about 6.2, about 6.3, about 6.4, about 6.5, about 6.6, about 6.7, about 6.8, about 6.9 or about 7.0 or more.

In another embodiment, the suitable pH is between about 6.0 and about 6.5, between about 6.2 and about 6.5, between about 6.3 and about 6.5, between about 6.4 and about 6.5, between about 6.5 and about 7.0, between about 6.6 and about 7.0, between about 6.7 and about 7.0, between about 6.8 and about 7.0, between about 6.8 and about 7.0, between about 6.9 and about 7.0, between about 6.2 and about 6.8, between about 6.3 and about 6.7, or between about 6.4 and about pH 6.6.

In various embodiments, the distribution of Siamenoside I in the final reaction mixture is about 40%, about 45%, about 50%, about 55%, about 60%, about 65%, about 70%, about 75%, about 80%, about 85%, about 90%, about 95%, or about 99%.

In various embodiments, the distribution of Siamenoside I in the final reaction mixture is between about 40% and about 99%, between about 45% and about 99%, between about 50% and about 99%, between about 55% and about 99%, between about 60% and about 99%, between about 65% and about 99%, between about 70% and about 99%, between about 75% and about 99%, between about 80% and about 99%, between about 85% and about 99%, between about 90% and about 99%, or between about 95% and about 99%.

In another embodiment, the distribution of Siamenoside I in the final reaction mixture is about 45%, about 50%, about 55%, about 60%, about 65%, about 70%, about 75%, about 80%, about 85%, about 90%, about 95% or about 99%.

In a further embodiment, the distribution of Siamenoside I in the final reaction mixture is between about 60% to about 90%, about 65% to about 85%, or about 70% to about 80%.

In a further embodiment, the distribution of Siamenoside I in the final reaction mixture is between about 60% and about 70%.

In a further embodiment, the distribution of Siamenoside I in the final reaction mixture is between about 40% to about 75%.

In another embodiment, the distribution of Siamenoside I in the final reaction mixture is greater than about 40%, greater than about 50%, greater than about 60%, greater than about 70%, greater than about 80% or greater than about 90%.

In one embodiment, the suitable temperature is between about 45 and about 60° C. and the suitable pH is between about 6.3 and about 7.0.

In one embodiment, the suitable temperature is between about 50 and about 60° C. and the suitable pH is between about 6.3 and about 7.0.

In one embodiment, the suitable temperature is between about 50 and about 55° C. and the suitable pH is between about 6.3 and about 7.0.

The reaction mixture may further comprise one or more additional components. In one embodiment, the reaction mixture includes glycerol. In another embodiment, the reaction mixture includes monovalent or divalent cations.

In one embodiment, when components are added to the reaction mixture, it may be in any order.

In one embodiment, the method results in a shift of Siamenoside I production reaction distribution that reduces the amount of contaminating mogroside compounds and increases purity of Siamenoside I produced.

In certain embodiment, the amount of contaminating mogroside components is reduced by an amount greater than about 5%, about 10%, about 15%, about 20%, about 25%, about 30%, about 35%, about 40%, about 45%, about 50% or more.

In certain embodiments, the purity of the Siamenoside I is increased by an amount greater than about 5%, about 10%, about 15%, about 20%, about 25%, about 30%, about 35%, about 40%, about 45%, about 50% or more.

In one embodiment, the amount of contaminating mogroside components is reduced by an amount greater than about 10% and the purity of the Siamenoside I is increased by an amount greater than about 10%.

In one embodiment, the amount of contaminating mogroside components is reduced by an amount greater than about 20% and the purity of the Siamenoside I is increased by an amount greater than about 20%.

In one embodiment, the amount of contaminating mogroside components is reduced by an amount greater than about 40% and the purity of the Siamenoside I is increased by an amount greater than about 40%.

In one embodiment, the method yields a reaction product having greater than about 60% Siamenoside I.

In one embodiment, the method yields a reaction product having between about 60 and about 99% Siamenoside I.

In one embodiment, the method yields a reaction product having between about 70 and about 95% Siamenoside I.

In one embodiment, the method yields a reaction product having between about 75 and about 90% Siamenoside I.

In another embodiment, the method yields a reaction product having about 60%, about 63%, about 65%, about 68%, about 70%, about 73%, about 75%, about 78%, about 80%, about 83%, about 85%, about 88%, about 90%, about 93%, about 95%, about 95% or about 100% Siamenoside I.

In one embodiment, the method yields a reaction product containing less than 10% mogroside IV.

In certain embodiments, the percent conversion is increased, e.g., by about 5%, about 10%, about 15%, about 20%, about 25%, about 30%, about 35%, about 40%, about 45% or about 50% or more.

In a particular embodiment, the percent conversion is between about 55 and about 99%, more particularly, about 60 to about 99%, about 65 to about 99%, about 70 to about 99%, about 75 to about 99%, about 80 to about 99%, about 85 to about 99% or about 90 to about 99%.

In another particular embodiment, the percent conversion is about 60%, about 63%, about 65%, about 68%, about 70%, about 73%, about 75%, about 78%, about 80%, about 83%, about 85%, about 88%, about 90%, about 93%, about 95%, about 95% or about 100%.

In certain embodiments, the conversion specificity is increased, e.g, by about 5%, about 10%, about 15%, about 20%, about 25%, about 30%, about 35%, about 40%, about 45% or about 50% or more.

In one embodiment of the invention, a mogroside composition is disclosed which comprises Siamenoside I and at least one mogrol glycoside selected from the group consisting of mogroside V, mogroside IV and mogroside IIIE, wherein Siamenoside I is from about 60% to about 85% by weight of the total amount of (mogroside V+mogroside IV and mogroside mogroside V is from 0 to about 40% by weight of the total amount of (mogroside V+Siamenoside I+mogroside IV and Mogroside III), mogroside IV is from 0 to about 20% by weight of the total amount of (mogroside V+Siamenoside I+mogroside IV and mogroside HIE), and mogroside IIIE is from 0 to about 40% by weight of the total amount of (mogroside V+Siamenoside I+mogroside IV and mogroside IIIE) and wherein mogroside IV, if present, is present in an amount not greater than the total amount of Siamenoside I.

The reaction may be stopped (e.g., by separating the enzyme from the fruit extract or deactivating the enzyme) when the desired mogrol glycoside profile is attained.

II. Enzyme Engineering

Siamenoside I production is catalyzed by beta-galactosidase hydrolysis of non-reducing terminal beta-D-galactose to catalyze the transition of non-reducing galactose to other compounds. Siamenoside I production can be catalyzed by beta-galactosidase hydrolysis. Beta-galactosidases are generally characterized by their ability to hydrolyze of lactose by hydrolyzing the non-reducing terminal beta-D-galactose from glucose. However, these enzymes have been shown to perform hydrolysis of other glycosidic bonds. In this case, Siamenoside I production is catalyzed by the hydrolysis of non-reducing a terminal beta-D-glucose of Mogroside V.

β-galactosidase and β-glucosidase enzymes belong to the enzyme family EC 3.2.1.21, and can be divided into several groups and classes. All the β-galactosidase/β-glucosidase enzymes reported to hydrolyze mogroside V to date belong two one of two different classes of the glycosyl hydrolase GH-A group: either Class 2 (includes β-galactosidases from *E. coli, Arthobacter* spp. and those from *Kluyveromyces* fungal species) or Class 35 (includes most other eukaryote β-galactosidases). Class 2 β-galactosidase enzymes have a tetrameric quaternary structure, whilst class 35 enzymes have a monomeric structure, but substrate range varies widely across the classes. For example, even though they all occur in Class 2, *E. coli* β-galactosidase enzymes cannot hydrolyse mogroside V, whilst those from *Kluyveromyces lactis* can do so. (Pereira-Rodríguez Á, Fernández-Leiro R, González-Siso M I, Cerdán M E, Becerra M, et al. (2012) Structural basis of specificity in tetrameric *Kluyveromyces lactis* β-galactosidase. Journal of Structural Biology 177: 392-401; Pereira-Rodríguez Á, Fernández-Leiro R, González Siso M I, Cerdán M E, Becerra M, et al. (2010) Crystallization and preliminary X-ray crystallographic analysis of β-galactosidase from *Kluyveromyces lactis*. Acta Crystallographica Section F: Structural Biology and Crystallization Communications 66: 297-300). Beta-galactosidases are widely found in mammalian organs, plant seeds, bacteria, fungi, and yeasts.

In the food industry, beta-galactosidases from yeasts such as *Kluyveromyces lactis* and *Kluyveromyces fragilis*, fungi such as *Aspergillus niger* and *Aspergillus oryzae*, and bacteria such as *Bacillus circulans*, have been used. Among them, beta-galactosidase from *Bacillus circulans* ATCC 31382 is commercially available under the trade name of Biolacta (Daiwa Kasei, U.S. Pat. No. 4,237,230 (1980)). Wild type β-galactosidase include G5160 β-galactoside from *Aspergillus oryzae* (sold by Sigma), E0025 β-glucosidase from *Clostridium thermocellum* (sold by Prozomix), E0110 β-glucosidase from Rhizoium etli (sold by Prozomix) and E0105 β-glucosidase from *Bacteroides fragilis* (sold by Prozomix).

Cloning, nucleotide sequencing, and expression of the b-galactosidase-encoding gene (lacA) from *Aspergillus oryza* has been reported. I to et al., J. Gen. Appl. Microbiol., 48, 135-142 (2002). The total sequence (5,319 bp) is available from the GenBank (Accession No. E12173). The crystal structure of β-galactoside from *Aspergillus oryzae* has been reported. Maksimainen M M et al., Int J Biol Macromol. 2013 September; 60:109-115. The genome of the wild-type *A. oryzae* has been sequenced. Genbank Accession No. AP007150 and AP007177.

Beta-galactosidase has also been characterized from *Aspergillus niger* (Kumar V, at al. (1992) Biotechnology (N Y) 10:82-85); *Aspergillus niger niger* (Hu X, et al. (2010) Appl Microbiol Biotechnol 87:1773-1782); *Aspergillus carbonarius* (O'Connell S et al. (2008) Appl Biochem Biotechnol 149:129-138); and *Aspergillus alliaceus* (Sen, S. et al. (2012) Production, purification, immobilization, and characterization of a thermostable β-galactosidase from *Aspergillus alliaceus*. Appl Biochem Biotechnol 167:1938-1953.

In certain embodiments, using certain beta-galactosidase enzymes favors the production of Siamenoside I over the production of mogroside IV (WO2014/150127) while other enzymes favor the production of mogroside IV over the production of Siamenoside I (WO2014/150127 incorporated by reference herein). Still other enzymes yield products containing approximately equal amounts of these mogrol glycosides. If a particular ratio of Siamenoside I to mogroside IV is desired in the final product, the enzyme may be selected such that it is capable of yielding the desired result. The conversion pathway of mogroside V is shown in FIG. 1. Certain narrow ranges of temperature and pH have been surprisingly found to shift the production distribution to favor Siamenoside I production.

In various embodiments, starch modifying enzymes with glycoside hydrolase activity are useful for these catalysis reactions. Such enzymes may include, but are not limited to dextranases, cellulases, glucanases, lactases, pustulanase, and many other names.

In one aspect, a method is disclosed in which monk fruit extract mogroside V is contacted with a beta-galactosidase enzyme for a time and under conditions effective to achieve the desired redistribution of Siamenoside I. That is, the reaction conditions are selected to provide the desired extent of conversion of mogroside V to Siamenoside I. Generally speaking, shorter reaction times are known to favor the production of Siamenoside I and mogroside IV over mogroside IIW (WO2014/150127 incorporated by reference herein).

In one embodiment, the beta-galactosidase is an *Aspergillus* species beta-galactosidase, for example *Aspergillus oryzae, Aspergillus niger, Aspergillus carbonarius* or *Aspergillus alliaceus*, or particular strain thereof.

In one embodiment, the beta-galactosidase is *Aspergillus oryzae* beta-galactosidase (AoBG). *Aspergillus oryzae* is generally described as a domesticated species of *Aspergillus* originating from *Aspergillus flavus*, and the two species cannot be distinguished by DNA. *Aspergillus oryzae* is known for use in enzyme production at industrial scale and as a successful expression host for production of secondary metabolites.

Representative, non-limiting wild-type *Aspergillus oryzae* strains include RIB40 (ATCC 42149).

Representative, non-limiting industrial *Aspergillus oryzae* strains include RIB128, RIB915, RIB326, BP2-1, 3.042 and A1560.

In a particular embodiment, the beta-galactosidase is a *Aspergillus oryzae* RIB strain beta-galactosidase. More than 200 RIB strains of *Aspergillus oryzae* are known. (Murakami, H. 1971. J. Gen. Appl. Microbiol. 17:281-309).

In a particular embodiment, the beta-galactosidase comprises the amino acid sequence of SEQ ID NO: 1.

In one embodiment, the beta-galactosidase is a fusion protein.

In a particular embodiment, the beta-galactosidase comprises the amino acid sequence of SEQ ID NO: 2.

Enzyme efficiency can be a limiting step in many reactions. Therefore, efforts are described to engineer improved mutant beta-galactosidase having an enhanced reaction selectivity to produce Siamenoside I from mogroside V.

Figure 14:
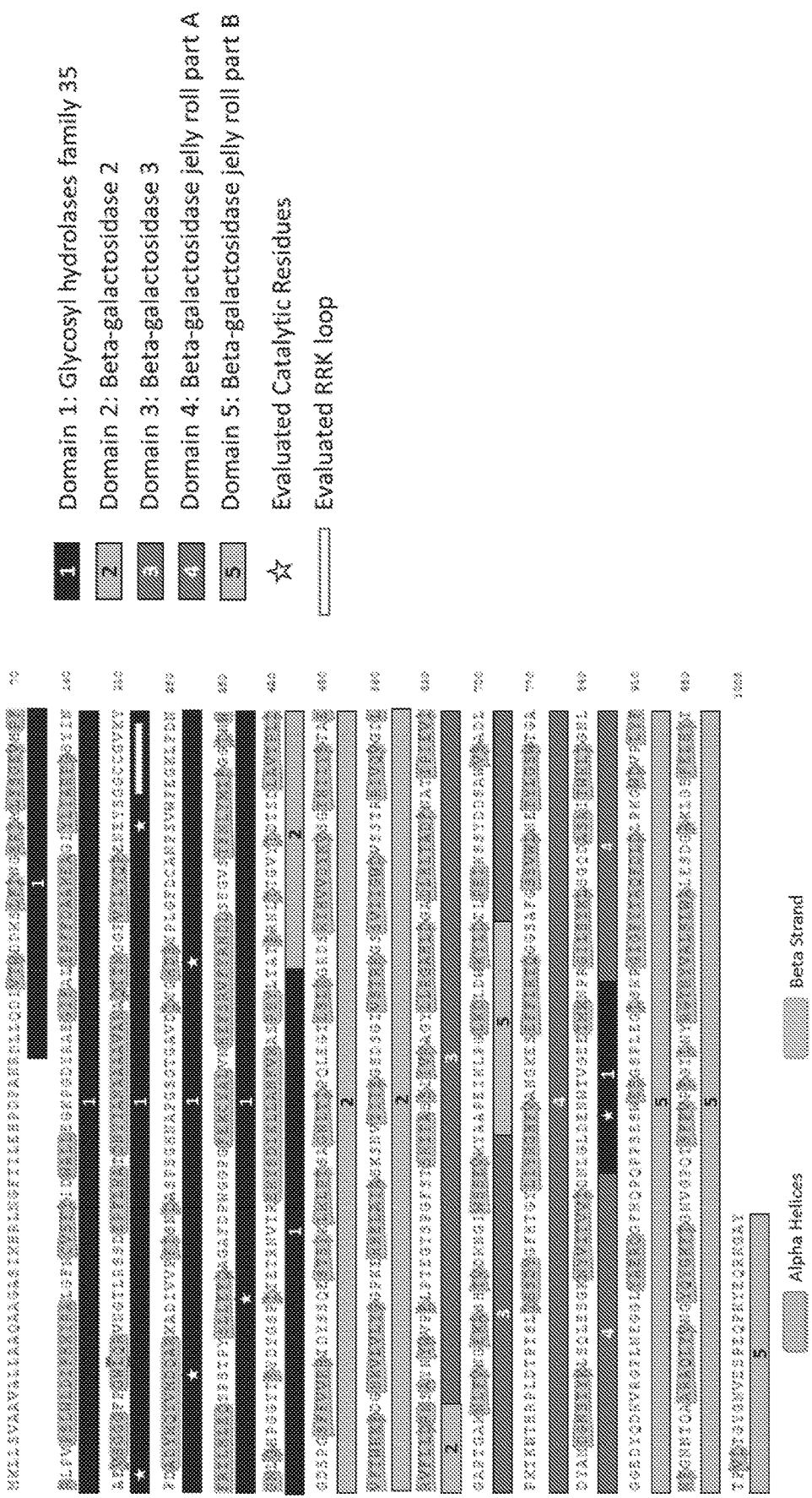
FIG. 14 shows the domains of AoBG. Figure discloses SEQ ID NO: 1.

In one embodiment, the starting (or parent) enzyme sequence to engineer improved beta-galactosidase is wild-type *Aspergillus oryzae* beta-galactosidase (AoBG). The Ao-β-gal is a large (1005 residues) multi-domain enzyme that has a catalytic (α/β)8-barrel domain. FIG. 14

In a particular embodiment, the starting enzyme comprises an amino acid sequence comprising SEQ ID NO: 1.

In one embodiment, the starting enzyme sequence is a wild-type AoBG fusion protein, and in particular, a wild-type AoBG fusion protein comprising C-terminal s-myc and hexa-His tags (SEQ ID NO: 9).

In a particular embodiment, the starting enzyme comprises an amino acid sequence comprising SEQ ID NO: 2. There are a number of enzyme engineering approaches that may be used to accomplish modification of beta-galactosidase. The modifications may be, for example, one or more amino acid differences. Those differences may be, for example, one or more substitutions, additions, insertions and deletions. The amino acid may be a naturally occurring or synthetic amino acid, as well as an amino acid analogs or amino acid mimetic that functions in a manner similar to the naturally occurring amino acids.

In one embodiment, the one or more amino acid substitutions is a conservative amino acid substitution. Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe.

In a particular embodiment, the modification comprises one or more amino acid differences in the catalytic domain or loop region. In one embodiment, the modification comprises one or more amino acid modifications in the amino acid residues 200-212 and more particularly, 200 and 2010. In a particular embodiment, the modification comprises one or more amino acid modifications in amino acid residues 204, 205 or 208. In certain embodiments, the one or more amino acid modifications are substitutions and more particularly, conservative amino acid substitutions.

In a particular embodiment, the modification comprises two or more amino acid differences in the catalytic domain or the loop region. In one embodiment, the modification comprises two or more amino acid modifications in the amino acid residues 200-212 and more particularly, 200 and 2010. In a particular embodiment, the modification comprises two or more amino acid modifications in amino acid residues 204, 205 or 208. In certain embodiments, the two or more amino acid modifications are substitutions and more particularly, conservative amino acid substitutions.

In a particular embodiment, the modification comprises three or more amino acid differences in the catalytic domain or the loop region. In one embodiment, the modification comprises three or more amino acid modifications in the amino acid residues 200-212 and more particularly, 200 and 2010. In a particular embodiment, the modification comprises three or more amino acid modifications in amino acid residues 204, 205 or 208. In certain embodiments, the three or more amino acid modifications are substitutions and more particularly, conservative amino acid substitutions.

A) Directed Approach

Using the directed approach, a Molecular Dynamics simulation was employed using the 4IUG structure of beta-galactosidase with mogroside V. Mogroside V is docked various orientations to test predicted Glu/Asp catalytic residues. The residues are modified to change to Gln/Ala in order to create potentially inactive variants. Specific libraries of relevant amino acids/targeted aa changes in the loop regions that appear to stabilize the "Siamenoside I-forming conformation." Inserts are then constructed for recombinant expression and medium throughput analysis on liquid chromatography—mass spectrometry (LCMS).

B) Semi-Rational Approaches

Using the semi-rational approach, FuncLib/other computational methods to reduce library complexity, predict optimal specificity of loop replacements. Inserts are then constructed for recombinant expression and medium throughput analysis on liquid chromatography—mass spectrometry (LCMS).

C) Random Mutagenesis

Selection Pressure:

Using the random mutagenesis approach, mogroside V is used as a sole carbon source for general rate increase. Derivatised mog V/triterpenoid is used for selective cleavage to siamenoside I (release of fluorescence/colour). A toxic or competing colour is released on further release to mogroside III.

Probing of the catalytic mechanism suggests that Siamenoside I production is attributed to a different catalytic diad than traditionally considered for this enzyme The traditional catalytic diad pair is E200, E298 while surprisingly, the inventors have found that the catalytic diad for Siamenoside I production is E200, D258. These locations are the subject for mutation to increase the activity of the enzyme for Siamenoside I production.

Variants tested have shown increases towards activity or specificity toward Siamenoside I.

In one aspect, the invention provides a modified beta-galactosidase enzyme comprising one or more mutations in the catalytic site, loop region or a combination thereof. In a particular embodiment, the modified beta-galactosidase enzyme comprises two or more mutations in the catalytic site, loop region or combinations thereof.

The mutations may be selected from substitutions, deletions, insertions or a combination thereof. A substitution means a replacement of an amino acid occupying a position with a different amino acid; a deletion means removal of an amino acid occupying a position; and an insertion means adding 1-3 amino acids adjacent to an amino acid occupying a position. Where the mutant involves more than one type of mutation, it is referred to as a combination mutant.

In a particular embodiment, the invention provides a modified beta-galactosidase enzyme comprising an amino acid sequence variant of SEQ ID. NO:1 and in particular, a variant having at least 50% identity, at least 60% identity, at least 65% identity, at least 70% identity, at least 75% identity, at least 80% identity, at least 85% identity, at least 90% or at least 95% identity to SEQ ID NO: 1. In certain embodiments, the modified beta-galactosidase enzyme may be a functional fragment thereof, i.e., retains beta-galactosidase activity.

In another particular embodiment, the invention provides a modified beta-galactosidase enzyme comprising an amino acid sequence variant of SEQ ID. NO:2 and in particular, a variant having at least 50% identity, at least 60% identity, at least 65% identity, at least 70% identity, at least 75% identity, at least 80% identity, at least 85% identity, at least 90% or at least 95% identity to SEQ ID NO: 1. In certain embodiments, the modified beta-galactosidase enzyme may be a functional fragment thereof.

In one embodiment, the mutations are selected from D258E, E804A, E142Q, E142A, E200A, D258A, D258Q, E200A/E298A, E200Q/E298Q, E298A, E298Q, or D258A/E298A of GenBank Accession No. CAW30743.1 (UniProt B7VU80).

In one embodiment, the mutation is selected from E803A, E142Q, E142A, E298A, W298Q, or D258A/E298A.

In one embodiment, the one or more mutations are within the amino acid residues 200 to 212, more particularly, 200 to 210, even more particularly, 200, 201, 202, 203, 204, 205, 206, 207, 208, 209 or 2010.

In one embodiment, the mutation is RRK67. RRK67 has mutation G204G C205R, and V208E.

In one embodiment, the mutation is E142A RRK67. The E142A RRK67 has mutations, E142A, G204G, C205R and V208E.

In one embodiment, the mutations increase the conversion rate and/or specificity of conversion. In a particular embodiment, the mutations increase the conversion rate and/or specificity of conversion by about 5%, about 10%, about 15%, about 20%, about 25%, about 30%, about 35%, about 40%, about 45%, or about 50%, In one embodiment, the mutation(s) increase the specificity constant of the mutant beta-galactosidase enzyme compared to the specificity constant of the wild-type beta galactosidase enzyme. In a particular embodiment, the substrate specificity ratio of the mutant beta-galactosidase compared to the wild-type beta galactosidase is about 1.2:1, about 1.3:1, about 1.4:1, about 1.5:1, about 1.6:1, about 1.7:1, about 1.8:1, about 1.9:1, about 2.0:1, about 2.1:1, about 2.2:1, about 2.3:1, about 2.4:1, about 2.5:1, about 2.6:1, about 2.7:1, about 2.8:1, about 2.9:1, about 3.0:1. In another embodiment, the substrate specificity ratio of the mutant beta-galactosidase compared to the wild-type beta galactosidase is about 4:1, about 4.5:1, about 5.0:1, about 5.5:1, about 6.0:1, about 6.5:1, about 7.0:1, about 7.5:1 or about 8.0:1 or more.

In one embodiment the mutations shift the distribution to increased Siamenoside I production. In a particular embodiment, the mutations shift the distribution to increased Siamenoside I by about 5%, about 10%, about 15%, about 20%, about 25%, about 30%, about 35%, about 40%, about 45%, or about 50%, The present invention also provides polynucleotides encoding the β-galactosidase variants; nucleic acid constructs, vectors, and host cells comprising the polynucleotides; and methods of using the vβ-galactosidase variants. Polynucleotides encoding the β-galactosidase variants disclosed herein can be expressed, in the form of an enzyme, using an expression vector, which typically includes regulatory sequences encoding a promoter, operator, ribosome binding site, translation initiation signal and, optionally, a repressor gene or various activator genes. Cells for use as host cells in recombinant production of the β-galactosidase variants disclosed herein can be mammal, insect, bacterial or fungal cells.

III. Improved Purification of Siamenoside I from Reaction Mixtures

The product obtained from the described enzymatic treatment (hereinafter sometimes referred to as a "modified fruit extract") may be subjected to further processing and/or purification steps, such as filtration, treatment with adsorbent, concentration and/or drying. For example, the product may be in the form of an aqueous mixture containing the desired distribution of different mogrol glycoside isomers which is concentrated by removal of water or membrane treatment to provide a more concentrated syrup useful as a sweetening agent or flavor enhancer or dried (by spray-drying, for example) to provide a solid composition (in the form of a powder, for example) which is also useful as a sweetening agent or flavor enhancer. The modified fruit extract may be combined with one or more additional sweeteners or other food ingredients (such as a bulking agent or carrier) prior to such further processing.

By using the enzymatic treatment methods described herein, Siamenoside I with a distribution shifted from naturally-occurring production may be prepared. This enzyme is more selective with more neutral reaction conditions.

In one embodiment, the enzyme is an acid-tolerant lactase, but its function at neutral pH significantly better than at acidic conditions.

The conditions under which the fruit extract starting material is contacted with enzyme may, in various embodiments of the invention, be selected to provide a modified fruit extract product wherein the siamenoside I content is increased at least two fold, at least three fold, at least five fold, at least ten fold, at least fifteen fold or at least twenty fold or more as compared to the siamenoside I content of the fruit extract starting material.

Biocatalysis reaction conditions may be selected such that the product obtained is enriched in Siamenoside I (i.e., the modified fruit extract has a mogrol glycoside content such that at least about 10%, at least about 20%, at least about 30%, at least about 40%, at least about 50%, at least about 60%, at least about 70%, at least about 80%, at least 90% or even 100% by weight of the mogrol glycoside present is Siamenoside I). The treatment methods described herein thus may be employed to obtain pure Siamenoside I.

Disclosed is a process for the bioconversion and purification of of *Siraitia grosvenori* fruit extract to give high purity Siamenoside I.

Also disclosed is a process for bioconversion and purification of high purity mixtures of mogrosides from *Siraitia grosvenori* fruit extract.

In one embodiment, a method for purifying Siamenoside I from a reaction mixture comprises:
a) providing a mixture of low purity mogrosides;
b) dissolving the mixture of low purity mogrosides in water or an aqueous alcohol solution to form an initial solution of mogrosides;
c) mixing the initial solution with an affinity sorbent to bind the mogrosides in the mixture of low purity mogrosides;
d) washing the affinity sorbent to remove enzymes and impurities with water;
e) eluting the affinity sorbent with a minimal volume of organic solvent to obtain a mogroside/solvent solution;
f) distilling the mogroside/solvent solution to obtain a concentrated aqueous mogroside solution;
g) loading the concentrated aqueous mogroside solution onto C18 resin;
h) eluting the C18 resin using solvent/water mixtures of increasing solvent concentration to produce one or more fractions containing Siamenoside I;
i) distilling the one or more fractions containing Siamenoside I to obtain a concentrated aqueous Siamenoside I solution;
f) drying the concentrated aqueous Siamenoside I solution to obtain high purity Siamenoside I having a Siamenoside I content of more than about 60% (w/w).

In one embodiment, the affinity sorbent is HP20 resin, i.e., a rigid polystyrene/divinylbenzene matrix In one embodiment, the affinity sorbent is added at 25× to 30× (w:w) of the mogroside content of the mixture.

In one embodiment, the organic solvent is selected from acetone, acetonitrile, ethanol, or methanol.

In one embodiment, the organic solvent solution is 100% methanol.

In one embodiment, the organic solvent solution is 100% ethanol.

In one embodiment, another cycle of steps c)-e) is performed before step f).

In another embodiment of the process, the solvent is an aqueous alcoholic solution comprising water and an alcohol selected from the group consisting of methanol, ethanol, n-propanol, 2-propanol, 1-butanol, and 2-butanol.

In one embodiment, the minimal volume of organic solvent is about 2 volumes:weight resin.

In one embodiment, the affinity sorbent is C18 resin, i.e., a octadecyl carbon chain (C18)-bonded silica resin.

In one embodiment, the affinity sorbent/solvent mixture is pooled and solvent is removed by distillation.

In one embodiment, the distillation occurs a temperature between about 45 and about 50° C.

In one embodiment, the affinity resin column is a C18 resin (Chromatorex SMB 150, 20-45 μm) column.

In one embodiment, Siamenoside I is purified with a solution of between about 30-40% methanol.

In one embodiment, Siamenoside I purified with a solution of between about 30-40% methanol yields a purity of >95% Siamenoside I.

In one embodiment, mogroside IIIE is purified with a solution of between about 50-100% methanol.

In one embodiment, mogroside IIIE purified with a solution of between about 30-40% methanol yields a purity of >95% mogroside IIIE.

In another embodiment of the process, the sorbent is a macroporous polymeric adsorption resin capable of adsorbing mogrosides.

In another embodiment, a method for purifying Siamenoside I from a reaction mixture comprises:
a) providing a mixture of low purity mogrosides and reaction mixture reagents;
b) separating the mogrosides from the reaction mixture reagents by (i) adjusting the pH of the mixture of a) to about 10 or higher, (ii) adding alcohol to provide an alcoholic solution and (iii) filtering the alcoholic solution through a first ultrafiltration membrane to provide a first filtered solution;
c) adjusting pH of the first filtered solution to between about 5 and about 7 and filtering through a second ultrafiltration membrane to provide a second filtered solution;
d) performing diafiltration on the second filtered solution to concentrate the mogrosides to provide a mogroside mixture, then mixing the mogroside mixture with water/ammonia acetate to provide a mogroside/ammonia acetate solution;
e) contacting the mogroside/ammonia acetate solution with a fractionation column;
f) eluting and collecting fractions containing Siamenoside I; and
g) drying the fractions containing Siamenoside I to obtain high purity Siamenoside I with a Siamenoside I content of more than about 60% (w/w).

In one embodiment, the reaction mixture reagents are enzymes and salts.

The pH to which the mixture is adjusted in b) is about 10 or higher, e.g. about 10.5 or higher, about 11 or higher, about 11.5 or higher, about 12 or higher or about 12.5 or higher. In a particular embodiment, the pH is adjusted to about 12.4. Any base can be used for the adjustment, e.g. NaOH.

The alcohol added in b) is any simple alcohol, e.g. methanol, ethanol, propanol, i-butanol or t-butanol. In a particular embodiment, the alcohol is ethanol.

The alcoholic solution in b) contains from about 5% to about 30% alcohol, e.g. from about 5% to about 25%, from about 5% to about 20%, from about 5% to about 15%, from about 5% to about 10%, from about 10% to about 30%, from about 10% to about 25%, from about 10% to about 20%, from about 10% to about 15%, from about 15% to about 30%, from about 15% to about 25%, from about 15% to about 20%, from about 20% to about 30%, from about 20% to about 25% and from about 25% to about 30%. In a particular embodiment, the alcoholic solution contains about 20% alcohol. In a more particular embodiment, the alcoholic solution contains about 20% ethanol.

In one embodiment the first and/or second ultrafiltration membrane is a 10 kDa nominal filtration membrane. In one embodiment the first and/or second ultrafiltration membrane is a 10 kDa nominal filtration membrane.

The pH to which the filtered solution is adjusted in c) is from about 5 to about 7, e.g. from about 5 to about 6.5, from about 5 to about 6, from about 5 to about 5.5, from about 5.5 to about 7, from about 5.5 to about 6.5, from about 5.5 to about 6, from about 6 to about 7, from about 6 to about 6.5 and from about 6.5 to about 7.

In one embodiment the fractionation column is a C18 resin column.

In one embodiment, the mixture of low purity mogrosides in step a) comprises at least 90% Mogroside V.

In one embodiment, the mixture of low purity mogrosides in step a) comprises at least 95% Mogroside V.

The present invention further provides a sweetener mixture comprising the high purity Siamenoside I; wherein the high purity Siamenoside I is blended with another high intensity sweetener.

In one embodiment of the sweetener mixture, the another high intensity sweetener is selected from the group consisting of steviol glycosides including a purified sweet steviol glycoside mixture, stevioside, rebaudioside A, rebaudioside B, rebaudioside C, rebaudioside D, rebaudioside E, rebaudioside F, rebaudioside I, rebaudioside J, rebaudioside M, rebaudioside N, rebaudioside O, dulcoside A, dulcoside B, rubusoside, and stevia; mogroside IV,; mogroside V; isomogroside V, mogroside IIIE, Luo Han Guo sweetener; monatin and its salts (monatin SS, RR, RS, SR); glycyrrhizic acid and its salts; curculin; thaumatin; monellin; mabinlin; brazzein; hernandulcin; phyllodulcin; glycyphyllin; phloridzin; trilobatin; baiyunoside; osladin; polypodoside A; pterocaryoside A; pterocaryoside B; mukurozioside; phlomisoside I; periandrin I; abrusoside A; cyclocarioside I; and combinations thereof.

The present invention also provides a product comprising the high purity mogrosides. In one embodiment, the product is selected from the group consisting of food, beverage, pharmaceutical composition, tobacco, nutraceutical, oral hygienic composition, or cosmetic.

The term "mogrosides" refers to mogrol, dihydroxymogrol and oxo-mogrol glycosides, including mogroside IIE, mogroside IIB, mogroside III, mogroside IV, mogroside V, 11-oxo-mogroside V, mogroside VI, Siamenoside I, and grosmomoside I.

The term "TM content" means the Total Mogrosides content, and it is calculated as the sum of 4 mogrosides including Mogroside V, Mogroside IV, Siamenoside I, and Mogroside IIIe.

The term "highly purified" or "high purity" means the Siamenoside I content of at least 90% (w/w) on dry basis.

The term "impurity" means any compounds other than Siamenoside I which are present in the mixture at more than 0.0001% (w/w) on dry basis. Non-limiting examples of impurities include other mogrosides besides Siamenoside I, proteins, pigments, polysaccharides, aldehydes, unsaturated aldehydes, methyl ketones, butyl crotonate, phenolic compounds as well as other non-mogroside compounds.

The process of purification of Siamenoside I of the present invention is applicable for any mixture of low purity mogrosides with the Siamenoside I content of less than 60% w/w on dry basis.

In one embodiment, the purification process of the present invention further comprises filtering with the usage of ultrafiltration and/or nanofiltration membranes. Membranes with molecular weight cut-off (MWCO) size of 1000, 1500 and 2000 are used. The resulted solution is consecutively passed through ultrafiltration and/or nanofiltration membranes with MWCO 1000, 1500, 2000 and 2500. A stirred cell membrane system from Sterlitech Corp. (USA) is used for this purpose. Anyway any suitable filtration system known to art may be used for this purpose. Non-limiting examples of membrane manufacturers are Koch Membrane Systems Inc. (USA), GE-Osmonics (USA), Alfa Laval (Sweden). Flat sheet, hollow fiber, spiral and other membranes may be used. Diafiltration is used to increase membrane filtration process efficiency. Depending on membrane size the retentate or permeate contained the main amount of mogrosides. After each membrane treatment the mogroside containing fraction (retentate or permeate) is concentrated or diluted again till total solids content 0.1-50% (wt/vol) preferably 0.5-10% and passed through the next membrane. The solution is passed through increasing membrane sizes (from MWCO 1000 to 2500).

IV. Utility as a Sweetener in Food and Beverage Manufacture

The Siamenoside I thereby obtained may be used as a high intensity sweetener, alone or in combination with one or more other high intensity sweeteners or conventional sweeteners such as sucrose. Siamenoside I may also be utilized as a flavor enhancer at sub-sweetening concentrations in food and beverage products and the like.

The modified fruit extracts and Siamenoside I obtained in accordance with the present invention may be incorporated into any type of food or beverage composition as sweeteners or flavor enhancers. Non-limiting examples of such food and beverage compositions include baked goods, soups, sauces, processed meats, canned fruits, canned vegetables, dairy products, frozen confections, carbonated soft drinks, sports drinks, ready to drink teas, dairy drinks, alcoholic beverages, energy drinks, flavored waters, vitamin drinks, fruit drinks, fruit juices, powdered soft drinks, candy, confections, chewing gum, nutraceutical products and the like. The modified fruit extracts and Siamenoside I may also be used in products such as medicines, pharmaceutical products and tobacco products. The modified fruit extract and/or Siamenoside I is included in an amount effective to impart the desired amount of sweetness to the sweetened product. The product may contain one or more additional sweeteners, e.g., a caloric sweetener such as sugar or another high intensity sweetener (either natural or synthetic) or may be free of any sweetening component other than the modified fruit extract or Siamenoside I of the present invention. The modified fruit extracts and Siamenoside I described herein may also find utility as taste enhancers, wherein they are included in a food or beverage at a concentration below the threshold where they impart a sweet taste to the product but in sufficient amount that they improve, modify or enhance the taste of the product.

The high purity mogrosides can be used either alone or in combination with other high intensity sweeteners in food, beverage, pharmaceutical composition, tobacco, nutraceutical, oral hygienic composition, or cosmetic. The other high intensity sweeteners include steviol glycosides including a purified sweet steviol glycoside mixture, stevioside, rebaudioside A, rebaudioside B, rebaudioside C, rebaudioside D, rebaudioside E, rebaudioside F, rebaudioside I, rebaudioside J, rebaudioside N, rebaudioside O, rebaudioside M, dulcoside A, dulcoside B, rubusoside, and stevia; mogroside IV; mogroside V; Luo Han Guo sweetener; monatin and its salts (monatin SS, RR, RS, SR); glycyrrhizic acid and its salts; curculin; thaumatin; monellin; mabinlin; brazzein; hernandulcin; phyllodulcin; glycyphyllin; phloridzin; trilobatin; baiyunoside; osladin; polypodoside A; pterocaryoside A; pterocaryoside B; mukurozioside; phlomisoside I; periandrin I; abrusoside A; cyclocarioside I; and combinations thereof.

In some embodiments, the Siamenoside I obtained in accordance with the invention is present in the foodstuff or beverage at a concentration of at least 25, at least 50, at least 100, at least 200, at least 500, at least 1000, at least 1500 or at least 2000 ppm (based on weight, as calculated on a dry solids basis). At such concentrations, the Siamenoside I tends to function as a sweetener, i.e., it imparts a sweet taste to the foodstuff or beverage or increases the perceived sweetness of a foodstuff or beverage that already has (prior to the incorporation of the Siamenoside I) some degree of sweetness. In other embodiments, the Siamenoside I is present in a foodstuff or beverage at a lower concentration, e.g., below the concentration at which the Siamenoside I imparts any perceived sweetness. The maximum sub-sweetening concentration (sometimes referred to as the "sweetness detection threshold") will vary somewhat depending upon the mogrol glycoside content of the modified fruit extract or the purity of the Siamenoside I, but typically sub-sweetening concentrations of the Siamenoside I will be more than about 1 ppm but less than about 60 ppm.

Concentrations of from about 10 to about 50 ppm, for example, may be effective to improve the taste or flavor of a foodstuff or beverage without increasing the perceived sweetness of such foodstuff or beverage.

Advantages of the present invention will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

EXAMPLES

Example 1: Modifying Mogroside Conversion Distribution for Selective Increase in Siamenoside I Production Reaction conditions were scanned for conditions that improved distributions of Siamenoside I production.

Reaction of mogroside V to mogroside III can proceed via 2 pathway routes, each involving 2 sub-reactions in the pathway. As the chemistry/binding involved is different for each substrate or intermediate, process conditions are used to alter the rates and specificities for the enzyme to perform each of these sub-reactions. (FIG. 1)

Methods:
Enzyme Concentration and Preparation

Ultrafiltration was used to prepare a 4X concentrated enzyme solution of Maxilact A4. MAXILACT®(GODO-YNL2 β-galactosidases (EC 3.2.1.23)). As produced, Maxilact A4 contains≥50% (w/w) glycerol and 60-120 g/L sodium chloride. Microfiltration (MF) (0.2 μm), and/or ultrafiltration (UF, 5 kDa, 400 cm2 membrane) was used to produce ~150 mL of each target enzyme concentration (the enzyme was microfiltered prior to UF operations). The flux rate for UF was a relatively slow ~1.5 mL/min. The Maxilact A4 batch used for this work was DSM Batch No. 417 792 301.

Evaluation of pH vs. Temp vs. Time

Reactions were designed to improve desirable distribution by controlling pH, temperature, and time of reactions. Reactions were performed in 50 mL conical tubes with a total reaction volume of 28.8 mL containing 8 mL of the 4× enzyme concentration in as-received enzyme media, with a final reaction mixture containing 3 mM magnesium chloride, and 0.1 M sodium acetate. Initial pH conditions were titrated to 5.8, 6.0, 6.3, 6.6, and 7.0. Reactions were microfiltered (0.2 μM) for sanitization. Reactions were not agitated after initial mixing and the pH was determined to ±0.1 pH units using a micro pH meter. Samples of the reactions were removed on days 1, 4, 7, and 11, and then analyzed by the HPLC method.

HPLC Analysis

Samples were analyzed on a Phenomenex Synergi-Hydro RP, 250 mm×4.6 mm, 4 μm (part #00G-4375-E0) ran at 55° C. at a flow rate of 0.5 mL. min using a gradient of two solvents. Solvent A was composed of 0.569 g of ammonium acetate and 0.231 g of acetic acid in 2 L of 18 MΩ·cm Water. Solvent B was composed of acetonitrile. Elution of compounds was monitored by a UV dectector set to 215 nm, 4 nm bandwidth, reference at 265 nm with 100 nm bandwidth. The gradient profile was 25% solvent B at 0 minutes, 58% solvent B at 25 minutes, 90% solvent B at 35 minutes, 90% solvent B at 38 minutes, 25% solvent B at 38.1 minutes, and 25% solvent B at 43 minutes. With this gradient, all major peaks were well resolved and compared to mogroside standards ran with this method. 11-oxomogroside V eluted at about 8.6 minutes, mogroside V eluted at about 9.4 minutes, 11-oxosiamenoside I eluted at about 10.1 minutes, siamenoside I eluted at about 10.6 minutes, mogroside IV eluted at about 11.3 minutes, and mogroside IIIE eluted at about 12.7 min.

Samples were ultrafiltered with a 10 kDa spin filter and 5× dilution in 20% acetonitrile in water before injection. The injection volume was 50 microliters.

Additive Experiments at Alternate pH

Reactions were set-up in order to evaluate the potential to improve desirable distributions by addition of various supplements. Reactions were performed in 50 mL conical tubes with a total reaction volume of 28.8 mL containing 8 mL of the 4× enzyme concentration in as-received enzyme media, with a final reaction mixture containing 3 mM magnesium chloride, 0.1 M sodium acetate with various supplements. Glycerol was supplemented to 25% or 50% of total reaction volume in various reactions. Sodium chloride was supplemented to a final concertation 33 g/L. Calcium chloride was supplemented to a concentration of 0.1/L. Potassium chloride was supplemented to 0.5% (w/v). Initial pH conditions were titrated to 6.0 and 6.6. Reactions were micro-filtered (0.2 μM) for sanitization. Reactions were not agitated after initial mixing and the pH was determined to ±0.1 pH units using a micro pH meter. Samples of the reactions were removed on days 1, 4, 7, and 11, and then analyzed by the HPLC method.

Results:

These methods show that temperatures above 50° C. and higher pHs give better distributions to Siamenoside I production.

Lower temperature and pH increase the ratio of mogroside IIIE faster and with less contaminants.

Higher pH and Temperature Significantly Improve Yield to Siamenoside I.

At or around pH 6.6 and higher than 50° C. gave greater than 50% conversion of mogroside V.

At or around pH 6.3 or higher than 55° C. gave greater than 50% conversion of mogroside V.

Low pH and Temperature Significantly Improve Yield to Mogroside IIIE:

At or around pH 5.8 and lower than 50° C. gave greater than 60% conversion of mogroside V.

At or around pH 5.8 or lower than 55° C. gave greater than 60% conversion of mogroside V.

A key feature of this bioconversion is that it reduces Mogroside V levels and keeps Mogroside IV levels under 10%, which aids in purification.

Figure 3A:
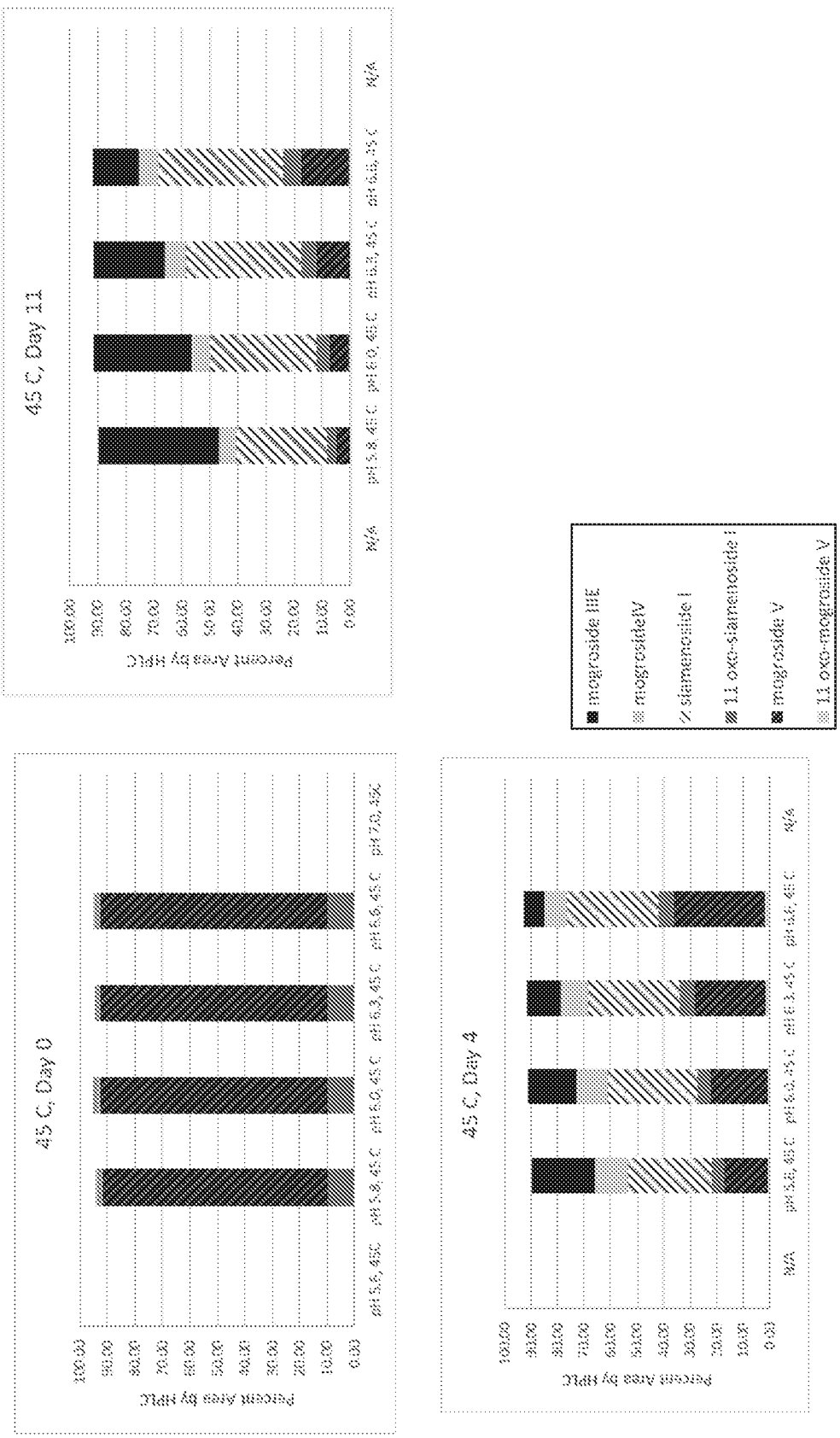
FIGS. 3A-3B and 3C provide a series of graphs showing mogroside production at varying temperature and pH.
Figure 3B:
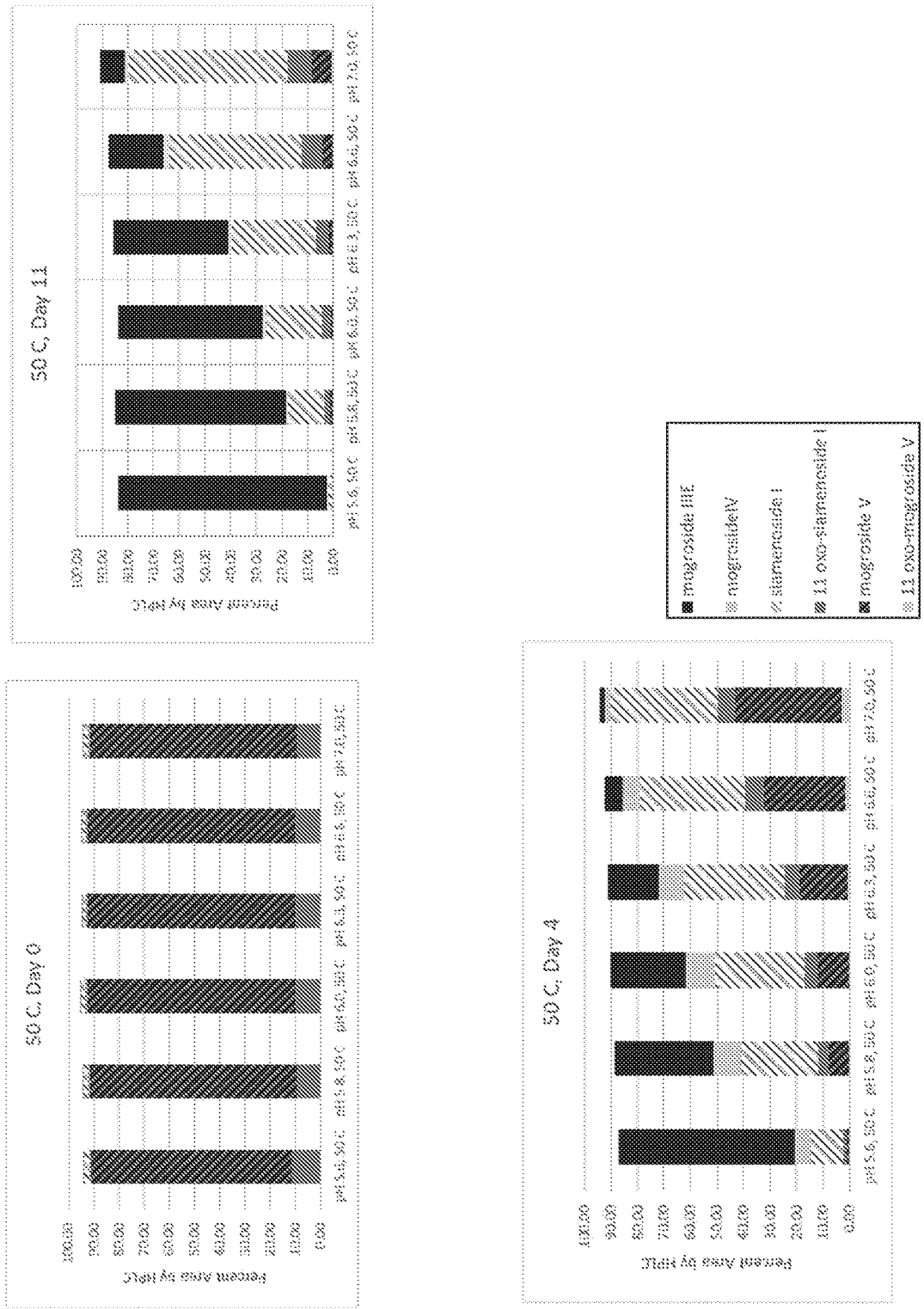
Figure 3C:
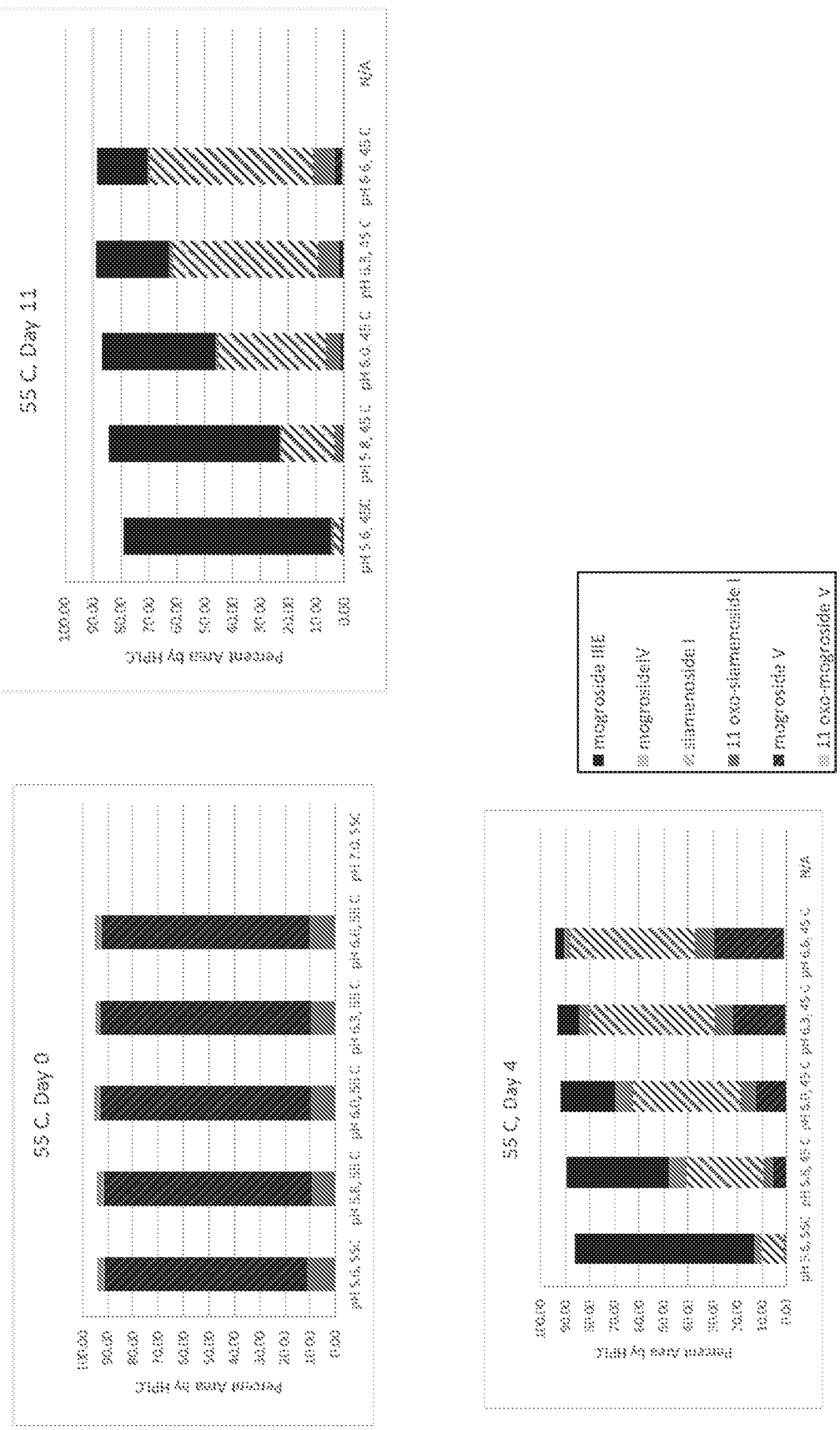

These results are summarized graphically in FIG. 3.

TABLE 1 pH variation at 45° C.

| | day 11 N/A | pH 5.8, 45° C. | pH 6.0, 45° C. | pH 6.3, 45° C. | pH 6.6, 45° C. | N/A |
|---|---|---|---|---|---|---|
| 11 oxo-mogroside V | | 0.06 | 0.64 | 0.34 | 0.51 | |
| mogroside V | | 4.65 | 6.82 | 11.64 | 16.95 | |
| 11 oxo-siamenoside I | | 3.66 | 4.55 | 5.46 | 6.50 | |
| Siamenoside I | | 32.12 | 37.74 | 41.18 | 44.48 | |
| mogrosideIV | | 6.25 | 6.89 | 7.71 | 7.01 | |
| mogroside IIIE | | 42.74 | 34.74 | 25.24 | 16.18 | |

TABLE 2 pH variation at 50° C.

| | day 11 pH 5.6, 50° C. | pH 5.8, 50° C. | pH 6.0, 50° C. | pH 6.3, 50° C. | pH 6.6, 50° C. | pH 7.0, 50° C. |
|---|---|---|---|---|---|---|
| 11 oxo-mogroside V | 0.00 | 0.60 | 0.07 | 0.23 | 0.53 | 0.84 |
| mogroside V | 0.11 | 0.73 | 1.07 | 1.72 | 3.73 | 7.66 |
| 11 oxo-siamenoside I | 0.29 | 2.34 | 3.44 | 4.82 | 7.94 | 9.34 |
| siamenoside I | 1.73 | 14.19 | 21.91 | 32.99 | 51.77 | 61.97 |
| mogrosideIV | 0.41 | 0.69 | 1.22 | 1.28 | 2.14 | 1.71 |
| mogroside IIIE | 81.44 | 66.45 | 56.15 | 44.65 | 21.50 | 9.63 |

TABLE 3 pH variation at 55° C.

| | day 11 pH 5.6, 55° C. | pH 5.8, 55° C. | pH 6.0, 55° C. | pH 6.3, 55° C. | pH 6.6, 55° C. | N/A |
|---|---|---|---|---|---|---|
| 11 oxo-mogroside V | 0.44 | 0.14 | 0.25 | 0.38 | 0.61 | |
| mogroside V | 0.37 | 0.45 | 0.91 | 1.58 | 2.74 | |
| 11 oxo-siamenoside I | 0.46 | 2.86 | 5.42 | 7.28 | 7.94 | |
| siamenoside I | 2.39 | 18.97 | 38.56 | 52.31 | 58.17 | |
| mogrosideIV | 0.89 | 0.84 | 0.95 | 1.07 | 0.96 | |
| mogroside IIIE | 74.50 | 60.99 | 40.46 | 26.09 | 18.10 | |

Additives:

In addition to varying the temperature at pH of the reaction mixture, it was determined which additives increase the distribution of Siamenoside I production. The addition of glycerol and monovalent and divalent cations changed the distribution of Siamenoside I production. Glycerol concentration had only a minor effect on the reaction and observed distribution. However, additions of monovalent and divalent ions appear to improve the distribution towards Siamenoside I formation. The addition of NaCl, CaCl, and KCl improve the Siamenoside I by 5-10%. NaCl appears to slow the reaction slightly, but also reduces the amount Mogroside IIE formed in these reactions.

TABLE 4

Additive impact on reaction at 50° C. and pH 6.0

| | 50% more Glycerol (25% of total reaction volume) | 100% more Glycerol (50% of total reaction volume) | +NaCl, 33 g/L | +CaCl2, 0.1 g/L | +KCl (0.5%) |
|---|---|---|---|---|---|
| Temperature | 50° C. | 50° C. | 50° C. | 50° C. | 50° C. |
| pH (Ambient) | | | | | |
| 11 days | 6.0 | 6.0 | 6.0 | 6.0 | 6.0 |
| 11 oxo-mogroside V | 0.05 | 0.42 | 0.46 | 0.27 | 0.25 |
| mogroside V | 2.73 | 5.04 | 6.98 | 1.67 | 2.04 |
| 11 oxo-siamenoside I | 6.9 | 6.74 | 8.39 | 7.56 | 7.75 |
| Siamenoside I | 49.55 | 49.39 | 59.42 | 56.65 | 58.05 |
| mogrosideIV | 1.84 | 2.15 | 1.50 | 1.33 | 0.77 |
| mogroside IIIE | 29.60 | 28.17 | 14.89 | 25.43 | 24.46 |

TABLE 5

Additive impact on reaction at 50° C. and pH 6.6

| | 50% more Glycerol (25% of total reaction volume) | 100% more Glycerol (50% of total reaction volume) | +NaCl, 33 g/L | +CaCl2, 0.1 g/L | +KCl (0.5%) |
|---|---|---|---|---|---|
| Temperature | 50° C. | 50° C. | 50° C. | 50° C. | 50° C. |
| pH (Ambient) | | | | | |
| 11 days | 6.6 | 6.6 | 6.6 | 6.6 | 6.6 |
| 11 oxo-mogroside V | 0.7 | 0.58 | 0.48 | 0.43 | 0.42 |

TABLE 5-continued

Additive impact on reaction at 50° C. and pH 6.6

| | 50% more Glycerol (25% of total reaction volume) | 100% more Glycerol (50% of total reaction volume) | +NaCl, 33 g/L | +CaCl2, 0.1 g/L | +KCl (0.5%) |
|---|---|---|---|---|---|
| | | | Temperature | | |
| | 50° C. | 50° C. | 50° C. | 50° C. | 50° C. |
| | | | pH (Ambient) | | |
| 11 days | 6.6 | 6.6 | 6.6 | 6.6 | 6.6 |
| mogroside V | 8.32 | 12.08 | 9.87 | 4.47 | 5.73 |
| 11 oxo-siamenoside I | 7.59 | 8.6 | 8.88 | 9 | 9.1 |
| Siamenoside I | 58.69 | 62.89 | 63.89 | 66.05 | 66.81 |
| mogroside IV | 1.80 | 1.51 | 1.82 | 0.67 | 1.21 |
| mogroside IIIE | 9.79 | 9.40 | 8.37 | 14.00 | 11.34 |

Example 2: Over-Expressing Wild Type *Aspergillus oryzae* Beta-Galactosidase in Yeast Method:
Wild-Type Expression Vector Creation The full length wildtype coding sequence for a β-glucosidase enzyme from *Aspergillus oryzae* (PDB accession number 4IUG_A) was synthesized as gBlocks Gene Fragments (Integrated DNA Technologies, IDT, USA) in two parts, codon-optimized for expression in *Pichia pastoris* yeast cells (Geneart, Invitrogen, Germany) and designed for cloning into the pPICZα A vector from the EasySelect™ *Pichia* Transformation System (Invitrogen, Thermofisher, USA) via a three way ligation using compatible restriction enzyme sites Eco R1, Kpn 1 and Sac II (NEB, USA).

Variant Construction (Dyad Evaluation)

For evaluating the catalytic residues potentially responsible for hydrolysis of glucose units from the mogroside substrates undergoing digestion, variants enzyme sequences of the β-glucosidase enzyme from *Aspergillus oryzae* were created. Multiple amino acid variant enzymes are described in Table 1. In order to replace the coding regions of the previously constructed vector carrying the wild type enzyme sequence, new vectors were constructed as follows: gBlocks including complimentary coding sequences between the restriction enzymes listed in Tables 1 but with the corresponding variant point mutations introduced were constructed. These gBlocks and the vector backbones were then digested with these restriction enzymes under the conditions provide by the restriction enzyme manufactures. The isolated, restricted DNA fragments were then ligated, transformed, and sequenced to verify proper construction as is standard in the art. (FIG. 4)

Codon-optimized for expression in *S. cerevisiae* or *P. pastoris* and designed for fusion with the a-mating factor (N-terminus) and the s-myc and 6*His tags (SEQ ID NO: 9) (C-terminus) encoded by pPICZaA vector, and with relevant restriction enzyme sites included. No STOP codon was included to allow fusion with the vector derived C-terminal s-myc and 6*His tags (SEQ ID NO: 9).

Transformation of *Pichia pastoris* Cells

Transformation-ready DNA was prepared by linearizing the required pPICZαA expression construct plasmid DNA using Sac I. EasyComp™ transformation was then performed according to manufacturer's instructions (Invitrogen, Thermofisher, USA). Briefly, between 0.5-1 µg of linearized DNA was added to 100-200 µL competent cells, mixed with 1 mL solution II and incubated with shaking at 30° C. for 1 hour before heat-shock at 42° C. for 10 minutes. Cells were then mixed with YPD and outgrown for 1 hour at 30° C. with no shaking. Transformed cells were then harvested (3000 g, 5 minutes) and washed in 500 µL, Solution III before resuspension in 2004, Solution III, and plating on YPD plates containing 100 µg per mL Zeocin™ (Invitrogen, Thermofisher, USA). Transformants were selected after growth for 48-72 hours at 30° C. and patched onto YPD plates containing 100 µg per mL Zeocin™ for subsequent analysis.

Expression of *Aspergillus oryzae* β-Glucosidase Enzyme Using *Pichia pastoris* Cells A single colony was inoculated into 10 mL of buffered minimal glycerol yeast (BMGY) medium in a 50 mL tube and cultured at 30° C. overnight with shaking (250 rpm) until culture reached an OD600 nm 2-6. Cells were then harvested (3000 g, 5 minutes) and resuspended in buffered minimal methanol medium (BMM) containing 1% methanol at ~OD600 nm 1.0, and grown for 72 hours at 30° C. with shaking (250 rpm), and with the addition of methanol to 1% volume each day to maintain induction of the AOX promotor. Cells were harvested (8000 g, 10 minutes) and the supernatant concentrated using an Amicon to yield active partially purified enzyme. The presence of active AoBG enzyme was confirmed by identification using ONPG and mogV enzymatic assays, SDS-PAGE separation and visualization with Bulldog Protein Dye, as well as proteomics analysis of the supernatant and pellet fractions from *Pichia* cells, comparing negative vector-containing strains with those expressing AoBG.

β-galactosidase ONPG Activity Assays

Standard β-galactosidase assays were performed at room temperature using o-nitrophenyl-β-D-galactopyranoside (ONPG, Sigma) as a substrate in 2004, volume with detection of o-nitrophenol release at 420 nm (UV-Spectra Max Spectrophotometer, Molecular Devices, USA). A typical reaction contained 50 mM sodium citrate buffer pH 5.6, 10 mM magnesium chloride and 100 mM potassium chloride with 2 mM ONPG and the desired amount of enzyme (usually 104, conc. supernatant). Partially purified AoBG (Sigma G5160, USA) was used as a positive control at a final concentration of 1 U mL−1. Vmax was calculated using the SpectraMax Plus software (Molecular Devices, USA) and when required kinetics were determined by varying the concentration of substrate and kinetic determinants calculated using Hyper™ (J. S. Easterby, Liverpool University).

Mogroside Biocatalytic Assays

Standard mogroside biocatalytic assays were performed at 37° C. in 500 µL, volume 50 mM sodium citrate buffer pH 5.6, 10 mM magnesium chloride, 10 mM substrate (typically mogroside V) and 50 µg mL−1 enzyme, and incubated for 24-96 hours. Mogroside glucosidation activity was detected by direct HPLC detection and quantification of mogroside V substrate and mogroside products from filtered reaction supernatant, and quantified by comparison with standard curves based on peak.

Analytical Methods

Mogroside compounds HPLC separation and quantification was conducted using a Synergi Hydro-RP column (250 mm×4.6 mm or 150 mm×4.6 mm) with an initial flow rate of 1 mL min−1 and a water: acetonitrile gradient as per below, similar to that described by Zhou et al. (WO 2014/150127). Compounds were detected at 210 nm using diode array detector (Agilent Technologies, USA), and calibration curves established using standard curves from 0.1 to 10 mM.
Results:

Reaction distributions were evaluated for G5160 beta-galactosidase (Sigma), Maxilact A4 beta-galactosidase (DSM) and Pp-*Aspergillus oryzae* beta-galactosidase. The product ratios for recombinant expression as shown in Table 6.

TABLE 6

|        | G5160 | ML   | PpAoBG |
|--------|-------|------|--------|
| Mog V  | 19%   | 22%  | 24%    |
| Siam I | 41%   | 49%  | 43%    |
| Mog IV | 11%   | 12%  | 21%    |
| Mog III| 11%   | 17%  | 12%    |
| Mog II | 14%   |      |        |
| Mog I  | 4%    |      |        |

Using 12.8 g/L MG-V (10 mM) at pH 6.0, 50° C. for 96 hrs reaction time

G5160 is β-Galactosidase active mixture from isolated from cultured *Aspergillus oryzae*.

Maxilact® (ML) A4 is an acid lactase/β-Galactosidase enzyme preparation from *Aspergillus oryzae* expressed in *Aspergillus niger* as described in GRAS notice 00510 (FDA, https://www.fda.gov/default.htm). It recombinantly expressed in *Aspergillus niger* by a plasmid carrying the *Aspergillus oryzae* TOL gene.

Pp-*Aspergillus oryzae* β-Galactosidase (PpAoBG) is the same acid lactase/β-Galactosidase enzyme as the Maxilact® A4. Instead of using an *Aspergillus niger* expression system, a *Pichia pistoris* system is used. *Pichia pistoris* does not have a background β-Galactosidase. Using this system provides a cleaner system for the various evaluations. In addition, the TOL gen//β-Galactosidase enzyme was expressed in the *Pichia pistoris* system recombinantly using a protein export system. The produced peptide will be identical to the one in the Maxilact® A4 is an acid lactase/β-Galactosidase enzyme preparation from *Aspergillus oryzae* expressed in *Aspergillus niger* as described in GRAS notice 00510.

Active enzyme expression is achieved when single colonies are inoculated into 5 ml wells of 96 well growth blocks, grown to OD 3.0, then pelleted, resuspended in induction medium and induced/grown for 72-96 hrs.

Figure 2A:
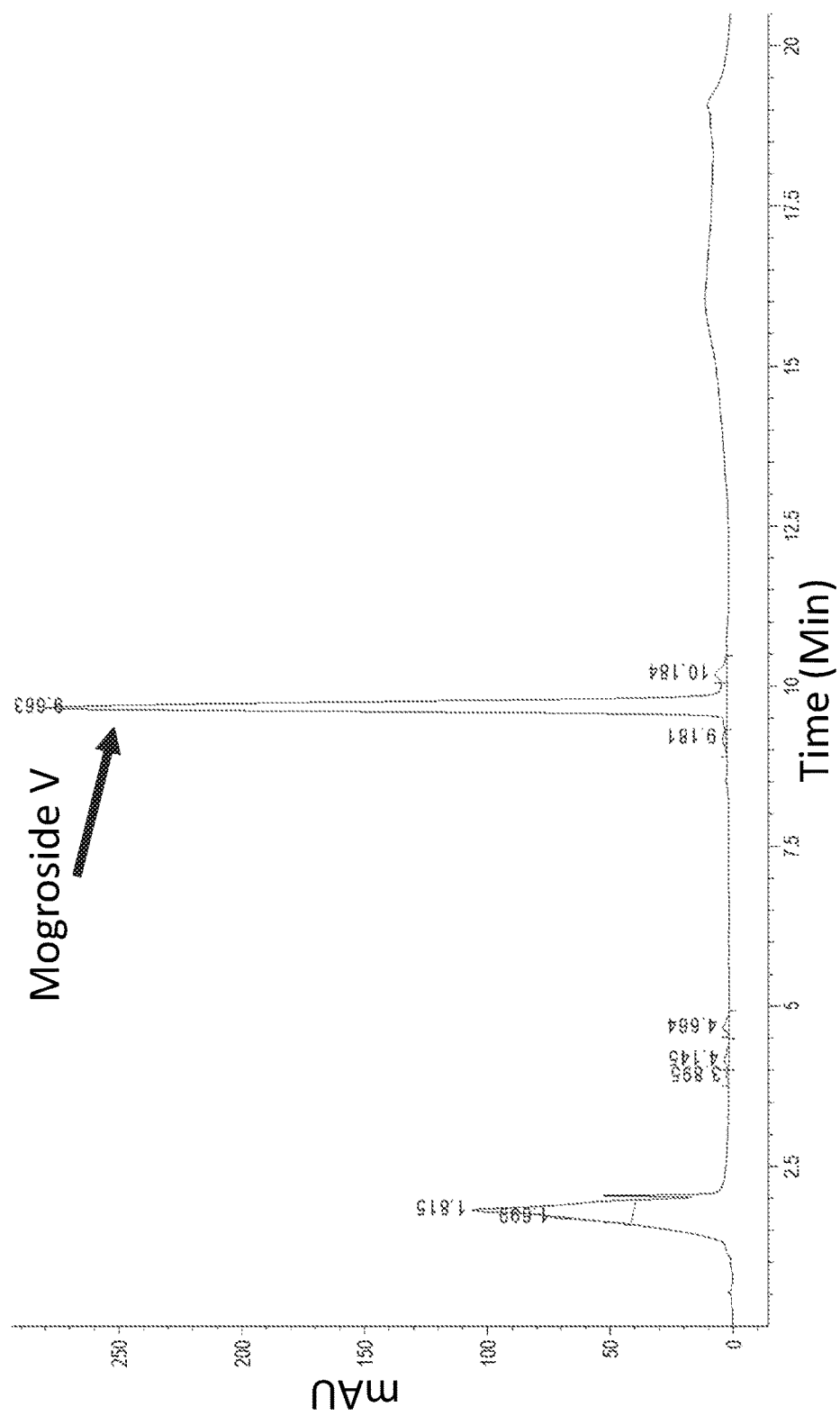
FIGS. 2A and 2B provides HPLC graphs showing mogroside concentrations in a negative control (FIG. 2A) sample and a sample in which *P pastoris* expresses AoBG reaction (96 hr induction) 48 hrs reaction (FIG. 2B).
Figure 2B:
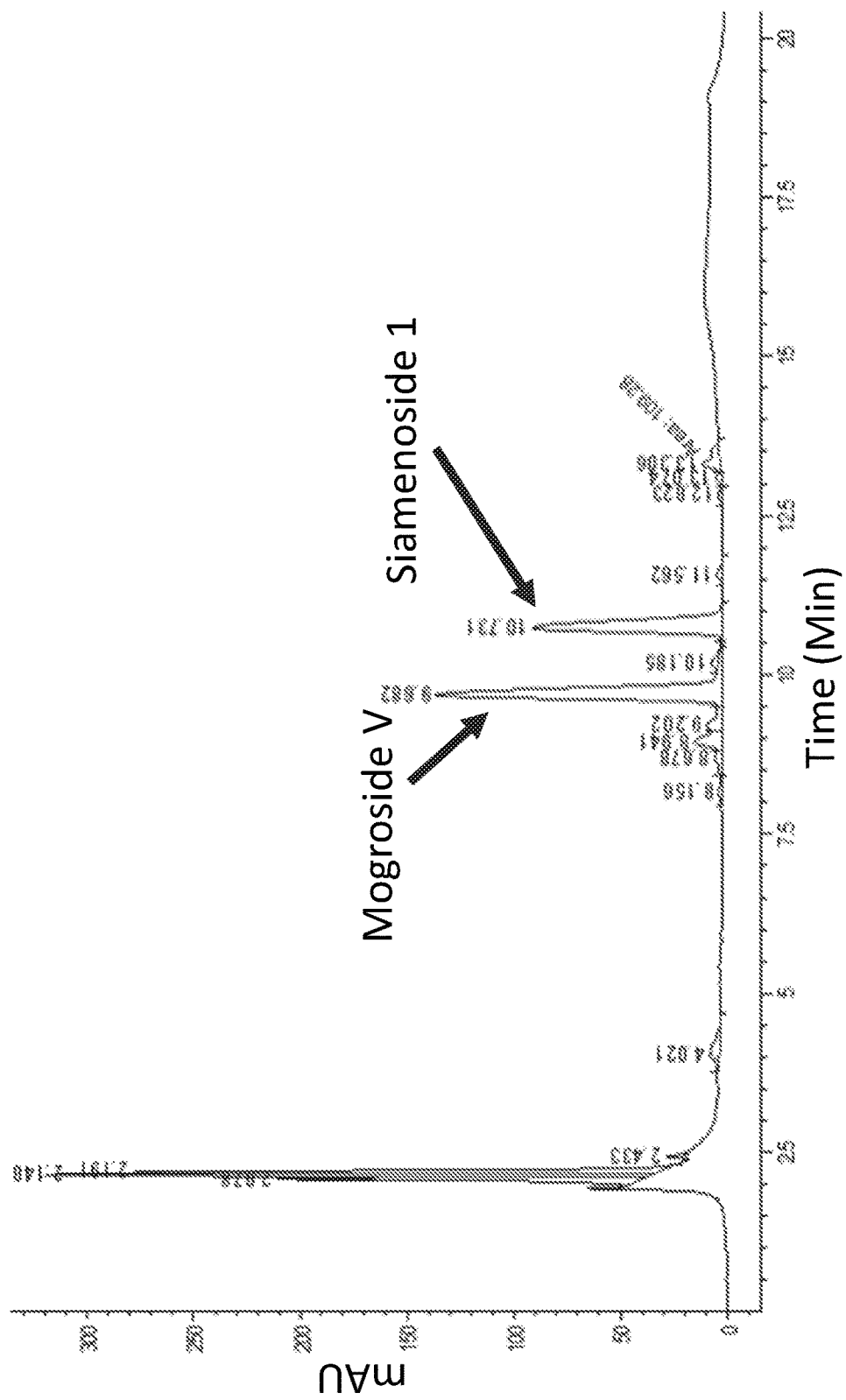

Activity has been confirmed by ONPG, DNS and mogV assay HPLC analysis after 40 hrs assay at 37° C. thus far. Principally Siamenoside I produced ~32% after 48 hrs. (FIG. 2)

Figure 5:
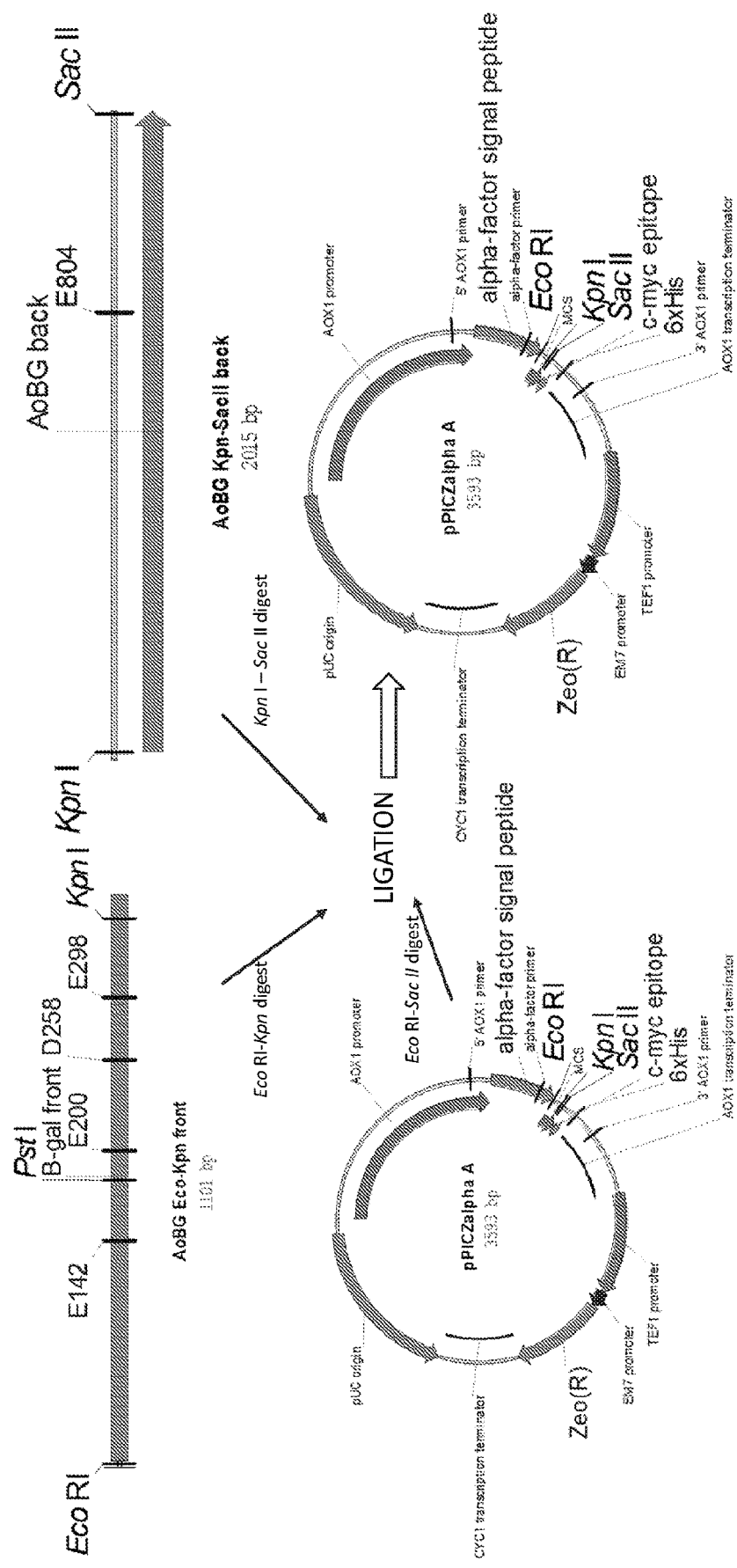
FIG. 5 provides a diagram showing vector maps of plasmids for transforming target cells and expressing mutant enzymes. Figure discloses "6xHis" as SEQ ID NO: 9.

Example 3: Structure-Based Analysis to Engineer *Aspergillus oryzae* Beta-Galactosidase Enzyme to Yield Improved Product Profiles The purpose of this work was to engineer improved beta-galactosidase enzymes to selectively shift the distribution of Siamenoside I production during mogroside V conversion. (FIG. 5)
Library Generation A custom degenerate library was synthesised comprising an Eco RI-Kpn I DNA fragment to replace the Eco RI-Kpn I region between bp 1209 and 2207 in pPICZαA-AoBG master plasmid (FIG. 5). The fragment was synthesised with degenerate RRK codons in place of the codons for amino acids G165, C166 and V169, and amplified to yield a library with (Geneart, GmBH, Thermofisher). All other codons were as per DNA sequence 1.

250 ng of library DNA was digested with Pst 1 and Kpn I, cleaned and concentrated (DNA Clean & Concentrator, Macherey-Nagel) and ligated with 30 ng of gel-purified pPICZαA-AoBG master plasmid digested with Pst 1 and Kpn I, using T4 DNA ligase (NEB). The efficiency of the library was tested by transforming 4 uL into TOPP 10 chemically competent cells (Invitrogen), and then the remainder was transformed into DH5α CloneCatcher cells, and the outgrowth used to inoculate 100 mL Luria broth containing Zeocin (100 µg mL−1) for growth at 37° C. overnight and large-scale plasmid preparation (Plasmid DNA Midiprep, Qiagen).

Generate and Screen *Aspergillus oryzae* β-Glucosidase Libraries for Active Site Amino Acid Residue Functional Analysis Enzyme variants with alanine (A) and glutamine (Q) replacements were made for each of the of the five charged residues identified in Stage 1 as being likely candidates for glycoside hydrolysis of mogroside V (E142, E200, D258, E298, E804), and expressed in *Pichia pastoris*.
Methods:
Library Generation A custom degenerate library was synthesized comprising an Eco RI-Kpn I DNA fragment to replace the Eco RI-Kpn I region between bp 1209 and 2207 in pPICZαA-AoBG master plasmid (FIG. 5). The fragment was synthesized with degenerate RRK codons in place of the codons for amino acids G165, C166 and V169 and amplified to yield a library with (Geneart, GmBH, Thermofisher). All other codons were as per DNA sequence 1.

250 ng of library DNA was digested with Pst 1 and Kpn I, cleaned and concentrated (DNA Clean & Concentrator, Macherey-Nagel) and ligated with 30ng of gel-purified pPICZαA-AoBG master plasmid digested with Pst 1 and Kpn I, using T4 DNA ligase (NEB). The efficiency of the library was tested by transforming 4uL into TOPP 10 chemically competent cells (Invitrogen), and then the remainder was transformed into DH5a CloneCatcher cells, and the outgrowth used to inoculate 100 mL Luria broth containing Zeocin (100 µg mL−1) for growth at 37° C. overnight and large-scale plasmid preparation (Plasmid DNA Midiprep, Qiagen).

Molecular dynamics was employed to perform computational simulations to better understand binding of various mogroside to the pre-determined molecular structure of Beta-galactosidase (Uniprot: B7VU80; GenBank CAW30743.1) Beta-galactosidase enzyme from *Aspergillus oryzae*. These simulations allowed for structural changes in the both the mogroside and protein active site structures in order to determine which parts of the active site most likely directing the observed activity and preference for conversion to Siamenoside I. The protein structure used in this simulations is reported as 4IUG in the Protein Database (PDB). In different simulations, either mogroside V, Mogroside IV, or Siamenoside I was docked roughly into the proposed active site of the enzyme. In addition, different starting orientations of these mogroside molecules were also evaluated. The simulation suggested that several residues contributed to binding of mogrosides V and discrimination or occlusion of Siamenoside I from the active site. A key finding was that a specific loop region in the enzyme peptide sequence (between amino acid 202 and 209 (B7VU80 sequence) corresponding to 163 to 170 (4IUG sequence)) was likely responsible for the differences in activity. Notably the molecular dynamic simulation suggested that stabilizing this loop region may promote siamenoside I formation. A directed mutations and screen scheme was developed to create a library of enzyme variants to evaluate.

Positions (G204, C205, V208) were mutated at each spot in combination via an RRK degenerate codon library scheme. An RRK library is one in which any nucleotide—A, or G—may be present in the first two positions of a targeted codon (R), and only G or T may be present in the third position (K). The library will allow each of the 3 wildtype amino acid positions to be mutated to R,N,D,E,G,K, or S. The total library has 343 possible combinations.

Once the library was cloned and evaluated for completeness, the variant library was expressed in a *Pichia* expression system. This system allows individual enzyme variants to be culture, expressed, and exported into the culture media without contaminating beta-galactosidase activity. In doing so, individual enzyme variants are expressed in a well plate format, processed to collect and normalize solutions of relatively pure enzyme concentrations. The resultant normalized enzyme solutions were used to perform evaluations via a medium throughput LC-MS method. Those variant enzymes that showed improved function over wildtype enzyme for Siamenoside I yield were sequences to determine the specific mutation responsible for the improvement.

Transformation into *Pichia*

The resultant plasmid DNA was linearized by digestion with Sac I and transformed into chemically competent *Pichia pastoris* cells, in aliquots with 1 μg linearized DNA per 200 μL cells (*15) as described in Section 1. Positive transformants were selected on 150 mm YPD agar plates containing Zeocin (100 μg mL−1). Positive transformants were confirmed by isolation of genomic DNA and amplification of a 3 kb PCR product encoding the inserted AoBG gene using primers AoBG-F-Eco (SEQ ID NO: 4) and AoBG-R (SEQ ID NO: 5). PCR products were sequenced (Macrogen, S. Korea) to confirm the substitutions at RRK positions using primers AoBG-inner-F (SEQ ID NO: 6) and AoBG-Kpn-R (SEQ ID NO: 7).

DNA sequence 2: Eco-Kpn RRK Loop Library DNA (Geneart custom degenerate library synthesis 18ABRBLC, Geneart, GmBH):

Eco R1 and Kpn 1 cloning sites are underlined. The RRK degenerate codons are highlighted with bold text. Degeneracy: R-A or G; K-G or T.

(SEQ ID NO: 8)

Gtgctcgaattcatgaagttgttgtctgttgctgccgttgctttgttggc tgctcaagctgctggtgcttctatcaaacatagattgaacggtttcacca tcttggaacatccagatccagctaaaagagatttgttgcaagatatcgtt acctgggatgacaagtccttgtttattaacggtgaaaggatcatgttgtt ctccggtgaagttcatccttttagattgccagttccatctttgtggttgg acattttccacaaaattagagccttgggtttcaactgcgtttccttttac attgattgggccttgttggaaggtaaaccaggtgattatagagccgaagg tatttttgctttggaaccatttttcgatgctgctaaagaagctggtatct acttgattgctagaccaggttcttacattaacgctgaagtttctggtggt ggttttccaggttggttgcaaagagttaacggtactttgagatcttccga tgaaccattatgaaggctaccgataattacattgctaatgctgctgctgc agttgctaaagctcaaattactaatggtggtccagtcatcttgtaccaac cagaaaatgaatactctggtrrkrrktgtggtrrkaagtatccagatgct -continued gattacatgcaatacgttatggatcaagctagaaaggccgatatcgttgt tccattcatttctaatgatgcctctccatctggtcataatgctccaggtt ctggtactggtgctgttgatatctatggtcatgattatacccattgggtt tcgattgtgctaatccatctgtttggccagaaggtaaattgccagataat ttcagaaccttgcacttggaacaatctccatctactccatactcgttgtt ggaatttcaagctggtgcatttgatccatggggtggtcctggttttgaaa aatgttatgccttggtcaaccacgagttctctagagtttttacagaaac gacttgtccttcggtgtttctactttcaacttgtacatgactttcggtgg taccaattggggtaatttgggtcatccaggtggttacacatcttatgat Expression and Screening of Library Variants Single transformant colonies from 3.2.2 were inoculated into 2mL BMGY in 48 well-growth blocks and grown overnight at 30° C., 1000 rpm in a benchtop incubator before dilution of cell culture from each well into 2 mL BMM medium an equivalent well in a fresh growth block, to an OD600 nm of 1.0, and growing the induction growth blocks at 30° C., 1000 rpm in a benchtop incubator for 72 hours. The cells were then harvested (5000 g, 10 minutes) and the supernatant from each well concentrated using a 30 kDa cut-off Amicon Ultra 0.5 mL concentrator column (10 000 g, 5 minutes). Enzymatic assays were setup in fresh growth blocks to a total volume of 500 μL, comprising with 50 mM sodium citrate buffer pH 5.6, 10 mM magnesium chloride, 10 mM mogroside V and 50 μL concentrated supernatant (~35 μg mL−1 protein). Assays were incubated without shaking at 37° C. for 72 hours. 190 μL of reaction was combined with 10 μL 10 mM internal standard (N-Boc-) and 5 μL analyzed by HPLC.

Analytical Methods

Mogroside compounds HPLC separation and quantification was conducted using a Synergi Hydro-RP column (250 mm×4.6 mm or 150 mm×4.6 mm) with an initial flow rate of 1 mL min−1 and a water: acetonitrile gradient as per below, similar to that described by Zhou et al. (WO 2014/150127). Compounds were detected at 210 nm using diode array detector (Agilent Technologies, USA), and calibration curves established using standard curves from 0.1 to 10 mM. 150 mm column retention times in minutes: mog V 9.5, sia 1 10.6, mog IVa 10.5, mog IV 11.3, mog III 12.6, mogl I 13.2. 250 mm column retention times: mog V 12.3, sia 1 13.2, mog IVa 13.5, mog IV 14.1, mog III 15.3, mog II 16.2.

Results:

Cells expressing enzyme variants grown in buffered minimal medium were induced for 72 hr with 1% methanol (refreshed every 24 hr), the culture supernatant harvested and assayed for standard ONPG activity over 30 minutes and mogroside V activity at pH 5.6, 37° C. for 72 hrs. The resultant activity data (Table 2) identified E200 and D258 as the likely catalytic pair for acid/base and nucleophilic attack of mogroside V by the *A. oryzae* β-glucosidase enzyme. Somewhat surprisingly, alanine replacement of E298, one of the canonical residues involved in galactose catalysis by β-glucosidase enzymes [1,2], did not result in loss of mogroside V activity, although it did result in decreased activity with o-nitrophenyl-β-galactoside (oNPG) as a substrate.

One enzyme variant, D258E (putative replacement of a catalytic aspartate with glutamate residue), resulted in an increased initial rate of mogroside hydrolysis, but without a significant increase in the ratio of Siamenoside I (siaI) production or siaI:mogIII product ratio. This is consistent with molecular dynamics data which suggests that this replacement extends the active site residue closer to the site of catalysis on the mogrosideV substrate molecule.

Generate and screen *Aspergillus oryzae* β-glucosidase libraries for active site amino acid residue functional analysis Two enzyme variants (E142A and E804A) resulted in an increased ratio of Siamenoside I production from mogroside V. There are two likely explanations for this:
1) Expansion of/or increased flexibility within the mogroside V "binding pocket" creates reduced likelihood of Siamenoside I binding in a catalytic conformation and progressing to smaller mogrosides.
2) Removal of the functionality of an amino acid residue involved in a separate opportunistic catalytic site for Siamenoside I glycoside hydrolysis by the enzyme i.e. it is possible that different residues act as the catalytic dyad under different circumstances or with different size substrates.

Chromatography analysis shows comparison to P5160 beta-galactosidase from Sigma Chemical. This enzyme was previously reported to have much better activity toward Siamenoside I production however it is shown in the present experiments to produce Mogroside IVa which is contrary to previous reports in WO2014/150127.

A comparison of wildtype and variant enzyme activity with mogroside V, Siamenoside I and an equimolar mixture of both illustrated that the variants E142A and E804A act by reducing the effectiveness of Siamenoside I as a substrate in the presence of mogroside V, resulting in an accumulation of Siamenoside I and a decrease in the production of mog IV and mog III.

TABLE 7

β-galactosidase and mogroside V hydrolyzing activity of *A. oryzae* β-glucosidase enzyme (UniProtKB: B7VU80) variants

| Variant (in GenBank: CAW30743.1) | oNPG (mAu/min/mg) | Mogroside Hydrolysis (72 h, 37 C., pH 5.6) | | | | |
|---|---|---|---|---|---|---|
| | | Initial Rate (μmol/min/mg) | Reaction Progress (%) | Sia 1 (%) | Sia: MogIV | Sia: MogIII |
| wildtype | 33.1 ± 1.5 | 1.74 | 85 | 44 | 2.0 | 3.9 |
| D258E | 41.4 ± 0.9 | 2.70 | 99 | 55 | 2.1 | 2.8 |
| E804A | 34.7 ± 0.4 | 3.06 | 78 | 62 | 3.3 | 18.6 |
| E142Q | 34.6 ± 0.5 | 2.05 | 88 | 43 | 2.2 | 3.8 |
| E142A | 33.6 ± 0.4 | 2.16 | 89 | 73 | 13 | 16.2 |
| E200A | INACTIVE | | | | | |
| D258A | INACTIVE | | | | | |
| D258Q | INACTIVE | | | | | |
| E200A; E298A | INACTIVE | | | | | |
| E200Q; E298Q | INACTIVE | | | | | |
| E298A | 6.3 ± 0.1 | 2.08 | 85 | 52 | 2.1 | 3.5 |
| E298Q | 5.2 ± 0.1 | 1.82 | 89 | 48 | 2.2 | 3.7 |
| D258A, E298A | INACTIVE | | | | | |

TABLE 8

Comparison of mogroside V and Siamenoside I hydrolyzing activity of *A. oryzae* β-glucosidase enzyme variants: molar percentage of substrates and products. Reactions were conducted at pH 5.6, 37° C. for the time indicated in parentheses for each column.

| Compound | Mog V Substrate (10 mM) (24 h) | | Sial Substrate (10 mM) (24 h) | | Equimolar MogV: Sial Substrate (5 mM each) (48 h) | |
|---|---|---|---|---|---|---|
| | wildtype | E142A | wildtype | E142A | wildtype | E142A |
| mog V | 75 | 67 | | | 27 | 10 |
| sia I | 22 | 32 | 66 | 84 | 45 | 82 |
| mog IV | 1 | | | | 4 | 0.2 |
| mog III | 2 | 1 | 15 | 12 | 9 | 3 |
| mog II | | | 15 | 3 | | 0.1 |

Abbreviations:
mogV - mogroside V,
sai I - Siamenoside I,
mog IV - mogroside IV,
mog III - mogroside III,
mog II - mogroside II.

Conclusion for the Catalytic Dyad Variants:

A targeted analysis of potential active site amino acid residues involved in mogroside V hydrolysis by *Aspergillus oryzae* β-glucosidase revealed some surprising insights, identifying E200 and D258 as the likely catalytic pair for acid/base and nucleophilic attack of mogroside V and highlighting several variants with an increased Siamenoside I yield from mogroside V glucosidation (E142A, E804A) and/or an increased rate of mogroside V hydrolysis (D258E).

Loop replacement libraries were designed using molecular dynamics simulations to enhance the binding of the "three sugar" component of mogroside V to loop region 202-212 of the enzyme to enhance formation of the desired product (Siamenoside I), and reduce the rate of further hydrolysis to the undesirable mogroside I, II and III compounds. Altering the side-chains of amino acid residues G204, C205, V208 to 7 different amino acid residue variants in a combinatorial manner, replacing with charged residues promotes binding of sugar sidechains (e.g. Asn, Ser, Lys, Arg, Gly, Glu, Asp [to stabilize loop])

Library size 73 (643) variants to be screened and assessed using the Pichia expression system.

Selection of Library Variants with Increased Yield of Siamenoside I

A total of 660 gene-enzyme variants transformed into Pichia pastoris were expressed and screened for improved Siamenoside I production form mogroside V. Wildtype enzyme showed Siamenoside I yields of about 66% under the assay conditions. Therefore, variants showing improved function were chosen if they surpassed a yield value >70% by peak area during this first pass evolution.

48 variants were selected based on Siamenoside I yields of >70% by peak area for a second pass evaluation. The cell lines were regrown and assayed with both mogroside V and Siamenoside I as substrates, independently. PCR amplicons from the inserted AoBG gene within genomic DNA of the selected strains were sequenced to identify the responsible RRK substitutions, and a pattern of particularly higher yields of Siamenoside I was found to general correlate with a motif of Glu/Asn in position 204, and Arg or Glu in position (208 UniProtKB: B7VU80/GenBank: CAW30743.1 numbering).

Additional evidence suggesting the screen was providing candidates with improved function, a set of randomly picked colonies was also evaluates by the secondary pass evaluation. Interestingly, all variants with Gly Gly Gly substitutions showed a decreased yield of siamenoside I from mog V compared to wildtype AoBG enzyme activity

TABLE 9

Identified candidates with improved function

| Variant | Amino Acid Substitutions | Siamenoside I Substrate Evaluation Reaction Progress | Siamenoside I Substrate Evaluation % Peak Area Siamenoside I | Siamenoside I Substrate Evaluation % Peak Area Siamenoside I Left After 72 hr |
|---|---|---|---|---|
| wildtype | GCV | 85 | 66 | 25 |
| S1 RRK 3 | NKR/NNR | 85 | 76 | 25 |
| S1 RRK 7 | EER | 84 | 77 | 78 |
| S1 RRK 11 | GRE | 88 | 83 | 80 |
| S1 RRK 13 | ESG | 89 | 77 | 80 |
| S1 RRK 14 | NNE | 75 | 74 | 84 |
| S2 RRK 1 | ENS | 87 | 68 | 81 |
| S2 RRK 2 | GDG | 87 | 76 | 78 |
| S2 RRK 4 | GGG | 86 | 58 | 74 |
| S2 RRK 6 | GEG | 89 | 73 | 70 |
| S2 RRK 8 | ENG | 93 | 75 | 70 |
| S2 RRK 9 | GGG | 86 | 64 | 66 |
| S2 RRK 10 | KNS | 88 | 70 | 72 |
| S2 RRK 11 | GNG | 89 | 71 | 72 |
| S2 RRK 12 | GCV (wildtype) | 89 | 66 | 35 |
| S2 RRK 13 | EES | 88 | 72 | 73 |
| S2 RRK 14 | DSE | 88 | 74 | 73 |
| S2 RRK 15 | RRG | 92 | 64 | 62 |
| S2 RRK 16 | NGR | 87 | 72 | 72 |

TABLE 9-continued

Identified candidates with improved function

| Variant | Amino Acid Substitutions | Siamenoside I Substrate Evaluation Reaction Progress | Siamenoside I Substrate Evaluation % Peak Area Siamenoside I | Siamenoside I Substrate Evaluation % Peak Area Siamenoside I Left After 72 hr |
|---|---|---|---|---|
| S3 RRK 1 | RKN | 86 | 70 | 68 |
| S3 RRK 2 | GGS/GGN | 87 | 70 | 68 |
| S3 RRK 3 | RRD | 86 | 72 | 74 |
| S3 RRK 4 | GSD | 84 | 73 | 76 |
| S3 RRK 5 | ESG | 87 | 73 | 69 |
| S3 RRK 6 | RNK | 71 | 64 | 84 |
| S3 RRK 7 | DSE | 85 | 72 | 73 |
| S3 RRK 8 | END/NSD | 83 | 72 | 72 |
| S3 RRK 9 | GSG | 83 | 68 | 58 |
| S3 RRK 10 | NDE/SDG | 85 | 73 | 74 |
| S3 RRK 12 | DNR/GDG | 62 | 58 | 83 |
| S3 RRK 14 | KGR | 85 | 72 | 72 |
| S3 RRK 15 | GKK/GKR | 80 | 71 | 76 |
| Negative control - no enzyme | N/A | 0 | 0 | 100 |

Enzyme variants with increased activity and preferred distributions are created by combining mutations identified in the results for the RRK variant and/or the catalytic dyad evaluations. As such, the beneficial E142A and E804A amino acid substitutions were added to the combinations identified at positions corresponding to, C206, G204, C205, and V208 in the RRK variant study above.

Example 4: Production of Siamenoside I; Purification of Siamenoside I from Crude Material Via Bioconversion of Mogroside V: Scaled Processes for Bioconversion As enzyme stability is influenced by higher temperatures and pH, conditions were sought to concentrate enzyme, limit the reaction times and improve purification methods. In addition, this had the added benefit of limiting potential for bacterial contamination growth. A general flow of a scaled bioconversion process is shown diagrammatically in FIG. 6.

A) General Process Flow and Reactor Preparation Prereactor

Figure 6:
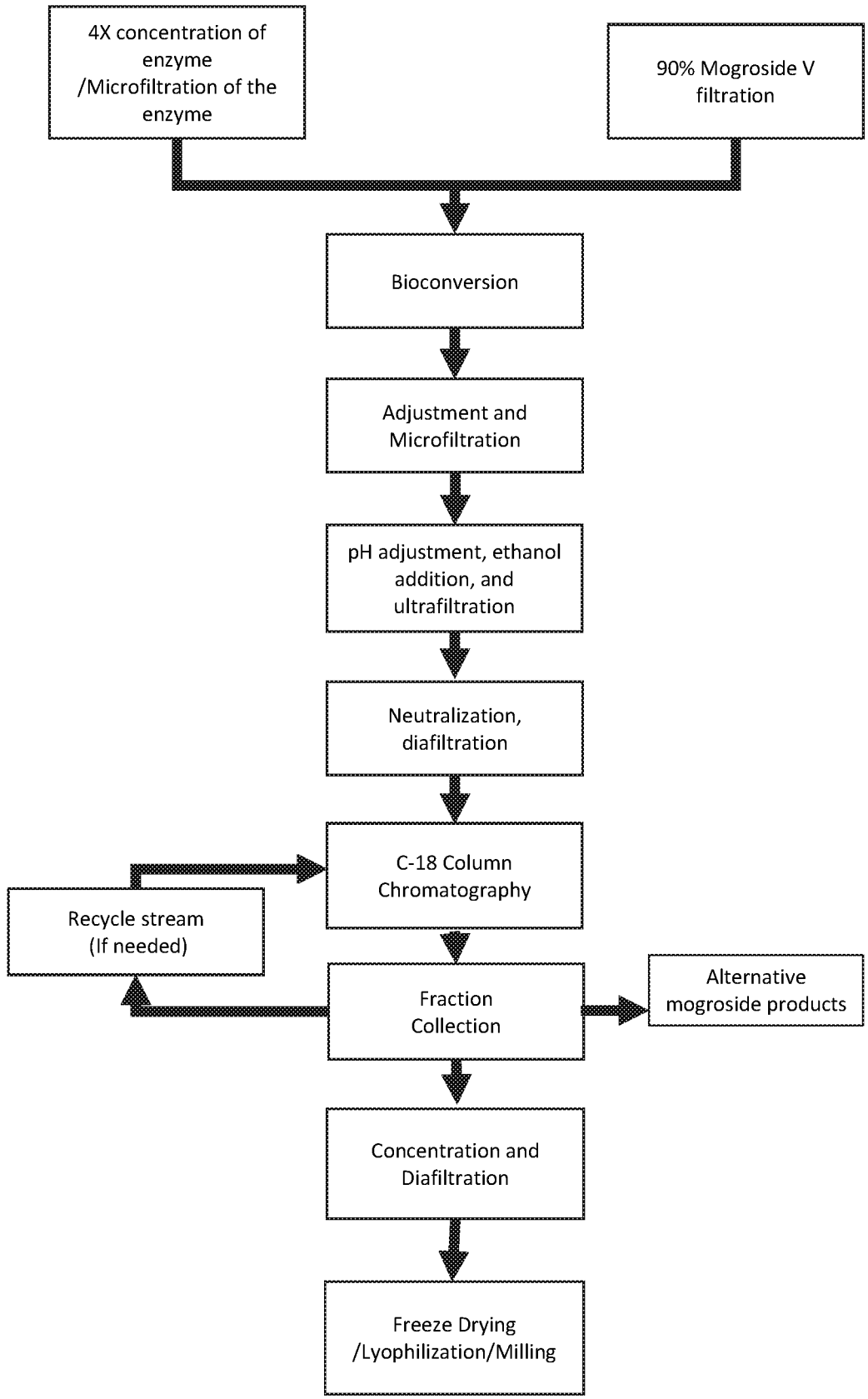
FIG. 6 provides schematic showing a general production flow of a scaled bioconversion process.

The Maxilact enzyme was concentrated using a hollow fibre membrane, Koch 6043-PM5 Romicon 5 kDa. The enzymatic solution was processed in a batchwise configuration. A flexible blade pump was used to reduce the shear stress on the enzymes. The pressure at the inlet was kept below 2.5 barg. The permeate containing glycerol, salts and water was discarded. (FIG. 6)

The Mogroside V 90 powder was mixed with UV treated RO water using a stirrer. After the powder was in solution, Acetic Acid, Sodium Acetate, Magnesium Chloride hexahydrate and Sodium Hydrogen Biphosphate was dissolved into the solution. Final reaction concentrations for Sodium acetate, sodium phosphate and magnesium chloride are 35 mmol, 35 mmol and 2.14 mmol respectively. The pH was adjusted to 6.3 using the 79% acetic acid.

The Mogroside solution was filtered using the 0.2 mm hollow fibre filter. The concentrated enzyme solution was then filtered through the same 0.2 mm hollow fibre filter. The purpose was to reduce the particulate for easier sterilization filtration.

Reactor

The reactor was sterilized using 1 barg steam for 30 minutes. A sterilized connection was made using a Saortobran 0.22 filter, with the connection made in a laminar flow cabinet.

The Mogroside solution was pumped through the Sartobran 0.22 filter, followed by the enzyme solution. This was to avoid the Mogroside binding to enzyme prior to filtration, and potentially being removed by the filter.

The stirred reactor (30 rpm, Rushton agitator) was kept sterile, and under a 2-4 psig positive pressure with sterilized air. The reaction conditions were about 54° C. The reaction was stopped at day 12, with 8.9% Mogroside V, and 63% Siamenoside I B) Specific Example Process Preparing the Mogroside V+Buffer Solution Ca. 140 L of concentrated, sterile filtered Maxilact A4 and 5 kg of Mogroside V (Lot #PRF8113001), dissolved in ~45 L of 50 mM phosphate buffer (pH 6.5), were transferred successively and aseptically to the fermenter. After warming the contents to 50° C., the pH was adjusted to 6.2. pH was maintained at 6.2 by periodic additions of sterile 1N NaOH solution Bioreactor Preparation and Operation:

A 650 L fermentation vessel was pre-sterilized. Sterilization filter (Sartobran 0.22 filter) was connected to the fermentation tank using sterile technique. The Mogroside V+Buffer Solution added first to the vessel, followed by 5 kg of UV RO water as a rinse. Next, the Maxilact solution was added into the vessel, followed by 3 kg of UV RO water as a rinse (note that about 2.5 L of this rinse stays in the lines and doesn't make it to the Vessel).

The vessel was set to a bioreactor temperature of about 54° C., the operation pressure of the reactor was set to +5 psig, and the agitator rotation speed was set at 30 rpm. The reaction was monitored about every 24-72 hours until reaction was considered complete, which was when the mogroside V concentration was about 10% or less.

Figure 7:
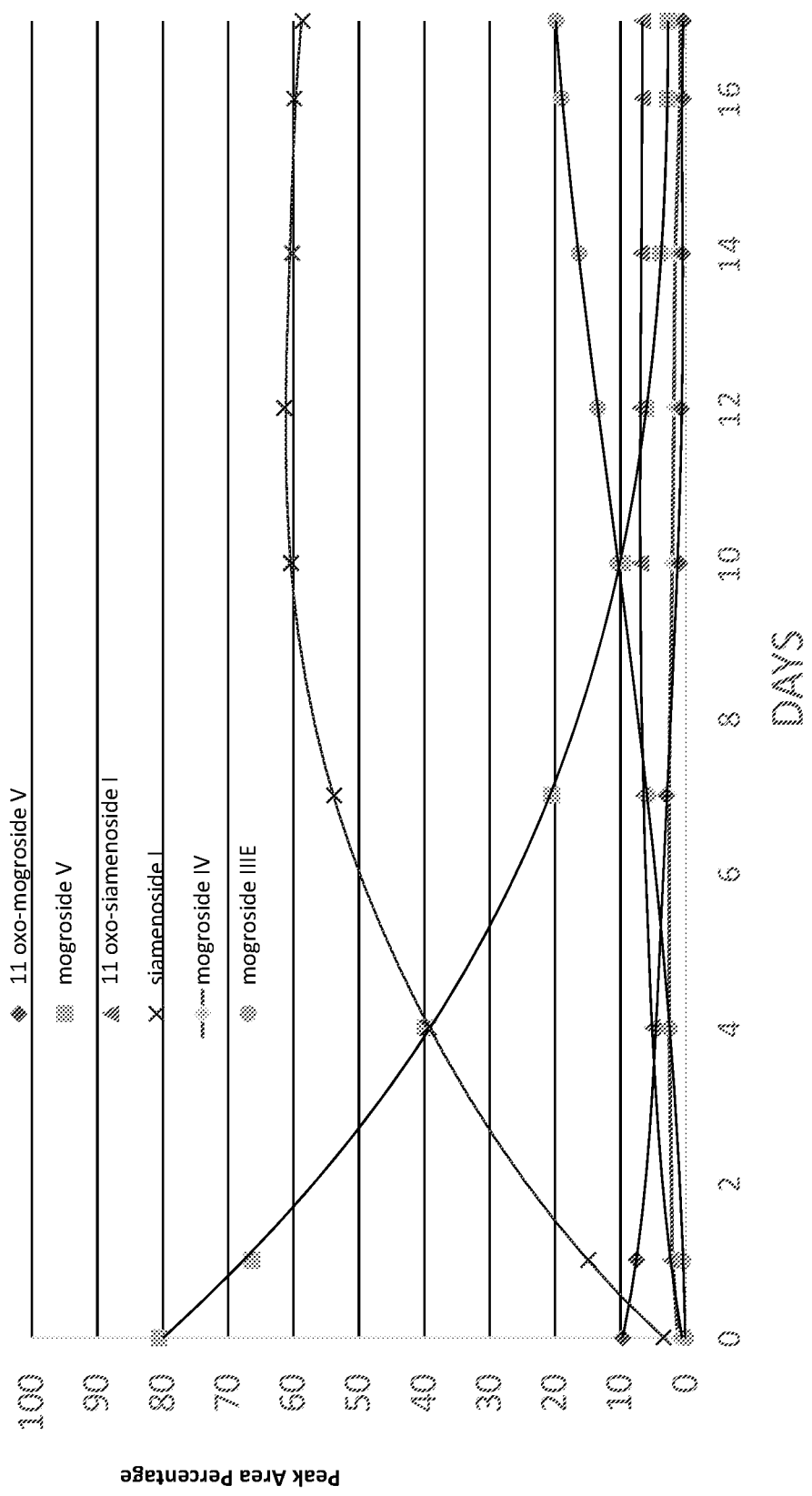
FIG. 7 provides a graph showing the reaction profile for a 5 kg scale up reaction FIG. 8 provides a flow chart showing hydrolysis of mogroside V to Siamenoside I: downstream flow to create a semi-purified crude reaction mixture from crude reaction mixture and the secondary purification of the semi-purified crude mixture into a highly purified siamenoside I ingredient (via Chromatorex SMB C18, distillation, and freeze drying)

Reaction progress was monitored by analysis of reaction mixture at several time points and is shown in Table 10 and FIG. 7.

After 7 days, the reaction was cooled to ambient and purified

| | | | | % weight | | | |
|---|---|---|---|---|---|---|---|
| Time (Days) | Mog. V | Sia. I | Mog. IV | Mog. IIIE | Total Conversion | Mog. IV + Mog IIIE | Ratio (Sia. I/Products) |
| 1 | 62% | 26% | 9% | 4% | 41.2 | 13.9 | 0.66 |
| 2 | 43% | 44% | 7% | 6% | 60.3 | 14.5 | 0.76 |
| 4 | 16% | 66% | 6% | 12% | 85.6 | 19.9 | 0.77 |
| 5 | 9% | 70% | 5% | 16% | 92.4 | 23.2 | 0.75 |
| 6 | 6% | 72% | 0 | 22% | 94.9 | 24.5 | 0.74 |
| 7 | 6% | 71% | 0 | 24% | 95.2 | 26.7 | 0.72 |

The incubation conditions are within a narrow/optimal pH and temperature window above 40° C. to 60° C. and pH above 6 to 7 or 7.5. In one example, the mogroside conversion product has a mogrol glycoside distribution as follows: mogroside V 0 to about 40% by weight, mogroside IV 0 to about 15% by weight, mogroside IIIE 0 to 30% by weight, and Siamenoside I 60 to about 99% by weight, wherein the weight percentages are based on the total mogrol glycoside content of the modified fruit extract and wherein the amount of at least one of mogroside V, mogroside IV, mogroside IIIE or Siamenoside I is greater than 0% by weight.

(Define as (([Total mogroside V weight added]−[Final Mogroside V weight])/100) to other mogrosides, where the siamenside weight content is between 60%-99% of the Total Mogroside. (Defines as: Total Mogroside=(Mog V+Mog IV+Sia I+Mog IIIE)) and the mogroside V weight content is between.

Example 5: Small Scale Purification

Small Scale Purification of crude reaction mixtures was accomplished using Waters XBridge Phenyl column systems with HPLC analysis at stages during the purification process.

1. Materials and Methods

The material used for the isolation of Siamenoside I [Lot #KTC-B-123(1)] was a Mogroside sample of a mixture of mogroside V (40 mg) and Maxilact A4 (0.8 mL; DSM, Lot #615495651) in sodium acetate buffer (pH 6; 2 mL) was stirred at 50 degree for 7 days and heated at 80 degree for 20 min and then cooled.

Reference standards Siamenoside I lot #PRF 8050402 and Mog IVa lot #MS16021403 were also used.

2. HPLC Analysis.

HPLC analyses were performed on a Waters 2695 Alliance System coupled to a Waters 996 Photo Diode Array (PDA) detector. In addition, sample purities were assessed using an ESA Corona Plus Charged Aerosol Detector (CAD). Sample analyses were performed using the method conditions described in Table 11.

TABLE 11

Analytical HPLC Conditions for Fraction Analysis in Primary, Secondary Process and Final Purity Analysis.

| Parameter | Description |
|---|---|
| Column (Dimensions) | Waters XBridge Phenyl |
| Column Temperature (° C.) | Ambient |
| Sample Temperature (° C.) | Ambient |
| Mobile Phases | (A) Water |
| | (B) Acetonitrile (MeCN) |
| Flow Rate (mL/min) | 1.0 |
| Detection | UV at 210 nm and CAD |

| Gradient | | |
|---|---|---|
| Time (min) | % A | % B |
| 0.0-40.0 | 80 | 20 |
| 40.01-47.0 | 10 | 90 |
| 47.01-57.0 | 80 | 20 |

3. Primary Preparative HPLC Method

The primary processing of the sample was performed using a Waters XBridge Phenyl column (19×250 mm, 5 μm). The purification process was performed using a Waters Delta Prep 2000/4000 system coupled to a Waters 2487 UV-Vis detector. Details of the preparative methods are summarized in Table 12.

TABLE 12

Conditions for primary preparative HPLC method

| Parameter | Description |
|---|---|
| Column (Dimensions) | Waters XBridge Phenyl (19 × 250 mm, 5 μm) |
| Flow Rate (mL/min) | 118.0 |

TABLE 12-continued

Conditions for primary preparative HPLC method

| Parameter | Description |
|---|---|
| Detection | UV at 210 nm |
| Mobile Phases | (A) 80:20 Water/MeCN |
| | (B) 10:90 Water/MeCN |
| Sample Preparation | ~1.0 mL of sample was syringe filtered into 2.0 mL of Acetonitrile then diluted up to 10 mL with water. (see 4.1) |
| Gradient | Isocratic hold of 100% MP-A for 40 min, then 20 min flush of 100% MP-B |

4. Secondary Preparative HPLC Method

The secondary processing was performed using a Waters Xbridge Phenyl (19×250 mm, 5 µm). The purification process was performed using a Waters 2545 Quaternary Gradient Module system coupled to a Waters 2489 UV-Vis detector. Details of the preparative method are summarized in Table 13.

TABLE 13

Conditions for Secondary Preparative HPLC Method.

| Parameter | Description |
|---|---|
| Column (Dimensions) | Waters XBridge Phenyl (19 × 250 mm, 10 µm) |
| Flow Rate (mL/min) | 118.0 |
| Detection | UV at 210 nm |
| Mobile Phases | (A) 80:20 Water/MeCN |
| | (B) 10:90 Water/MeCN |
| Sample Preparation | 10.0 mL |
| Gradient: | Isocratic hold of 100% MP-A for 40 min, then 20 min flush of 100% MP-B |

Primary Purification: Approximately 1 mL of the sample was processed using the primary preparative HPLC method described in Table 12. Fractions were analyzed using the analytical method summarized in Table 11. Sample was received in approximately 0.3 mL of Glycerol. To minimize Glycerol contamination, the sample was syringe filtered, then mixed with organic solvent (Acetonitrile) and diluted up to 10 mL Water. Glycerol contamination was noted as an issue in primary processing, in this case it resulted in Fractions of interest eluting in the Flush. Collected fraction Lot #KTC-B-115(Flush) was selected for reprocessing.

Secondary Purification: Fraction Lot #KTC-B-115(Flush) was reprocessed using the conditions described in Table 12. Fractions were analyzed using the analytical method summarized in Table 10. Collected fraction KTC-B-123(1), retention time approximately 13.947 min on the respective preparative HPLC trace, was deemed sufficiently pure for structural elucidation via NMR Final Batch Preparation: Fraction Lot #KTC-B-123(1)) was concentrated by rotary evaporation and further dried via lyophilization for 24 hours. The final yield of the batch KTC-B-123(1) was 1.4 mg. The final purity was determined using the analytical method summarized in Table 10 and found to be 97.09% (AUC, CAD) with a retention time of 13.632 min; the analysis is provided in FIG. 6. Reference Siamenoside I was run in sequence with KTC-B-123(1), retention time was 13.561 min.
Method Conditions
    Column: Phenyl Xbridge (4.6×150 mm, 3.5 um)
    Temperature: Ambient
    Method: 80/20 Water/MeCN, 20 min Isocratic hold.
    Detection: CAD, UV @210 nm

TABLE 14

Purity Analysis from Small-scale Secondary Purification

| Siamenoside I Lot # | RT (mins) | Purity (Area %) CAD | Purity (Area %) UV |
|---|---|---|---|
| KRI-AG-121-8 | 11.368 | 93.2 | 94.6 |
| KRI-AG-122-8 | 11.832 | 95.1 | 98 |
| KRI-AG-123-5 | 11.631 | 96.3 | 98 |
| KRI-AG-124-8 | 11.509 | 97.0 | 99.1 |
| KRI-AG-125-8 | 11.338 | 97.6 | 99.1 |

Example 6: Purification of Large Scale Preparations

Figure 8:
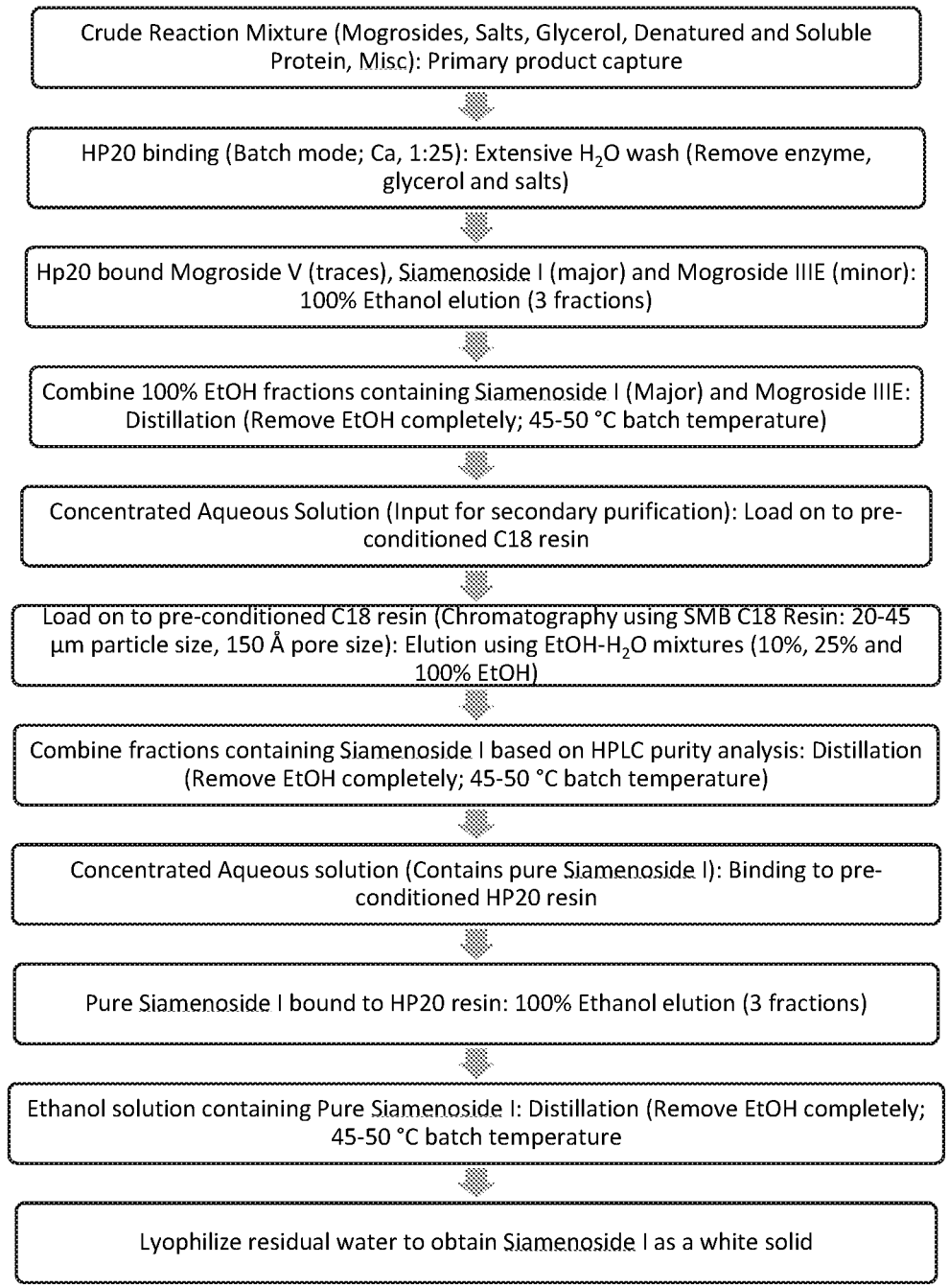

A general purification scheme is shown in FIG. 8.
Method:
As shown in FIG. 8, crude reaction mixture was mixed at room temperature as a batch with HP20 resin Ca. The reaction mixture was mixed (overhead agitation) with resin for ~1 hour. HP20 resin was added at 25× to 30× (w:w) amount of the mogroside content of the reaction mixture. The HP20 bound Mogrosides were loaded into a polypropylene SPE cartridge and washed with water to remove enzyme and related impurities. The water wash had minor quantities of Sia. I as seen from HPLC analysis. Elution of Mogrosides from HP20 resin was tested using 100% organic solvents (methanol, acetone, acetonitrile, and ethanol). The goal of the study was to elute all the Mogrosides in a minimal volume of solvent. Using higher amounts of organic solvents for elution would also facilitate downstream concentration and purification.
Result:
Elution of bound product(s) from HP20 resin was tested using 100% organic solvents (Acetone, Acetonitrile & Methanol; Reverse elution order). The goal of the experiments was to elute the products in lower volumes and higher organic solvent concentrations

TABLE 15

Elution of bound Mogrosides from HP20 resin (10 g) using 100% organic solvents

| | Sia. I (Estimated)[r] | | |
|---|---|---|---|
| Sample ID | Volume (~, mL) | Concentration (mg/mL) | Amount (mg: Estimated) |
| 100% MeOH elute-1 | 40 | 7.076763 | 283.1 |
| 100% MeOH elute-2 | 40 | 0.33903 | 13.6 |
| 100% Acetone elute-1 | 40 | 5.769018 | 230.8 |
| 100% Acetone elute-2 | 40 | 0.325773 | 13.0 |
| 90% Acetone elute-1 | 40 | 0.679039 | 27.2 |
| 90% Acetone elute-2 | 40 | 0.475821 | 19.0 |
| 80% Acetone elute-1 | 40 | 0.2177445 | 8.7 |
| 100% ACN elute-1 | 40 | 3.268182 | 130.7 |
| 100% ACN elute-2 | 40 | 0.252242 | 10.090 |
| 80% ACN elute-1 | 40 | 1.350649 | 54.026 |
| 80% ACN elute-2 | 40 | 0.672599 | 26.904 |

[r]Based on standard curve using Sia. I reference standard (95% purity; lot# CDXP-17-0042) 100% Methanol (Table 1) or 100% Ethanol were found to be appropriate for complete elution of products from HP20 resin in minimal volumes (approximately 2 volumes:weight resin).

TABLE 16

Elution of bound Mogrosides from HP20 resin (100 g) using 100% Ethanol

| Elute Id | Lot# | Volume (mL) | Sia. I (Estimated)[r] | |
|---|---|---|---|---|
| | | | Concentration (g/L) | Total Amount (g) |
| 100% EtOH elute-1 | KRI-AG-115-1 | 200 | 12.75 | 2.55 |
| 100% EtOH elute-2 | KRI-AG-115-2 | 200 | 1.61 | 0.32 |
| 100% EtOH elute-3 | KRI-AG-115-3 | 200 | 0.29 | 0.06 |
| 90% EtOH elute-1 | KRI-AG-115-4 | 200 | 0.16 | 0.03 |

[r]Based on standard curve using Sia. I reference standard (95% purity; lot# CDXP-17-0042)

This method can be applied to Large scale bioconversion of Mogroside V 340 g of Mog. V was dissolved in 1 L of potassium phosphate buffer (100 mM, pH 6.5) and diluted with 1 L of water (total 2 L with a final buffer concentration of 50 mM). This was then filtered through a 0.2 μm sterile filter unit.

6 L of recently concentrated Maxilact A4 (3.5× concentrated) was diluted with 6 L of buffer (potassium phosphate 100 mM, pH 6.5) and the pH of the diluted enzyme was adjusted to ~6.0. 1% of filter aid (Celite; w/v) was added and the suspension mixed for ~15 minutes. The suspension was then filtered over a tub equipped with a coarse frit. The filtrate was passed through a series of capsule filters (5 μm and 0.2 μm) before final filtration in to sterile filtration units. The final volume of filtered enzyme was ~11 L.

11 L of sterile filtered enzyme and 2 L of sterile Mog. V solution was independently transferred to the fermenter. The pH was adjusted to 6.2 and the reaction temperature was adjusted to 50° C. and the reaction initiated.

No significant pH changes or microbial contamination was observed during the course of the reaction. However, higher amounts of turbidity/clouding were observed as compared to previous reactions, possibly due to higher enzyme concentration resulting in increased enzyme denaturation.

Samples were withdrawn at regular time intervals and analyzed for conversion to Siamenoside I.

Details of the reaction progress are shown in Table 17.

TABLE 17

Results from the 3rd engineering batch of reaction (Lot#KRI-AG-103) conducted in Sterile 20 L Fermenters

| | % AUC (200 nm) | | | | | | | |
|---|---|---|---|---|---|---|---|---|
| Time (Days) | Mog. V | Sia. 1 | Mog. IV | Mog. IIIE | Misc. | Total conversion | Mog. IV + Mog IIIE | Ratio (Sia I/ Products) | Sia. I (Estimated) (g) |
| 0.5 | 81.2 | 15.2 | 3.6 | 0 | 0 | 18.8 | 3.6 | 0.81 | 53.61 |
| 1 | 72.4 | 24.3 | 3.4 | 0 | 0 | 27.7 | 3.4 | 0.88 | 77.14 |
| 2 | 53.1 | 38.9 | 4.4 | 3.9 | 0 | 47.2 | 8.3 | 0.82 | 119.43 |
| 3 | 36.9 | 52.3 | 5 | 5.8 | 0 | 63.1 | 10.8 | 0.83 | 137.77 |
| 4 | 24.5 | 65.3 | 3.9 | 6.2 | 0 | 75.4 | 10.1 | 0.87 | 174.69 |
| 5 | 16.3 | 71.2 | 2.5 | 10 | 0 | 83.7 | 12.5 | 0.85 | 199.99 |
| 6 | 9.7 | 73.7 | 2.5 | 14.2 | 0 | 90.4 | 16.7 | 0.82 | 198.13 |
| 7 | 5.5 | 77 | 0 | 17.5 | 0 | 94.5 | 17.5 | 0.81 | 191.39 |
| 8 | 3.1 | 76.8 | 0 | 20.1 | 0 | 96.9 | 20.1 | 0.79 | 190.31 |
| 8.5 | 2.3 | 74.3 | 0 | 23.5 | 0 | 97.8 | 23.5 | 0.76 | 185.99 |

Amounts of Siamenoside I in the reaction was estimated based on standard curve using reference standard (95% purity).

Large scale elution of Mogrosides from HP20 resin using methanol

Reaction mixtures were processed in batches. The reaction mixture was mixed (overhead agitation) with resin for ~1 hour. HP20 resin was added at 25× to 30× (w:w) amount of the mogroside content of the reaction mixture. The bound resin was washed with water to remove enzyme and related impurities. The elution using 100% methanol was scaled up using 2.5 Kg of bound HP20

Results are shown in Table 18. As seen from the table, the Mogrosides are completely eluted from the resin using ~2 volumes of 100% methanol.

TABLE 18

Elution of bound mogrosides from 2.5 kg of HP20 resin

| | | Sia. I (Estimated) | |
|---|---|---|---|
| Sample ID | Volume (~L) | Concentration (g/L) | Total amount (g) |
| 100% MeOH elute-1 | 4.8 | 15.4 | 74 |
| 100% MeOH elute-2 | 4.8 | ND | ND |
| 100% MeOH elute-2 | 4.8 | ND | ND |
| 100% MeOH elute | 4.8 | ND | ND |

Method:

Eluent from the HP20 purification step was prepared for further chromatography. The ethanol-containing fractions were pooled and ethanol was removed completely by distillation 45-50° C. batch temperature. The remaining aqueous solution was further concentrated and the non-saturating portion of the concentrated solution was loaded onto a C18 resin (Chromatorex SMB 150, 20-45 μm) column. Elution of purified Siamenoside I and mogroside IIIE peaks were evaluated by elution with increasing steps of either methanol or ethanol concentrations, respectively.

Figure 9A:
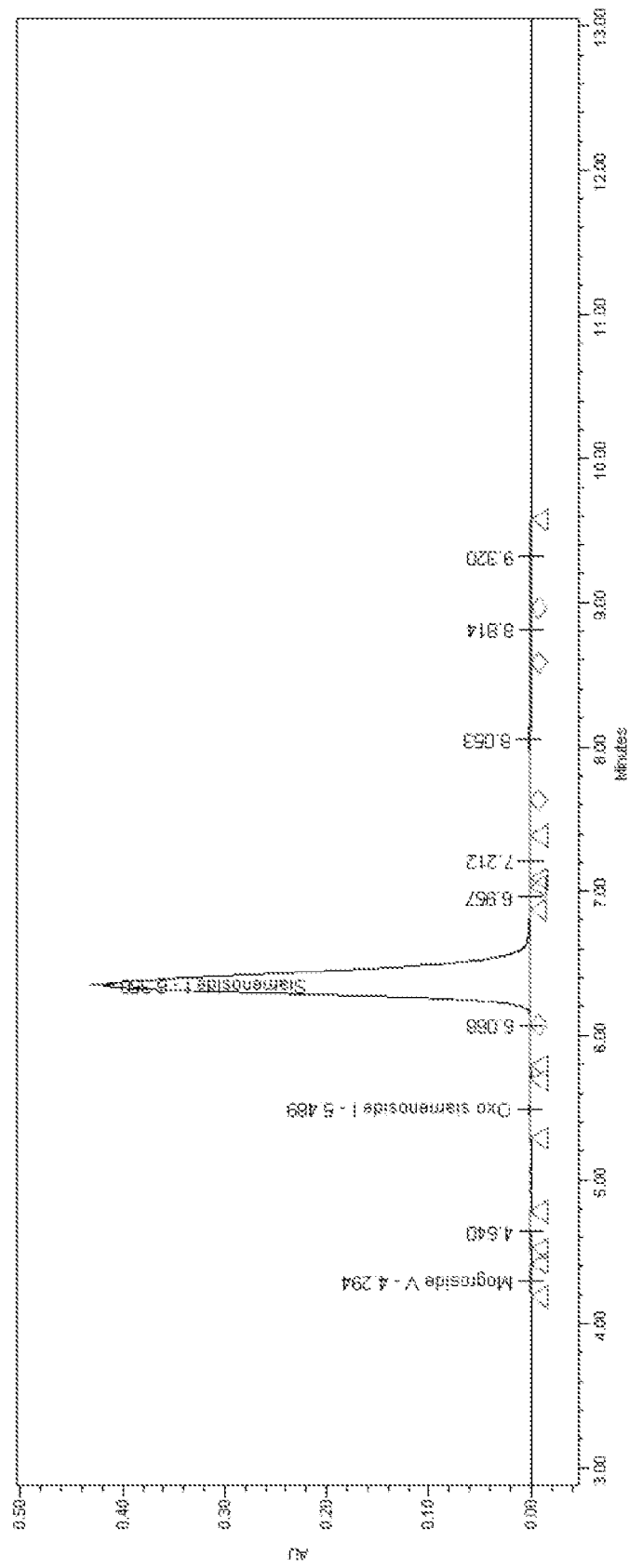
FIGS. 9A and 9B provides graphs showing HPLC analysis of pure fractions.
Figure 9B:
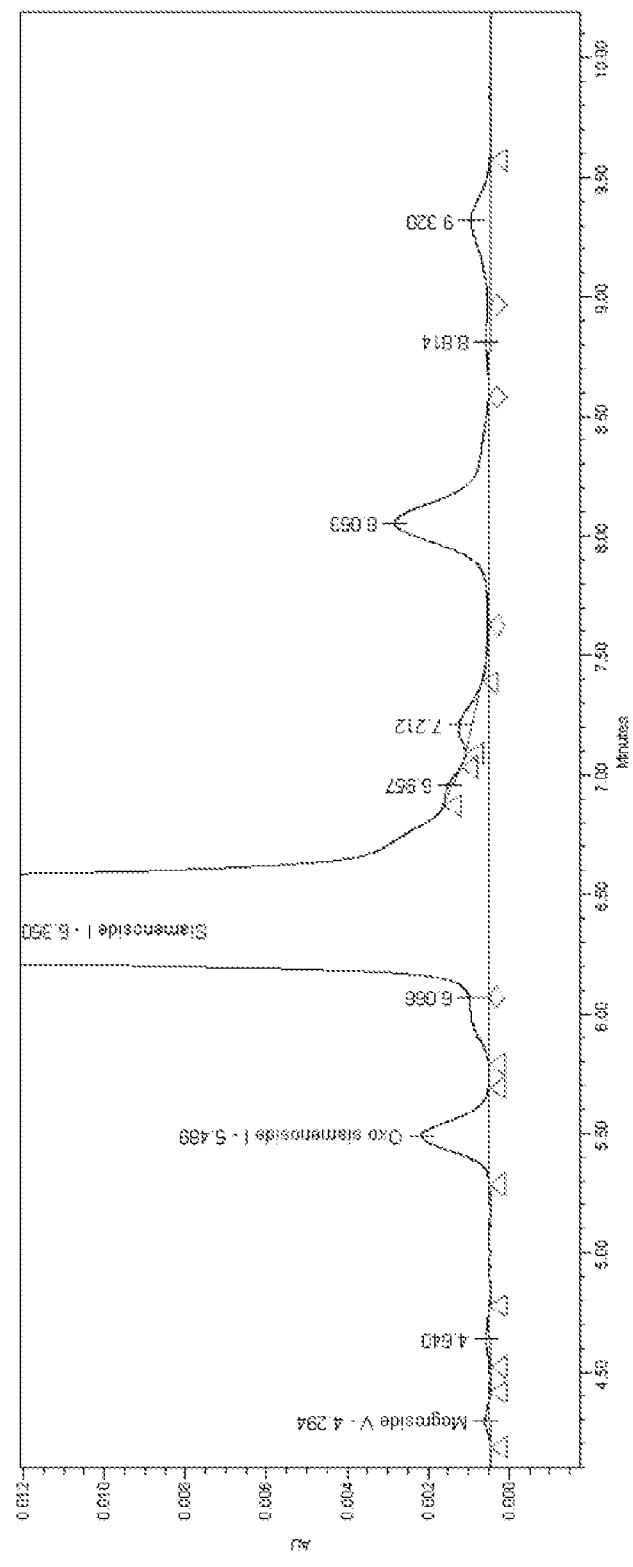
Figure 10:
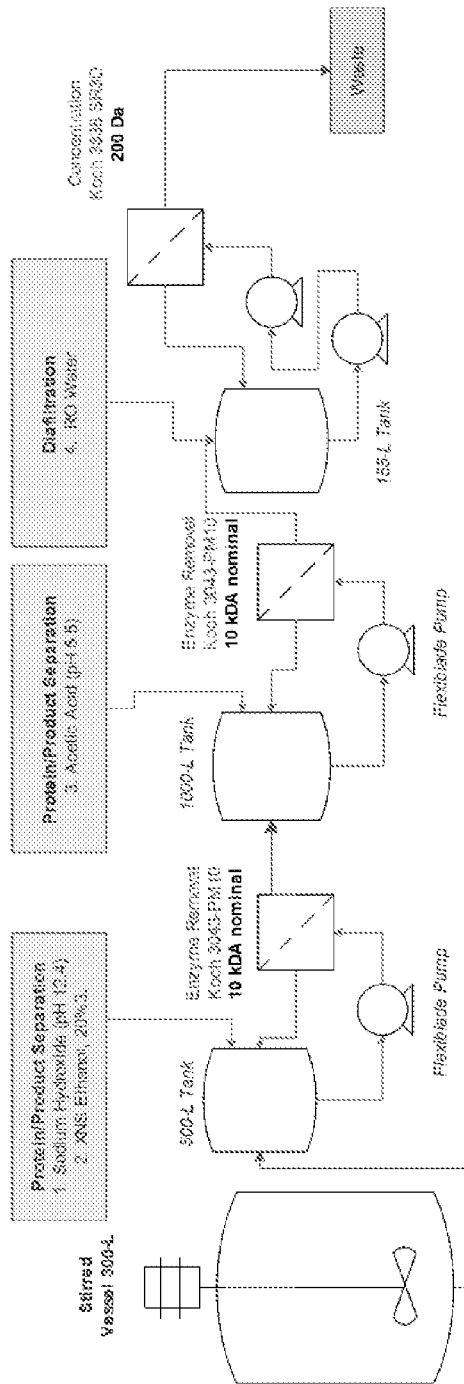
FIG. 10 provides a process flow diagram of the post reaction purification.

Results for methanol are shown in Table 19 for Siamenoside I elution and FIG. 9.

TABLE 19

Elution profile of Siamenoside I from secondary purification of Siamenoside I (C18 chromatography) using methanol-water mobile phase.

| Sample ID | Volume (~mL) | Sia. I Concentration (mg/mL) | Total amount (mg) | % Total amount | Purity (% AUC, 200 nm) |
|---|---|---|---|---|---|
| 25% MeOH elute-1 | 38 | 1.25 | 47.44 | 8.25 | 80.7 |
| 25% MeOH elute-2 | 38 | 1.68 | 63.95 | 11.12 | 93 |
| 30% MeOH elute-1 | 38 | 1.68 | 67.12 | 13.75 | 97 |
| 30% MeOH elute-2 | 38 | 1.33 | 53.30 | 10.92 | 98 |
| 30% MeOH elute-3 | 38 | 0.87 | 34.8 | 7.13 | >98 |
| 35% MeOH elute-1 | 38 | 1.28 | 51.16 | 10.48 | >98 |
| 35% MeOH elute-2 | 38 | 1.22 | 48.95 | 10.03 | >98 |

TABLE 19-continued

Elution profile of Siamenoside I from secondary purification of Siamenoside I (C18 chromatography) using methanol-water mobile phase.

| Sample ID | Volume (~mL) | Sia. I Concentration (mg/mL) | Total amount (mg) | % Total amount | Purity (% AUC, 200 nm) |
|---|---|---|---|---|---|
| 35% MeOH elute-3 | 38 | 0.89 | 35.47 | 7.27 | >98 |
| 35% MeOH elute-4 | 38 | 0.74 | 29.54 | 6.05 | >98 |
| 40% MeOH elute-1 | 38 | 1.16 | 46.47 | 9.52 | >98 |
| 40% MeOH elute-2 | 38 | 1.08 | 43.03 | 8.82 | 97 |
| 40% MeOH elute-3 | 38 | 0.73 | 29.11 | 5.96 | 88 |
| 40% MeOH elute-4 | 38 | 0.42 | 16.65 | 3.41 | 52 |
| 50% MeOH elute-1 | 38 | 0.59 | 23.87 | 4.89 | 21 |
| 50% MeOH elute-2 | 38 | 0.23 | 9.33 | 1.91 | 7.6 |
| 50% MeOH elute-3 | 38 | ND | | | |
| 100% MeOH elute-1 | 38 | ND | | | |
| 100% MeOH elute-2 | 38 | ND | | | |

Results for methanol are shown in Table 20 for Siamenoside I elution

Siameneoside I can be separated from other mogrosides in this mixture with greater than 95% purity with a methanol concentration between 30% and 40%.

Mogroside IIIE can be separated from other mogrosides in this mixture with greater than 95% purity with a methanol concentration between 50% and 100% methanol.

TABLE 20

Elution profile of Sia. I from secondary purification of Sia. I (C18 chromatography) using methanol-water mobile phase.

| Sample ID | Volume (~L) | Resin Volume | Sia. I Concentration[t] (g/L) | Total Amount (g) | % Total Amount | Purity (% AUC, 200 nm) |
|---|---|---|---|---|---|---|
| Load Passthro | 0.6 | 1.2 | 0.77 | 3.99 | 13.8 | 90.6 |
| 10% EtOH-1 | 5.2 | 10.4 | 0.56 | 1.11 | 3.9 | >97 |
| 10% EtOH-2 | 2 | 4 | 0.46 | 0.93 | 3.2 | >97 |
| 10% EtOH-3 | 2 | 4 | 3.98 | 19.92 | 68.9 | 99 |
| 25% EtOH-1 | 5 | 10 | 0.92 | 0.92 | 3.2 | 96.8 |
| 25% EtOH-2 | 1 | 2 | 0.71 | 0.71 | 2.4 | 95.2 |
| 25% EtOH-3 | 1 | 2 | 0.44 | 0.44 | 1.5 | 56.3 |
| 25% EtOH-4 | 1 | 2 | 0.25 | 0.25 | 0.9 | 24 |
| 25% EtOH-5 | 1 | 2 | 0.32 | 0.65 | 2.2 | 2 |
| 100% EtOH-1 | 2 | 4 | 0.77 | 3.99 | 13.8 | 90.6 |

[t]Estimates are based on standard curve using Sia. I reference standard;
HPLC peak area integrations may not be accurate due to jagged baseline at 200 nm;
ND = Not Detected Total recovery of Sia. I = 28.9 g (~90%);
Recovery of Sia. I with purity above 96% = 22.8 g (79.2%);
Total volume of fractions containing pure Sia. I = 10 L (20 RVs)

Example 7: Purification of Mogrosides from Reaction Mixtures with C18 Resin

Figure 11:
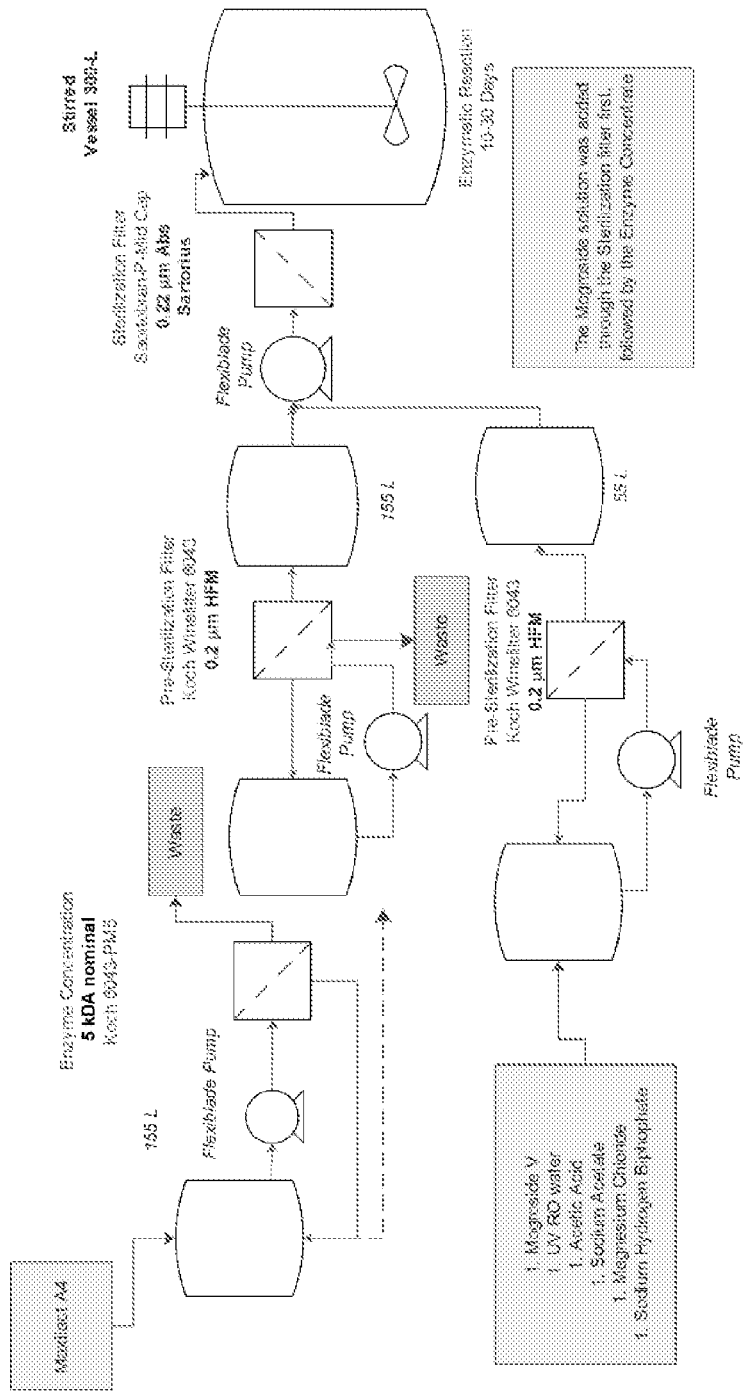
FIG. 11 provides a diagram showing a general flow of a scaled bioconversion process.
Figure 12:
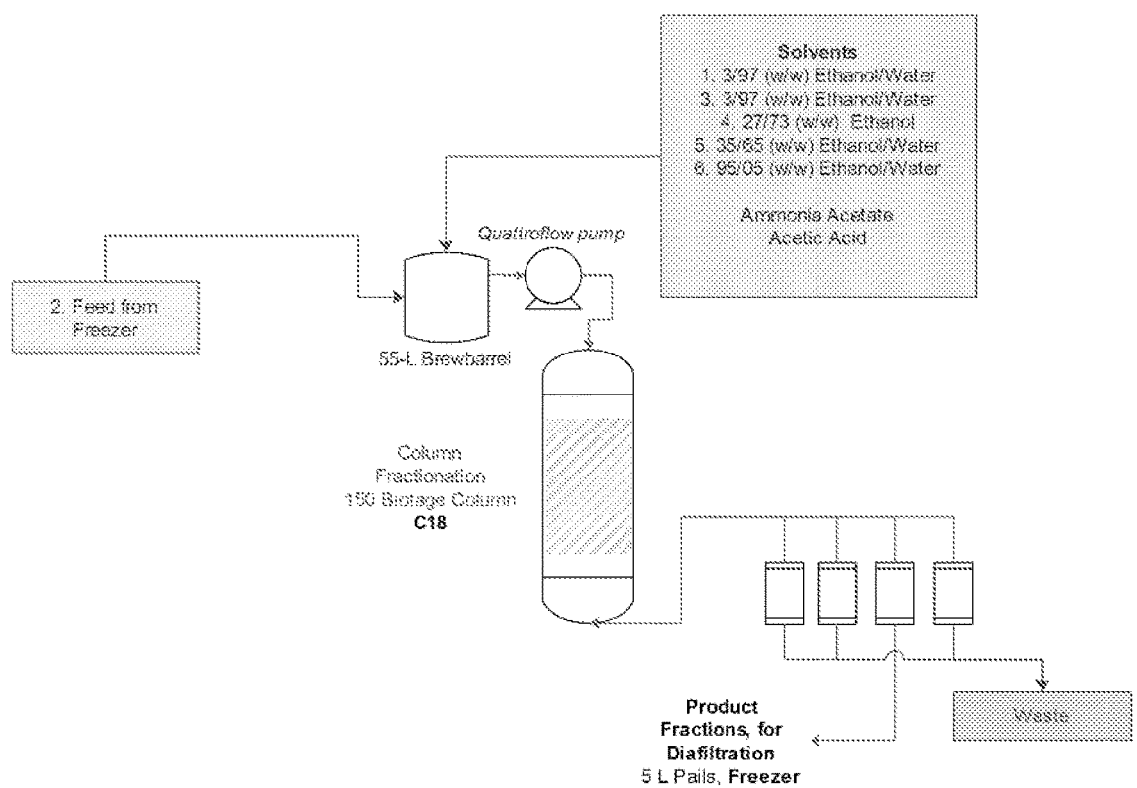
FIG. 12 provides a process flow diagram of chromatography.
Figure 13:
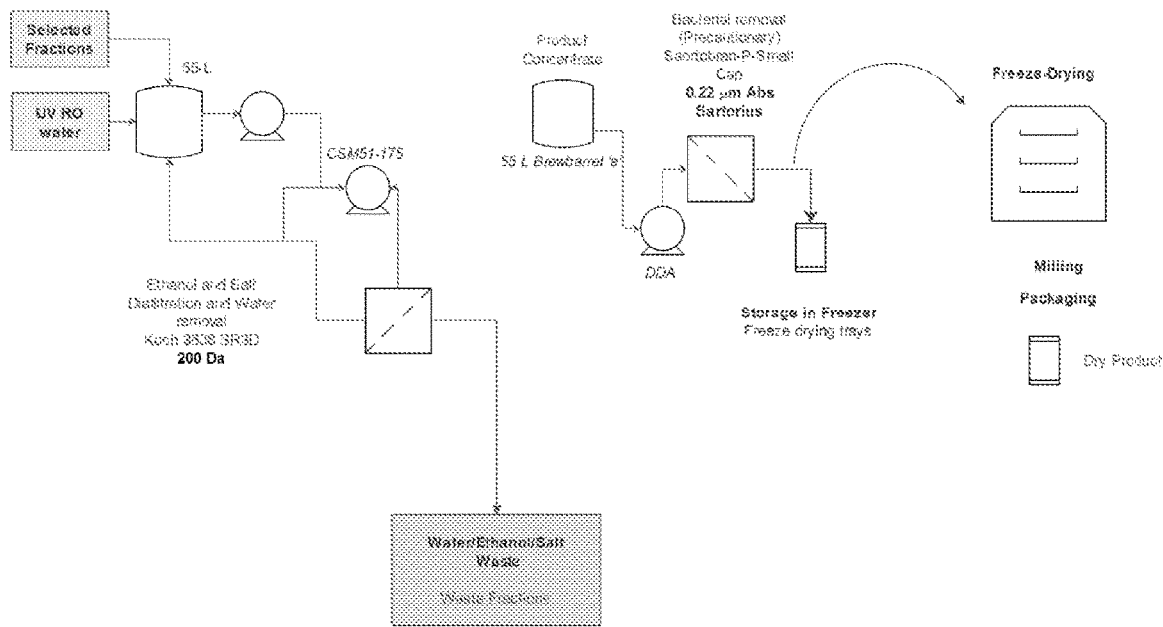
FIG. 13 provides a process flow diagram of diafiltration and finishing.

A purification scheme is shown diagrammatically in FIGS. 11-13.

Post-Reactor

After the conversion reactions, the mogrosides must be separated from the enzyme and salts. In order to separate the protein from the mogroside, the reaction mixture was mixed with sodium hydroxide, increasing the pH to 12.4. Ethanol was added making a 20% ethanolic solution. The mixture was filtered through a 10 kDa Koch Romicon membrane, with a 1.7 barg inlet pressure, and atmospheric at the outlet. The pH of the permeate was lowered to 5.5 using acetic acid and cooled overnight. The next day the solution was refiltered through a 10 kDa Koch Romicon membrane.

The water, ethanol and salts were removed using a nanofiltration membrane Koch SR3D with a 200 Da cutoff. The inlet pressure was 12 barg, operating with a 0.6 bar pressure drop. The solution was diafiltered until the ethanol concentration was less than 3 percent, and was concentrated to 20-30 L. The concentrated mogrosides was mixed with water/Ammonia Acetate solution, making the solution up to ~110 L.

Preparation

The mixture was passed through a Biotage SNAP KP-C18-HS 400 g guard cartridge. The resulting solution was mixed and aliquoted into a 5 L HDPE jerry cans, as 1 column charge per jerry can. Each charge contained ~69 g of Siamenoside I. The charges were either used fresh or frozen at −15° C.

Chromatography

There are six stages for the chromatography separation:
1) equilibrize the column, to prepare for loading.
2) loading the column. The charge is followed by the small amount of Equilibration solution to distribute the mogrosides across the bed.
3) removal of the Mogroside V, and the other early eluting compounds. The first ~120 L is sampled and sent to waste. The next ~27 kg is collected, with the targeted purity occurring in the last fractions.
4) removal of the Siamenoside I, two large 18 kg fractions, followed by 4×4.5 kg fractions. The last fractions often miss purity specification.
5) straight XNS grade ethanol (95%). The first 18 kg is for the collection of Mog IIIe fraction.
6) straight XNS grade ethanol to clean the column.

The composition of the elutants are shown in Table 21.

TABLE 21

Column Eluent Mix

| | RO, 5 mMol NH$_4$Ac [w/w %] | Ethanol [w/w %] | Mass [kg] | Stage |
|---|---|---|---|---|
| Equilibria | 97.6 | 2.4 | 36.57 | Preparation |
| Load | 97.6 | 2.4 | 4.7 | Loading |
| Eluent pre Sia Collection | 77.4 | 22.6 | 120 + 27 | Mog V |
| Eluent during Sia Collection | 74.8 | 25.2 | 54 | Siamenoside |
| Ethanol Cleanup | 5.0 | 95.0 | 18 | Mog IIIE |
| | 5.0 | 95.0 | 10 | Waste |

TABLE 22

Column Eluent Mix

| Fraction No. | mass/ g | mL | Sia-I mg/ mL | Sia-I g | Sia-I Purity/ area % | Impurities/ area % | Total mass (assuming uniform UV response) | Total mass of included fractions | Sia-I included fractions | Purity* mass |
|---|---|---|---|---|---|---|---|---|---|---|
| 15 | 4518 | 4687 | 0.35 | 1.6 | 45.69 | 54.31 | 3.59 | 0.00 | 0.00 | 0.0 |
| 16 | 4521 | 4690 | 0.82 | 3.8 | 91.78 | 8.22 | 4.19 | 0.00 | 0.00 | 0.0 |
| 17 | 4576 | 4747 | 0.80 | 3.8 | 93.99 | 6.01 | 4.04 | 4.04 | 3.80 | 379.8 |
| 18 | 71500 | 74178 | 0.87 | 64.5 | 97.09 | 2.91 | 66.47 | 66.47 | 64.53 | 6453.5 |
| 19 | 4515 | 4684 | 0.14 | 0.7 | 92.53 | 7.47 | 0.71 | 0.71 | 0.66 | 65.6 |

Total Mass 71.2 g
Mass average purity 96.9%
Recovery 92.6%

Purity as assessed by peak area of greater than 96% was achieved.

Between 40 and 70 g of Siamenoside I with 96% purity was collected for each column run (about 5 L material loaded for each column run). Hydrolysis of Mogroside V to Siamenoside I: Secondary purification-Chromatorex SMB C18 is shown in FIG. 8.

Diafiltration

Fraction containing Siamenoside I of suitable purity were processed further. The fractions have to have the ethanol and ammonia acetate removed. Combined fractions are diafiltered and RO water is added to the solution to keep the ethanol concentration below 15%. The ammonia, acetate, ethanol and water was removed. The operating pressure will be 12 barg, with a 0.6 bar pressure drop. The solution was concentrated to ~50 L. RO Water was added in 10 L allocations, after each 10 L of permeate is collected. The RO water addition continues until the solution has a 1000× fold reduction in salt and ethanol concentration. Approximately 350-L of diafiltration water is required after concentration. The expected ammonia salt concentration is 0.2 ppm in the solution, or 10 ppm in the product.

Freeze Drying

The Siamenoside I concentrate was filtered through a 0.22 mm filter into Lyophilization trays. After freeze-drying, the trays are cut open and milled into a fine powder. The powder is packaged in a Nalgene bottle until use.

Example 8: Comparison of Select Engineered Enzymes for Improved Catalytic Activity and Specificity Standard mogroside biocatalytic assays were performed at 37° C. in 500 μL volume 50 mM sodium citrate buffer pH 5.6, 10 mM magnesium chloride, 10 mM substrate (typically mogroside V or Siamenoside I) and 50 μg mL−1 enzyme, and incubated for 24-96 hours. Mogroside glucosidation activity was detected by direct HPLC detection and quantification of mogroside V substrate and mogroside products from filtered reaction supernatant, and quantified by comparison with standard curves based on peak area (see Analytical Methods).

Analytical Method: Mogroside compounds HPLC separation and quantification was conducted using a Synergi Hydro-RP column (250 mm×4.6 mm or 150 mm×4.6 mm) with an initial flow rate of 1 mL min−1 and a water:acetonitrile gradient as per below, similar to that described by Zhou et al. (WO 2014/150127). Compounds were detected at 210 nm using diode array detector (Agilent Technologies, USA), and calibration curves established using standard curves from 0.1 to 10 mM. 150 mm column retention times in minutes: mog V 9.5, sia 1 10.6, mog IVa 10.5, mog IV 11.3, mog III 12.6, mogl I 13.2. 250 mm column retention times: mog V 12.3, sia 1 13.2, mog IVa 13.5, mog IV 14.1, mog III 15.3, mog II 16.2. The chromatography gradient is shown in Table 1.

TABLE 1

| Time (min) | A % | B % | Flow (mL/min) | Max Pressure Limit (bar) |
|---|---|---|---|---|
| 0.00 | 80.0 | 20.0 | 1 | 400 |
| 0.10 | 80.0 | 20.0 | 1 | 400 |
| 4.30 | 75.0 | 25.0 | 1 | 400 |
| 7.00 | 72.0 | 28.0 | 0.8 | 400 |
| 9.00 | 70.0 | 30.0 | 1 | 400 |
| 12.00 | 42.0 | 58.0 | 1 | 400 |
| 13.00 | 20.0 | 80.0 | 1 | 400 |
| 16.00 | 20.0 | 80.0 | 1 | 400 |
| 17.00 | 80.0 | 20.0 | 1 | 400 |
| 21.00 | 80.0 | 20.0 | 1 | 400 |

The biochemical characteristics of the selected variants are reported in Table 2:

TABLE 2

| Enzyme Variant | Mog V (as substrate) | | | Sia I (as substrate) | | |
|---|---|---|---|---|---|---|
| | $k_{cat}$ ($s^{-1}$) | $K_m$ (mM) | $k_{cat}/K_m$ ($s^{-1} mM^{-1}$) | $k_{cat}$ ($s^{-1}$) | $K_m$ (mM) | $k_{cat}/K_m$ ($s^{-1} mM^{-1}$) |
| wildtype | 751 ± 36 | 2.9 ± 0.3 | 259 | 35.8 ± 2.5 | 2.48 ± 1.0 | 0.56 |
| E142A | 741 ± 38 | 2.0 ± 0.4 | 371 | 3.9 ± 0.7 | 4.42 ± 0.9 | 0.88 |
| RRK67 | 1002 ± 112 | 1.5 ± 0.1 | 668 | 0.9 ± 0.1 | 0.44 ± 0.02 | 2.0 |
| E142A-RRK67 | 498 ± 24 | 0.5 ± 0.02 | 996 | 0.78 ± 0.08 | 1.5 ± 0.4 | 0.52 |
| D258E | 966 ± 26 | 2.5 ± 0.2 | 386 | 36.8 ± 3.1 | 3.31 ± 0.8 | 11.1 |

As a general trend, increased catalytic efficiency (kcat/Km) towards mogroside V and decreased catalytic efficiency towards Siamenoside I resulted in the improved Siamenoside I yields, when comparing Table 2 (above) to results in Table 3 (below), respectively.

TABLE 3

| Selection | Amino Acid Substitutions [RRK] (142 or 258) | Reaction progress (% conversion) | % Siamenoside I (72 hr, unless otherwise noted) |
|---|---|---|---|
| wildtype | GCV (E142) | 85 | 52 ± 3.5 |
| E142A | GCV | 91 | 78 ± 2.8 |
| E142A RRK63 | EER (E142A) | 63 | 76 ± 2.4 |
| E142A RRK67 | GRE (E142A) | 67 | 83 ± 2.8 (48 hr) |
| E142A RRK77 | ENR (E142A) | 89 | 76 ± 3.1 |
| E142A RRK134 | DSE (E142A) | 90 | 75 ± 2.9 |
| E142A RRK142 | ESG (E142A) | 88 | 73 ± 4.1 |
| E142A RRK146 | NDE (E142A) | 89 | 74 ± 2.1 |
| D258E | (D258E) | 99 | 55 |

The invention claimed is:

1. A modified beta-galactosidase enzyme comprising one or more mutations in the amino acid residues 200 through 212, wherein the beta-galactosidase enzyme having at least 50% identity to *Aspergillus oryzae* beta-galactosidase comprises one or more mutations selected from G204G, C205R, V208E or combinations thereof.

2. The modified beta-galactosidase enzyme of claim 1, wherein the beta-galactosidase enzyme having at least 50% identity to *Aspergillus oryzae* beta-galactosidase comprises the mutations G204G, C205R and V208 E.

3. A modified beta-galactosidase enzyme comprising one or more mutations in the amino acid residues 200 through 212, wherein the beta-galactosidase enzyme having at least 50% identity to *Aspergillus oryzae* beta-galactosidase comprises one or more mutations in the loop region are selected from E142A, G204G, C205R, and V208E.

4. The modified beta-galactosidase enzyme of claim 3, wherein the beta-galactosidase enzyme having at least 50% identity to *Aspergillus oryzae* beta-galactosidase comprises the mutations E142A, G204G, C205R and V208.

5. A method for purifying Siamenoside I from a reaction mixture comprising:

a) providing a mixture of low purity mogrosides and reaction mixture reagents;
b) separating the mogrosides from the reaction mixture reagents by (i) adjusting the pH of the mixture of a) to about 10 or higher, (ii) adding alcohol to provide an alcoholic solution and (iii) filtering the alcoholic solution through a first ultrafiltration membrane to provide a first filtered solution;
c) adjusting pH of the first filtered solution to between about 5 and about 7 and filtering the through a second ultrafiltration membrane to provide a second filtered solution;
d) performing diafiltration on the second filtered solution to concentrate the mogrosides, providing a mogroside mixture, then mixing the mogroside mixture with water/ammonia acetate to provide a mogroside/ammonium acetate solution;
e) contacting the mogroside/ammonia acetate solution with a fractionation column;
f) eluting and collecting fractions containing Siamenoside I; and
g) drying the fractions containing Siamenoside I to obtain high purity Siamenoside I with a Siamenoside content of more than about 60% (w/w).

6. The method of claim 5, wherein the mogroside mixture of step a) comprises at least 90% Mogroside V.

7. The method of claim 5, wherein the mogroside mixture of step a) comprises at least 95% Mogroside V.

\* \* \* \* \*